US012778787B2

(12) United States Patent
Davis et al.

(10) Patent No.: US 12,778,787 B2
(45) Date of Patent: Nov. 3, 2026

(54) MALE FLUID COLLECTION ASSEMBLIES AND SYSTEMS, METHODS OF USING, AND METHODS OF MANUFACTURING THE SAME

(71) Applicant: PUREWICK CORPORATION

(72) Inventors: Kathleen Davis, Atlanta, GA (US); Robert Hine, Covington, GA (US); Kamil Szymaniak, Dacula, GA (US); Katie Grupp, Alpharetta, GA (US)

(73) Assignee: PUREWICK CORPORATION, Covington, GA (US)

( * ) Notice: Subject to any disclaimer, the term of this patent is extended or adjusted under 35 U.S.C. 154(b) by 0 days.

(21) Appl. No.: 18/164,800

(22) Filed: Feb. 6, 2023

(65) Prior Publication Data

US 2023/0240884 A1 Aug. 3, 2023

Related U.S. Application Data

(63) Continuation of application No. PCT/US2022/014285, filed on Jan. 28, 2022.

(51) Int. Cl.
*A61F 5/453* (2006.01)
*A61F 5/44* (2006.01)

(52) U.S. Cl.
CPC ............ *A61F 5/453* (2013.01); *A61F 5/4405* (2013.01)

(58) Field of Classification Search
CPC .. A61F 5/455; A61F 5/48; A61F 5/451; A61F 5/4405; A61F 5/453
See application file for complete search history.

(56) References Cited

U.S. PATENT DOCUMENTS

| | | | |
|---|---|---|---|
| 670,602 | A | 3/1901 | Baker |
| 737,443 | A | 8/1903 | Mooers |

(Continued)

FOREIGN PATENT DOCUMENTS

| | | | |
|---|---|---|---|
| AU | 2018216821 | A1 | 8/2019 |
| AU | 2021299304 | A1 | 2/2023 |

(Continued)

OTHER PUBLICATIONS

US 9,908,683 B2, 03/2018, Sandhausen et al. (withdrawn)

(Continued)

*Primary Examiner* — Rebecca E Eisenberg
*Assistant Examiner* — Gabriella E Burnette
(74) *Attorney, Agent, or Firm* — Ballard Spahr LLP

(57) ABSTRACT

An example fluid collection assembly includes a sheath and a base. The sheath includes a fluid impermeable barrier having a proximal region and a distal region extending from the proximal region. The proximal region exhibits a first width and the distal region exhibits a second width that is less than the first width. The proximal region defines an opening and the distal region defines a fluid outlet. The fluid impermeable barrier define a chamber. The sheath also includes at least one porous material disposed in the chamber. The base may be attached to or configured to be attached to the sheath. The base defines an aperture that is aligned with the opening when the base is attached to the sheath. The base is configured to be secured to a region about a penis of an individual with the aperture positioned over the penis.

33 Claims, 10 Drawing Sheets

(56) References Cited

U.S. PATENT DOCUMENTS

| | | | | | |
|---|---|---|---|---|---|
| 976,883 | A | | 11/1910 | Keagy et al. | |
| 1,015,905 | A | | 1/1912 | Northrop | |
| 1,032,841 | A | | 7/1912 | Koenig | |
| 1,178,644 | A | | 4/1916 | Johnson | |
| 1,229,423 | A | | 6/1917 | Eckenrode | |
| 1,387,726 | A | | 8/1921 | Karge | |
| 1,742,080 | A | | 12/1929 | Jones | |
| 1,979,899 | A | | 11/1934 | Obrien et al. | |
| 2,241,010 | A | | 5/1941 | Chipley | |
| 2,262,772 | A | | 11/1941 | Peder | |
| 2,326,881 | A | | 8/1943 | Packer | |
| 2,379,346 | A | | 6/1945 | Farrell | |
| 2,485,555 | A | | 10/1949 | Bester | |
| 2,571,357 | A | | 10/1951 | Charles | |
| 2,613,670 | A | | 10/1952 | Edward | |
| 2,616,426 | A | | 11/1952 | Adele | |
| 2,644,234 | A | | 7/1953 | Earl | |
| 2,648,335 | A | | 8/1953 | Chambers | |
| 2,789,560 | A | | 4/1957 | Weimer | |
| 2,859,786 | A | | 11/1958 | Tupper | |
| 2,944,551 | A | | 7/1960 | Carl | |
| 2,968,046 | A | | 1/1961 | Duke | |
| 2,971,512 | A | | 2/1961 | Reinhardt | |
| 3,032,038 | A | | 5/1962 | Swinn | |
| 3,077,883 | A | | 2/1963 | Hill | |
| 3,087,938 | A | | 4/1963 | Hans et al. | |
| 3,089,493 | A | * | 5/1963 | Galindo .................. | A61F 5/445 604/344 |
| 3,114,916 | A | | 12/1963 | Hadley | |
| 3,169,528 | A | | 2/1965 | Knox et al. | |
| 3,171,506 | A | | 3/1965 | Therkel | |
| 3,175,719 | A | | 3/1965 | Herndon | |
| 3,194,238 | A | | 7/1965 | Breece | |
| 3,198,994 | A | | 8/1965 | Hildebrandt et al. | |
| 3,221,742 | A | | 12/1965 | Egon | |
| 3,312,221 | A | | 4/1967 | Overment | |
| 3,312,981 | A | | 4/1967 | Mcguire et al. | |
| 3,340,876 | A | | 9/1967 | Hill | |
| 3,349,768 | A | | 10/1967 | Keane | |
| 3,356,091 | A | | 12/1967 | Patterson | |
| 3,362,590 | A | | 1/1968 | Gene | |
| 3,366,116 | A | | 1/1968 | Huck | |
| 3,368,564 | A | | 2/1968 | Selix | |
| 3,369,940 | A | | 2/1968 | Slautterback | |
| 3,398,848 | A | | 8/1968 | Donovan | |
| 3,400,717 | A | | 9/1968 | Bruce et al. | |
| 3,406,688 | A | | 10/1968 | Bruce | |
| 3,411,504 | A | | 11/1968 | Glassman | |
| 3,424,163 | A | | 1/1969 | Gravdahl | |
| 3,425,471 | A | | 2/1969 | Yates | |
| 3,434,565 | A | | 3/1969 | Fischer | |
| 3,447,536 | A | | 6/1969 | Snyder | |
| 3,511,241 | A | * | 5/1970 | Lee ......................... | A61F 5/453 604/352 |
| 3,512,185 | A | | 5/1970 | Ellis | |
| 3,520,300 | A | | 7/1970 | Flower | |
| 3,528,423 | A | | 9/1970 | Lee | |
| 3,608,552 | A | | 9/1971 | Broerman | |
| 3,613,123 | A | * | 10/1971 | Langstrom ............ | A61F 5/4401 4/144.1 |
| 3,648,700 | A | | 3/1972 | Warner | |
| 3,651,810 | A | | 3/1972 | Ormerod | |
| 3,661,155 | A | | 5/1972 | Lindan | |
| 3,683,918 | A | * | 8/1972 | Pizzella .................. | A61F 5/443 604/347 |
| 3,690,315 | A | | 9/1972 | Chittenden et al. | |
| 3,699,815 | A | | 10/1972 | Holbrook | |
| 3,720,554 | A | | 3/1973 | Stumpf | |
| 3,721,243 | A | | 3/1973 | Greth et al. | |
| 3,726,277 | A | | 4/1973 | Hirschman | |
| 3,727,788 | A | | 4/1973 | Holbrook | |
| 3,730,411 | A | | 5/1973 | Brockmuller | |
| 3,742,952 | A | | 7/1973 | Magers et al. | |
| 3,742,953 | A | | 7/1973 | Lee | |
| 3,757,355 | A | | 9/1973 | Allen et al. | |
| 3,788,324 | A | | 1/1974 | Lim | |
| 3,843,016 | A | | 10/1974 | Bornhorst et al. | |
| 3,863,638 | A | | 2/1975 | Rogers et al. | |
| 3,863,798 | A | | 2/1975 | Kurihara et al. | |
| 3,864,759 | A | | 2/1975 | Horiuchi | |
| 3,865,109 | A | | 2/1975 | Elmore et al. | |
| 3,881,486 | A | | 5/1975 | Fenton | |
| 3,881,489 | A | | 5/1975 | Hartwell | |
| 3,915,189 | A | | 10/1975 | Holbrook et al. | |
| 3,931,650 | A | | 1/1976 | Miller | |
| 3,931,819 | A | | 1/1976 | Weedle | |
| 3,964,786 | A | | 6/1976 | Mashuda | |
| 3,998,228 | A | | 12/1976 | Poidomani | |
| 3,999,550 | A | | 12/1976 | Martin | |
| 4,006,793 | A | | 2/1977 | Robinson | |
| 4,015,604 | A | | 4/1977 | Csillag | |
| 4,020,843 | A | | 5/1977 | Kanall | |
| 4,022,211 | A | | 5/1977 | Timmons et al. | |
| 4,022,213 | A | | 5/1977 | Stein | |
| 4,023,216 | A | | 5/1977 | Li | |
| 4,027,776 | A | | 6/1977 | Douglas | |
| 4,031,897 | A | | 6/1977 | Graetz | |
| 4,042,337 | A | | 8/1977 | Griffith | |
| 4,064,962 | A | | 12/1977 | Hunt | |
| 4,069,817 | A | | 1/1978 | Fenole et al. | |
| 4,084,589 | A | | 4/1978 | Kulvi | |
| 4,096,897 | A | * | 6/1978 | Cammarata, III ........ | A61J 1/10 604/408 |
| 4,116,197 | A | | 9/1978 | Bermingham | |
| 4,140,739 | A | | 2/1979 | Cotten | |
| 4,180,178 | A | | 12/1979 | Turner | |
| 4,187,953 | A | | 2/1980 | Turner | |
| 4,194,508 | A | | 3/1980 | Anderson | |
| 4,197,849 | A | | 4/1980 | Bostick | |
| 4,200,102 | A | | 4/1980 | Duhamel et al. | |
| 4,202,058 | A | | 5/1980 | Anderson | |
| 4,203,503 | A | | 5/1980 | Bertotti et al. | |
| 4,209,076 | A | | 6/1980 | Bertotti et al. | |
| D255,935 | S | | 7/1980 | Cullis et al. | |
| 4,223,677 | A | | 9/1980 | Anderson | |
| 4,233,025 | A | | 11/1980 | Larson et al. | |
| 4,233,978 | A | | 11/1980 | Hickey | |
| 4,246,901 | A | | 1/1981 | Frosch et al. | |
| 4,253,542 | A | | 3/1981 | Ruspa et al. | |
| 4,257,418 | A | | 3/1981 | Hessner | |
| 4,270,539 | A | | 6/1981 | Frosch et al. | |
| 4,280,498 | A | | 7/1981 | Jensen | |
| 4,281,655 | A | | 8/1981 | Terauchi | |
| 4,292,916 | A | | 10/1981 | Bradley et al. | |
| 4,330,239 | A | | 5/1982 | Gannaway | |
| 4,345,341 | A | | 8/1982 | Saito | |
| 4,349,029 | A | | 9/1982 | Mott | |
| 4,352,356 | A | | 10/1982 | Tong | |
| 4,356,012 | A | | 10/1982 | Hofstetter | |
| 4,360,933 | A | | 11/1982 | Kimura et al. | |
| 4,365,363 | A | | 12/1982 | Windauer | |
| 4,372,299 | A | | 2/1983 | Fixel | |
| 4,375,841 | A | | 3/1983 | Vielbig | |
| 4,387,726 | A | | 6/1983 | Denard | |
| 4,403,991 | A | | 9/1983 | Hill | |
| 4,421,511 | A | | 12/1983 | Steer et al. | |
| 4,425,130 | A | | 1/1984 | Desmarais | |
| 4,446,986 | A | | 5/1984 | Bowen et al. | |
| 4,453,938 | A | | 6/1984 | Brendling | |
| 4,457,314 | A | | 7/1984 | Knowles | |
| 4,457,758 | A | | 7/1984 | Norton | |
| 4,476,879 | A | | 10/1984 | Jackson | |
| 4,512,771 | A | | 4/1985 | Norton | |
| 4,526,688 | A | | 7/1985 | Schmidt et al. | |
| 4,528,703 | A | | 7/1985 | Kraus | |
| 4,533,354 | A | | 8/1985 | Jensen et al. | |
| 4,533,357 | A | | 8/1985 | Hall | |
| D280,438 | S | | 9/1985 | Wendt | |
| 4,551,141 | A | | 11/1985 | Mcneil | |
| 4,553,968 | A | | 11/1985 | Komis | |
| 4,568,341 | A | | 2/1986 | Mitchell et al. | |
| 4,581,026 | A | | 4/1986 | Schneider | |
| 4,583,983 | A | | 4/1986 | Einhorn et al. | |
| 4,589,516 | A | | 5/1986 | Inoue et al. | |

(56) References Cited

U.S. PATENT DOCUMENTS

| | | | |
|---|---|---|---|
| 4,601,716 | A | 7/1986 | Smith |
| 4,610,675 | A | 9/1986 | Triunfol |
| 4,620,333 | A | 11/1986 | Ritter |
| 4,626,250 | A | 12/1986 | Schneider |
| 4,627,846 | A | 12/1986 | Ternstroem |
| 4,631,061 | A | 12/1986 | Martin |
| 4,645,275 | A | 2/1987 | Pucci |
| 4,650,477 | A | 3/1987 | Johnson |
| 4,655,754 | A | 4/1987 | Richmond et al. |
| 4,656,675 | A | 4/1987 | Fajnsztajn |
| 4,681,570 | A | 7/1987 | Dalton |
| 4,681,572 | A | 7/1987 | Tokarz et al. |
| 4,681,577 | A | 7/1987 | Stern et al. |
| 4,692,160 | A | 9/1987 | Nussbaumer |
| 4,707,864 | A | 11/1987 | Ikematsu et al. |
| 4,713,065 | A | 12/1987 | Koot |
| 4,713,066 | A | 12/1987 | Komis |
| 4,723,953 | A | 2/1988 | Pratt et al. |
| 4,735,841 | A | 4/1988 | Sourdet |
| 4,743,236 | A | 5/1988 | Manschot |
| 4,747,166 | A | 5/1988 | Kuntz |
| 4,752,944 | A | 6/1988 | Conrads et al. |
| 4,759,753 | A | 7/1988 | Schneider et al. |
| 4,769,215 | A | 9/1988 | Ehrenkranz |
| 4,771,484 | A | 9/1988 | Mozell |
| 4,772,280 | A | 9/1988 | Rooyakkers |
| 4,775,458 | A | 10/1988 | Forester |
| 4,784,654 | A | 11/1988 | Beecher |
| 4,790,830 | A | 12/1988 | Hamacher |
| 4,790,835 | A | 12/1988 | Elias |
| 4,791,686 | A | 12/1988 | Taniguchi et al. |
| 4,795,449 | A | 1/1989 | Schneider et al. |
| 4,798,603 | A | 1/1989 | Meyer et al. |
| 4,799,928 | A | 1/1989 | Crowley |
| 4,804,377 | A | 2/1989 | Hanifl et al. |
| 4,812,053 | A | 3/1989 | Bhattacharjee |
| 4,813,943 | A | 3/1989 | Smith |
| 4,820,291 | A | 4/1989 | Terauchi et al. |
| 4,820,297 | A | 4/1989 | Kaufman et al. |
| 4,841,728 | A | 6/1989 | Jean et al. |
| 4,846,818 | A | 7/1989 | Keldahl et al. |
| 4,846,819 | A | 7/1989 | Welch |
| 4,846,824 | A | 7/1989 | Schultz et al. |
| 4,846,909 | A | 7/1989 | Klug et al. |
| 4,857,064 | A | 8/1989 | Mendoza |
| 4,865,595 | A | 9/1989 | Heyden |
| 4,872,299 | A | 10/1989 | Troutner et al. |
| 4,875,898 | A | 10/1989 | Eakin |
| 4,880,417 | A | 11/1989 | Yabrov et al. |
| 4,882,794 | A | 11/1989 | Stewart |
| 4,883,465 | A | 11/1989 | Brennan |
| 4,886,498 | A | 12/1989 | Newton |
| 4,886,508 | A | 12/1989 | Washington |
| 4,886,509 | A | 12/1989 | Mattsson |
| 4,889,532 | A | 12/1989 | Metz et al. |
| 4,889,533 | A | 12/1989 | Beecher |
| 4,890,691 | A | 1/1990 | Ching-ho |
| 4,895,140 | A | 1/1990 | Bellak |
| 4,903,254 | A | 2/1990 | Haas |
| 4,904,248 | A | 2/1990 | Vaillancourt |
| D306,759 | S | 3/1990 | D'Alo |
| 4,905,692 | A | 3/1990 | More |
| 4,911,262 | A | 3/1990 | Tani et al. |
| 4,930,997 | A | 6/1990 | Bennett |
| 4,936,838 | A | 6/1990 | Cross et al. |
| 4,950,262 | A | 8/1990 | Takagi |
| 4,955,922 | A | 9/1990 | Terauchi |
| 4,957,487 | A | 9/1990 | Gerow |
| 4,965,460 | A | 10/1990 | Tanaka et al. |
| 4,986,823 | A | 1/1991 | Anderson et al. |
| 4,987,849 | A | 1/1991 | Sherman |
| 5,002,541 | A | 3/1991 | Conkling et al. |
| 5,004,463 | A | 4/1991 | Nigay |
| 5,013,308 | A | 5/1991 | Sullivan et al. |
| 5,030,229 | A | 7/1991 | Yang |
| 5,031,248 | A | 7/1991 | Kemper |
| 5,045,077 | A | 9/1991 | Blake |
| 5,045,283 | A | 9/1991 | Patel |
| 5,049,144 | A | 9/1991 | Payton |
| 5,053,339 | A | 10/1991 | Patel |
| 5,057,092 | A | 10/1991 | Webster |
| 5,058,088 | A | 10/1991 | Haas et al. |
| 5,071,347 | A | 12/1991 | McGuire |
| 5,078,707 | A | 1/1992 | Peter |
| 5,084,037 | A | 1/1992 | Barnett |
| 5,100,396 | A | 3/1992 | Zamierowski |
| 5,102,404 | A | 4/1992 | Goldberg et al. |
| 5,112,324 | A | 5/1992 | Wallace |
| 5,134,994 | A | 8/1992 | Say |
| 5,137,033 | A | 8/1992 | Norton |
| 5,147,301 | A | 9/1992 | Ruvio |
| 5,176,667 | A | 1/1993 | Debring |
| 5,195,997 | A | 3/1993 | Carns |
| 5,196,654 | A | 3/1993 | Diflora et al. |
| 5,199,444 | A | 4/1993 | Wheeler |
| 5,203,699 | A | 4/1993 | McGuire |
| 5,234,419 | A | 8/1993 | Bryant et al. |
| 5,244,458 | A | 9/1993 | Takasu |
| 5,246,454 | A | 9/1993 | Peterson |
| 5,267,988 | A | 12/1993 | Farkas |
| 5,275,307 | A | 1/1994 | Freese |
| 5,282,795 | A | 2/1994 | Finney |
| 5,294,983 | A | 3/1994 | Ersoz et al. |
| 5,295,979 | A | 3/1994 | Delaurentis et al. |
| 5,295,983 | A | 3/1994 | Kubo |
| 5,300,052 | A * | 4/1994 | Kubo ...................... A61F 5/453 604/350 |
| 5,304,749 | A | 4/1994 | Crandell |
| 5,312,383 | A | 5/1994 | Kubalak |
| 5,318,550 | A | 6/1994 | Cermak et al. |
| 5,330,457 | A | 7/1994 | Cohen |
| 5,330,459 | A | 7/1994 | Lavon et al. |
| 5,334,174 | A | 8/1994 | Street |
| 5,334,176 | A | 8/1994 | Buenger et al. |
| 5,340,840 | A | 8/1994 | Park et al. |
| D354,129 | S | 1/1995 | Salvadori |
| D354,560 | S | 1/1995 | Chase |
| 5,382,244 | A | 1/1995 | Telang |
| 5,397,315 | A | 3/1995 | Schmidt et al. |
| 5,409,014 | A | 4/1995 | Napoli et al. |
| 5,409,475 | A | 4/1995 | Steer |
| 5,411,495 | A | 5/1995 | Willingham |
| 5,423,784 | A | 6/1995 | Metz |
| 5,423,788 | A | 6/1995 | Rollins et al. |
| 5,437,836 | A | 8/1995 | Yamada |
| 5,455,091 | A | 10/1995 | Oreglia et al. |
| 5,456,246 | A | 10/1995 | Schmieding et al. |
| 5,466,229 | A | 11/1995 | Elson et al. |
| 5,478,334 | A | 12/1995 | Bernstein |
| 5,499,977 | A | 3/1996 | Marx |
| 5,525,407 | A | 6/1996 | Yang |
| 5,543,042 | A | 8/1996 | Filan et al. |
| D373,928 | S | 9/1996 | Green |
| 5,582,604 | A | 12/1996 | Ahr et al. |
| 5,592,950 | A | 1/1997 | Kopelowicz |
| 5,593,389 | A | 1/1997 | Chang |
| 5,605,161 | A | 2/1997 | Cross |
| 5,614,699 | A | 3/1997 | Yashiro et al. |
| 5,618,277 | A | 4/1997 | Goulter |
| 5,628,735 | A | 5/1997 | Skow |
| 5,632,736 | A | 5/1997 | Block |
| 5,636,643 | A | 6/1997 | Argenta et al. |
| 5,637,104 | A | 6/1997 | Ball et al. |
| 5,641,277 | A | 6/1997 | Gondek |
| D380,543 | S | 7/1997 | Piontek et al. |
| 5,662,633 | A | 9/1997 | Doak et al. |
| 5,674,212 | A | 10/1997 | Osborn et al. |
| 5,678,564 | A | 10/1997 | Lawrence et al. |
| 5,678,654 | A | 10/1997 | Uzawa |
| 5,681,297 | A | 10/1997 | Hashimoto et al. |
| 5,687,429 | A | 11/1997 | Rahlff |
| 5,695,485 | A | 12/1997 | Duperret et al. |
| 5,695,487 | A | 12/1997 | Cohen et al. |
| 5,700,254 | A | 12/1997 | Mcdowall et al. |

(56) References Cited

U.S. PATENT DOCUMENTS 5,701,612 A 12/1997 Daneshvar
5,705,777 A 1/1998 Flanigan et al.
5,735,835 A 4/1998 Holland
5,735,837 A 4/1998 Ishikawa
5,752,944 A 5/1998 Dann et al.
5,763,333 A 6/1998 Suzuki et al.
5,772,644 A 6/1998 Bark et al.
5,792,132 A 8/1998 Garcia
5,827,243 A 10/1998 Palestrant
5,827,247 A 10/1998 Kay
5,827,250 A 10/1998 Fujioka et al.
5,827,257 A 10/1998 Fujioka et al.
D401,699 S 11/1998 Herchenbach et al.
5,859,393 A 1/1999 Cummins et al.
5,865,378 A 2/1999 Hollinshead et al.
5,873,869 A 2/1999 Hammons et al.
5,876,393 A 3/1999 Ahr et al.
5,887,291 A 3/1999 Bellizzi
5,891,125 A 4/1999 Plumley
5,894,608 A 4/1999 Birbara
5,895,349 A 4/1999 Tihon
D409,303 S 5/1999 Oepping
5,911,222 A 6/1999 Lawrence et al.
5,956,782 A 9/1999 Olguin
5,957,904 A 9/1999 Holland
5,968,026 A 10/1999 Osborn et al.
5,972,505 A 10/1999 Phillips et al.
6,007,524 A 12/1999 Schneider
6,007,526 A 12/1999 Passalaqua et al.
D421,307 S 2/2000 Harmanoglu
6,039,060 A 3/2000 Rower
6,050,983 A 4/2000 Moore et al.
6,059,762 A 5/2000 Boyer et al.
6,061,905 A 5/2000 Logic
6,063,064 A 5/2000 Tuckey et al.
6,083,602 A 7/2000 Caldwell et al.
6,098,625 A 8/2000 Winkler
6,105,174 A 8/2000 Karlsten et al.
6,113,582 A 9/2000 Dwork
6,117,163 A 9/2000 Bierman
6,123,398 A 9/2000 Arai et al.
6,129,718 A 10/2000 Wada et al.
6,131,964 A 10/2000 Sareshwala
6,152,902 A 11/2000 Christian et al.
6,164,569 A 12/2000 Hollinshead et al.
6,177,606 B1 1/2001 Etheredge et al.
6,209,142 B1 4/2001 Mattsson et al.
6,220,050 B1 4/2001 Cooksey
6,244,311 B1 6/2001 Hand et al.
6,248,096 B1 6/2001 Dwork et al.
6,263,887 B1 7/2001 Dunn
6,283,246 B1 9/2001 Nishikawa
6,296,627 B1 10/2001 Edwards
6,311,339 B1 11/2001 Kraus
6,316,688 B1 11/2001 Hammons et al.
6,336,919 B1 1/2002 Davis et al.
6,338,729 B1 1/2002 Wada et al.
6,352,525 B1 3/2002 Wakabayashi
6,394,988 B1 5/2002 Hashimoto
6,395,956 B1 5/2002 Glasgow et al.
6,398,742 B1 6/2002 Kim
6,406,463 B1 6/2002 Brown
6,409,712 B1 6/2002 Dutari et al.
6,415,888 B2 7/2002 An et al.
6,416,500 B1 7/2002 Wada et al.
6,417,750 B1 7/2002 Sohn
6,423,045 B1 7/2002 Wise et al.
6,428,521 B1 8/2002 Droll
6,428,522 B1 8/2002 Dipalma et al.
6,446,454 B1 9/2002 Lee et al.
6,461,340 B1 10/2002 Lenker et al.
6,467,570 B1 10/2002 Herold
6,475,198 B1 11/2002 Lipman et al.
6,479,726 B1 11/2002 Cole et al.
6,491,673 B1 12/2002 Palumbo et al.
6,508,794 B1 1/2003 Palumbo et al.
6,524,292 B1 2/2003 Dipalma et al.
6,526,603 B1 3/2003 Murphy
6,540,729 B1 4/2003 Wada et al.
6,547,771 B2 4/2003 Robertson et al.
6,551,293 B1 4/2003 Mitchell
6,569,133 B2 5/2003 Cheng et al.
D476,518 S 7/2003 Doppelt
6,592,560 B2 7/2003 Snyder et al.
6,610,038 B1 8/2003 Dipalma et al.
6,618,868 B2 9/2003 Minnick
6,620,142 B1 9/2003 Flueckiger
6,629,651 B1 10/2003 Male et al.
6,635,037 B1 10/2003 Bennett
6,635,038 B2 10/2003 Scovel
6,652,495 B1 11/2003 Walker
6,666,850 B1 12/2003 Ahr et al.
6,685,684 B1 2/2004 Falconer
6,695,828 B1 2/2004 Dipalma et al.
6,699,174 B1 3/2004 Bennett
6,700,034 B1 3/2004 Lindsay et al.
6,702,793 B1 3/2004 Sweetser et al.
6,706,027 B2 3/2004 Harvie et al.
6,732,384 B2 5/2004 Scott
6,736,977 B1 5/2004 Hall et al.
6,740,066 B2 5/2004 Wolff et al.
6,764,477 B1 7/2004 Chen et al.
6,783,519 B2 8/2004 Samuelsson
6,796,974 B2 9/2004 Palumbo et al.
6,814,547 B2 11/2004 Childers et al.
6,848,719 B2 2/2005 Rowley
6,849,065 B2 2/2005 Schmidt et al.
6,857,137 B2 2/2005 Otto
6,878,647 B1 4/2005 Rezai et al.
6,885,690 B2 4/2005 Aggerstam et al.
6,888,044 B2 5/2005 Fell et al.
6,893,425 B2 5/2005 Dunn et al.
6,912,737 B2 7/2005 Ernest et al.
6,918,899 B2 7/2005 Harvie
6,979,324 B2 12/2005 Bybordi et al.
7,018,366 B2 3/2006 Easter
7,018,367 B2 3/2006 Nava
7,066,411 B2 6/2006 Male et al.
7,087,043 B2 8/2006 Dolan
7,122,023 B1 10/2006 Hinoki
7,125,399 B2 10/2006 Miskie
7,131,964 B2 11/2006 Harvie
7,135,012 B2 11/2006 Harvie
7,141,043 B2 11/2006 Harvie
D533,972 S 12/2006 La
7,160,273 B2 1/2007 Greter et al.
7,166,092 B2 1/2007 Elson et al.
7,171,699 B2 2/2007 Ernest et al.
7,171,871 B2 2/2007 Kozak
7,179,951 B2 2/2007 Krishnaswamy-Mirle et al.
7,181,781 B1 2/2007 Trabold et al.
7,186,245 B1 3/2007 Cheng et al.
7,192,424 B2 3/2007 Cooper
7,219,764 B1 5/2007 Forbes
7,220,250 B2 5/2007 Suzuki et al.
D562,975 S 2/2008 Otto
7,335,189 B2 2/2008 Harvie
7,358,282 B2 4/2008 Krueger et al.
7,390,320 B2 6/2008 Machida et al.
7,438,706 B2 10/2008 Koizumi et al.
7,488,310 B2 2/2009 Yang
7,491,194 B1 2/2009 Oliwa
D591,106 S 4/2009 Dominique et al.
7,513,381 B2 4/2009 Heng et al.
7,520,872 B2 4/2009 Biggie et al.
D593,801 S 6/2009 Wilson et al.
7,540,364 B2 6/2009 Sanderson
7,549,511 B2 6/2009 Marocco
7,549,512 B2 6/2009 Newberry
7,585,293 B2 9/2009 Vermaak
7,588,560 B1 9/2009 Dunlop
7,637,905 B2 12/2009 Saadat et al.
7,658,730 B2 2/2010 Conley
7,665,359 B2 2/2010 Barber

(56) References Cited

U.S. PATENT DOCUMENTS

| | | | |
|---|---|---|---|
| 7,682,347 | B2 | 3/2010 | Parks et al. |
| 7,687,004 | B2 | 3/2010 | Allen |
| 7,695,459 | B2 | 4/2010 | Gilbert et al. |
| 7,695,460 | B2 | 4/2010 | Wada et al. |
| 7,699,818 | B2 | 4/2010 | Gilbert |
| 7,699,831 | B2 | 4/2010 | Bengtson et al. |
| 7,722,584 | B2 | 5/2010 | Tanaka et al. |
| 7,727,206 | B2 | 6/2010 | Gorres |
| 7,740,620 | B2 | 6/2010 | Gilbert et al. |
| 7,749,205 | B2 | 7/2010 | Tazoe et al. |
| 7,755,497 | B2 | 7/2010 | Wada et al. |
| 7,766,887 | B2 | 8/2010 | Burns et al. |
| 7,803,144 | B1 | 9/2010 | Vollrath |
| D625,407 | S | 10/2010 | Koizumi et al. |
| 7,806,879 | B2 | 10/2010 | Brooks et al. |
| 7,811,272 | B2 | 10/2010 | Lindsay et al. |
| 7,815,067 | B2 | 10/2010 | Matsumoto et al. |
| 7,833,169 | B2 | 11/2010 | Hannon |
| 7,857,806 | B2 | 12/2010 | Karpowicz et al. |
| 7,866,942 | B2 | 1/2011 | Harvie |
| 7,871,385 | B2 | 1/2011 | Levinson et al. |
| 7,875,010 | B2 | 1/2011 | Frazier et al. |
| 7,901,389 | B2 | 3/2011 | Mombrinie |
| 7,927,320 | B2 | 4/2011 | Goldwasser et al. |
| 7,927,321 | B2 | 4/2011 | Marland |
| 7,931,634 | B2 | 4/2011 | Swiecicki et al. |
| 7,939,706 | B2 | 5/2011 | Okabe et al. |
| 7,946,443 | B2 | 5/2011 | Stull et al. |
| 7,947,025 | B2 | 5/2011 | Buglino et al. |
| 7,963,419 | B2 | 6/2011 | Burney et al. |
| 7,976,519 | B2 | 7/2011 | Bubb et al. |
| 7,981,087 | B2 | 7/2011 | Gesler, III |
| 7,993,318 | B2 | 8/2011 | Olsson et al. |
| 8,015,627 | B2 | 9/2011 | Baker et al. |
| 8,016,071 | B1 | 9/2011 | Martinus et al. |
| 8,028,460 | B2 | 10/2011 | Williams |
| 8,047,398 | B2 | 11/2011 | Dimartino et al. |
| 8,075,538 | B2 | 12/2011 | Vernon |
| 8,083,094 | B2 | 12/2011 | Caulfield et al. |
| 8,128,608 | B2 | 3/2012 | Thevenin |
| 8,156,941 | B1 | 4/2012 | Simms |
| 8,167,860 | B1 | 5/2012 | Siegel |
| 8,181,651 | B2 | 5/2012 | Pinel |
| 8,181,819 | B2 | 5/2012 | Burney et al. |
| 8,211,063 | B2 | 7/2012 | Bierman et al. |
| 8,221,369 | B2 | 7/2012 | Parks et al. |
| 8,241,262 | B2 | 8/2012 | Mahnensmith |
| 8,277,426 | B2 | 10/2012 | Wilcox et al. |
| 8,287,508 | B1 | 10/2012 | Sanchez |
| 8,303,554 | B2 | 11/2012 | Tsai et al. |
| 8,322,565 | B2 | 12/2012 | Caulfield et al. |
| 8,337,477 | B2 | 12/2012 | Parks et al. |
| D674,241 | S | 1/2013 | Bickert et al. |
| 8,343,122 | B2 | 1/2013 | Gorres |
| 8,343,125 | B2 | 1/2013 | Kawazoe et al. |
| 8,353,074 | B2 | 1/2013 | Krebs |
| 8,353,886 | B2 | 1/2013 | Bester et al. |
| D676,241 | S | 2/2013 | Merrill |
| 8,388,587 | B1 | 3/2013 | Gmuer et al. |
| 8,388,588 | B2 | 3/2013 | Wada et al. |
| D679,807 | S | 4/2013 | Burgess et al. |
| 8,425,482 | B2 | 4/2013 | Khoubnazar |
| 8,430,855 | B2 | 4/2013 | Burgess et al. |
| 8,434,586 | B2 | 5/2013 | Pawelski et al. |
| 8,449,510 | B2 | 5/2013 | Martini et al. |
| D684,260 | S | 6/2013 | Lund et al. |
| 8,470,230 | B2 | 6/2013 | Caulfield et al. |
| 8,479,941 | B2 | 7/2013 | Matsumoto et al. |
| 8,479,949 | B2 | 7/2013 | Henkel |
| 8,500,719 | B1 | 8/2013 | Simpson et al. |
| 8,512,301 | B2 | 8/2013 | Ma |
| 8,529,530 | B2 | 9/2013 | Koch et al. |
| 8,535,284 | B2 | 9/2013 | Joder et al. |
| 8,546,639 | B2 | 10/2013 | Wada et al. |
| 8,551,062 | B2 | 10/2013 | Kay |
| 8,551,075 | B2 | 10/2013 | Bengtson |
| 8,568,376 | B2 | 10/2013 | Delattre et al. |
| D694,404 | S | 11/2013 | Burgess et al. |
| 8,585,683 | B2 | 11/2013 | Bengtson et al. |
| 8,586,583 | B2 | 11/2013 | Hamblin et al. |
| 8,652,112 | B2 | 2/2014 | Johannison et al. |
| 8,669,412 | B2 | 3/2014 | Fernkvist et al. |
| D702,973 | S | 4/2014 | Norland et al. |
| 8,702,667 | B1 | 4/2014 | Johnson |
| 8,703,032 | B2 | 4/2014 | Menon et al. |
| D704,330 | S | 5/2014 | Cicatelli |
| D704,510 | S | 5/2014 | Mason et al. |
| D705,423 | S | 5/2014 | Walsh Cutler |
| D705,926 | S | 5/2014 | Burgess et al. |
| 8,714,394 | B2 | 5/2014 | Wulf |
| 8,715,267 | B2 | 5/2014 | Bengtson et al. |
| 8,740,852 | B2 | 6/2014 | Aviles |
| 8,757,425 | B2 | 6/2014 | Copeland |
| 8,777,032 | B2 | 7/2014 | Biesecker et al. |
| 8,808,260 | B2 | 8/2014 | Koch et al. |
| 8,839,792 | B2 | 9/2014 | Brunner |
| 8,864,730 | B2 | 10/2014 | Conway et al. |
| 8,881,923 | B2 | 11/2014 | Higginson |
| 8,882,731 | B2 | 11/2014 | Suzuki et al. |
| 8,936,585 | B2 | 1/2015 | Carson et al. |
| D729,581 | S | 5/2015 | Boroski |
| 9,028,460 | B2 | 5/2015 | Medeiros |
| 9,056,698 | B2 | 6/2015 | Noer |
| 9,078,792 | B2 | 7/2015 | Ruiz |
| 9,145,879 | B2 | 9/2015 | Pirovano et al. |
| 9,173,602 | B2 | 11/2015 | Gilbert |
| 9,173,799 | B2 | 11/2015 | Tanimoto et al. |
| 9,187,220 | B2 | 11/2015 | Biesecker et al. |
| 9,199,772 | B2 | 12/2015 | Krippendorf |
| 9,233,020 | B2 | 1/2016 | Matsumiya |
| 9,248,058 | B2 | 2/2016 | Conway et al. |
| 9,308,118 | B1 | 4/2016 | Dupree et al. |
| 9,309,029 | B2 | 4/2016 | Incorvia et al. |
| 9,333,281 | B2 | 5/2016 | Giezendanner et al. |
| 9,381,108 | B2 | 7/2016 | Longoni et al. |
| 9,382,047 | B2 | 7/2016 | Schmidtner et al. |
| 9,402,424 | B2 | 8/2016 | Roy |
| 9,415,191 | B2 | 8/2016 | Aviles |
| 9,456,937 | B2 | 10/2016 | Ellis |
| 9,480,595 | B2 | 11/2016 | Baham et al. |
| 9,517,865 | B2 | 12/2016 | Albers et al. |
| D777,941 | S | 1/2017 | Piramoon |
| 9,533,806 | B2 | 1/2017 | Ding et al. |
| 9,550,611 | B2 | 1/2017 | Hodge |
| 9,555,930 | B2 | 1/2017 | Campbell et al. |
| 9,623,159 | B2 | 4/2017 | Locke |
| D789,522 | S | 6/2017 | Burgess et al. |
| 9,687,849 | B2 | 6/2017 | Bruno et al. |
| 9,694,949 | B2 | 7/2017 | Hendricks et al. |
| 9,709,048 | B2 | 7/2017 | Kinjo |
| 9,713,547 | B2 | 7/2017 | Lee et al. |
| 9,732,754 | B2 | 8/2017 | Huang et al. |
| 9,737,433 | B2 | 8/2017 | Joh |
| 9,752,564 | B2 | 9/2017 | Arceno et al. |
| 9,788,992 | B2 | 10/2017 | Harvie |
| D804,907 | S | 12/2017 | Sandoval |
| D806,236 | S | 12/2017 | Lin |
| 9,868,564 | B2 | 1/2018 | Mcgirr et al. |
| D814,239 | S | 4/2018 | Arora |
| D817,484 | S | 5/2018 | Lafond |
| 9,968,908 | B2 | 5/2018 | Ladrech et al. |
| 10,010,393 | B1 | 7/2018 | Nguyen et al. |
| 10,037,640 | B2 | 7/2018 | Gordon |
| 10,058,470 | B2 | 8/2018 | Phillips |
| 10,098,990 | B2 | 10/2018 | Koch et al. |
| D835,264 | S | 12/2018 | Mozzicato et al. |
| D835,779 | S | 12/2018 | Mozzicato et al. |
| D840,533 | S | 2/2019 | Mozzicato et al. |
| D840,534 | S | 2/2019 | Mozzicato et al. |
| 10,225,376 | B2 | 3/2019 | Perez Martinez |
| 10,226,376 | B2 | 3/2019 | Sanchez et al. |
| 10,258,517 | B1 | 4/2019 | Maschino et al. |
| D848,612 | S | 5/2019 | Mozzicato et al. |
| 10,307,305 | B1 | 6/2019 | Hodges |

(56) References Cited

U.S. PATENT DOCUMENTS 10,335,121 B2 7/2019 Desai
D856,512 S 8/2019 Cowart et al.
10,376,406 B2 8/2019 Newton
10,376,407 B2 8/2019 Newton
10,390,989 B2 8/2019 Sanchez et al.
D858,144 S 9/2019 Fu
10,406,039 B2 9/2019 Villarreal
10,407,222 B2 9/2019 Allen
10,478,356 B2 11/2019 Griffin
10,500,108 B1 12/2019 Maschino et al.
10,502,198 B2 12/2019 Stumpf et al.
10,538,366 B2 1/2020 Pentelovitch et al.
10,569,938 B2 2/2020 Zhao et al.
10,577,156 B2 3/2020 Dagnelie et al.
RE47,930 E 4/2020 Cho
10,618,721 B2 4/2020 Vazin
D884,390 S 5/2020 Wang
10,669,079 B2 6/2020 Freedman et al.
D892,315 S 8/2020 Airy
10,730,672 B2 8/2020 Bertram et al.
10,737,848 B2 8/2020 Philip et al.
10,765,854 B2 9/2020 Law et al.
10,766,670 B2 9/2020 Kittmann
10,799,386 B1 10/2020 Harrison
10,806,623 B2 10/2020 VanMiddendorp et al.
10,806,642 B2 10/2020 Tagomori et al.
D901,214 S 11/2020 Hu
10,849,799 B2 12/2020 Nishikawa et al.
10,857,025 B2 12/2020 Davis et al.
10,865,017 B1 12/2020 Cowart et al.
10,889,412 B2 1/2021 West et al.
10,913,581 B2 2/2021 Stahlecker
D912,244 S 3/2021 Rehm et al.
10,952,889 B2 3/2021 Newton et al.
10,973,378 B2 4/2021 Ryu et al.
10,973,678 B2 4/2021 Newton et al.
10,974,874 B2 4/2021 Ragias et al.
11,000,401 B2 5/2021 Ecklund et al.
11,002,165 B2 5/2021 Poulin
D923,365 S 6/2021 Wang
11,020,567 B2 6/2021 Rule et al.
11,026,829 B2 6/2021 Harvie
11,027,900 B2 6/2021 Liu
11,045,346 B2 6/2021 Argent et al.
D928,946 S 8/2021 Sanchez et al.
11,090,183 B2 8/2021 Sanchez et al.
11,160,695 B2 11/2021 Febo et al.
11,160,697 B2 11/2021 Maschino et al.
11,168,420 B2 11/2021 Kinugasa et al.
11,179,506 B2 11/2021 Barr et al.
11,199,116 B2 12/2021 Ostromecki et al.
11,207,206 B2 12/2021 Sharma et al.
D941,998 S 1/2022 Tretheway et al.
11,226,376 B2 1/2022 Yamauchi et al.
11,253,389 B2 2/2022 Sharma et al.
11,253,407 B2 2/2022 Miao et al.
11,326,586 B2 5/2022 Milner et al.
11,369,508 B2 6/2022 Ecklund et al.
11,369,524 B2 6/2022 Hubbard et al.
11,376,152 B2 7/2022 Sanchez et al.
11,382,786 B2 7/2022 Sanchez et al.
11,382,788 B2 7/2022 Hjorth et al.
11,389,318 B2 7/2022 Radl et al.
11,395,871 B2 7/2022 Radl et al.
11,399,990 B2 8/2022 Suyama
11,426,303 B2 8/2022 Davis et al.
11,446,174 B2 9/2022 Newton
11,504,265 B2 11/2022 Godinez et al.
11,529,252 B2 12/2022 Glithero et al.
11,547,788 B2 1/2023 Radl et al.
11,806,266 B2 11/2023 Sanchez et al.
11,813,189 B2 11/2023 Hussey et al.
11,839,567 B2 12/2023 Davis et al.
D1,010,109 S 1/2024 Ecklund et al.
11,857,716 B2 1/2024 Lee et al.
11,865,030 B2 1/2024 Davis et al.
11,877,948 B2 1/2024 Pinlac
11,890,221 B2 2/2024 Ulreich et al.
11,911,160 B2 2/2024 Woodard et al.
11,925,575 B2 3/2024 Newton
11,938,053 B2 3/2024 Austermann et al.
11,944,740 B2 4/2024 Hughett et al.
11,994,122 B2 5/2024 Bodain
11,998,475 B2 6/2024 Becker et al.
12,023,457 B2 7/2024 Mann et al.
12,042,422 B2 7/2024 Davis et al.
12,048,644 B2 7/2024 Davis
D1,038,385 S 8/2024 Ecklund et al.
12,064,372 B2 8/2024 Godinez et al.
12,070,432 B2 8/2024 Tourchak et al.
12,090,083 B2 9/2024 Ecklund et al.
12,121,468 B2 10/2024 Sanchez et al.
12,133,813 B2 11/2024 Ulreich et al.
12,138,195 B2 11/2024 Alder et al.
D1,054,019 S 12/2024 Miyawaki
12,161,579 B2 12/2024 Sanchez et al.
D1,059,585 S 1/2025 Miyawaki
D1,059,586 S 1/2025 Miyawaki
12,186,229 B2 1/2025 Davis et al.
12,193,962 B2 1/2025 Newton et al.
12,208,031 B2 1/2025 Knapp et al.
12,233,003 B2 2/2025 Newton
D1,067,424 S 3/2025 Naughton et al.
12,245,966 B2 3/2025 Newton
12,257,173 B2 3/2025 Newton et al.
12,274,638 B2 4/2025 Spector
D1,074,995 S 5/2025 Laffay et al.
12,324,765 B2 6/2025 Sanchez et al.
12,350,190 B2 7/2025 Hughett, Sr. et al.
12,447,042 B2 10/2025 Martin et al.
12,465,515 B2 11/2025 Brooks
D1,104,255 S 12/2025 Hanna et al.
D1,107,222 S 12/2025 Ecklund et al.
12,594,182 B2 4/2026 Davis et al.
2001/0037097 A1 11/2001 Cheng et al.
2001/0037098 A1 11/2001 Snyder
2001/0054426 A1 12/2001 Knudson et al.
2002/0019614 A1 2/2002 Woon
2002/0026161 A1 2/2002 Grundke
2002/0026163 A1 2/2002 Grundke
2002/0033200 A1 3/2002 Alex et al.
2002/0042945 A1 4/2002 Sands
2002/0087131 A1 7/2002 Wolff et al.
2002/0091364 A1 7/2002 Prabhakar
2002/0189992 A1 12/2002 Schmidt et al.
2002/0193760 A1 12/2002 Thompson
2002/0193762 A1 12/2002 Suydam
2003/0004436 A1 1/2003 Schmidt et al.
2003/0018309 A1 1/2003 Breznock
2003/0032931 A1 2/2003 Grundke et al.
2003/0032944 A1 2/2003 Cawood
2003/0073964 A1 * 4/2003 Palumbo ................ A61F 13/82
604/338
2003/0074724 A1 4/2003 Sands
2003/0097100 A1 5/2003 Watson
2003/0120178 A1 6/2003 Heki
2003/0129178 A1 7/2003 Wegman et al.
2003/0132352 A1 7/2003 Weaver
2003/0157859 A1 8/2003 Ishikawa
2003/0181880 A1 9/2003 Schwartz
2003/0195484 A1 10/2003 Harvie
2003/0204173 A1 10/2003 Burns et al.
2003/0233079 A1 12/2003 Parks et al.
2004/0002687 A1 1/2004 Burns et al.
2004/0006321 A1 1/2004 Cheng et al.
2004/0015141 A1 1/2004 Cheng et al.
2004/0056122 A1 3/2004 Male et al.
2004/0084465 A1 5/2004 Luburic
2004/0098794 A1 5/2004 Ernest et al.
2004/0102753 A1 5/2004 Butler
2004/0127872 A1 7/2004 Petryk et al.
2004/0128749 A1 7/2004 Scott
2004/0143229 A1 7/2004 Easter
2004/0147863 A1 7/2004 Diaz et al.

(56) References Cited

U.S. PATENT DOCUMENTS

2004/0147894 A1 7/2004 Mizutani et al.
2004/0147895 A1 7/2004 Mizutani et al.
2004/0158221 A1 8/2004 Mizutani et al.
2004/0176731 A1 9/2004 Cheng et al.
2004/0176746 A1 9/2004 Forral
2004/0181201 A1 9/2004 Mizutani et al.
2004/0187200 A1 9/2004 Otto et al.
2004/0191919 A1 9/2004 Unger et al.
2004/0194792 A1 10/2004 Zhuang et al.
2004/0200936 A1 10/2004 Opperthauser
2004/0207530 A1 10/2004 Nielsen
2004/0215133 A1 10/2004 Weber et al.
2004/0236292 A1 11/2004 Tazoe et al.
2004/0243075 A1 12/2004 Harvie
2004/0254547 A1 12/2004 Okabe et al.
2005/0010182 A1 1/2005 Parks et al.
2005/0010197 A1 1/2005 Lau et al.
2005/0033248 A1 2/2005 Machida et al.
2005/0065471 A1 3/2005 Kuntz
2005/0070861 A1 3/2005 Okabe et al.
2005/0070862 A1 3/2005 Tazoe et al.
2005/0082300 A1 4/2005 Modrell et al.
2005/0097662 A1 5/2005 Leimkuhler et al.
2005/0101924 A1 5/2005 Elson et al.
2005/0119630 A1 6/2005 Harvie
2005/0131361 A1 6/2005 Miskie
2005/0137557 A1 6/2005 Swiecicki et al.
2005/0137560 A1 6/2005 Mizutani et al.
2005/0137561 A1 6/2005 Mizutani et al.
2005/0148984 A1 7/2005 Lindsay et al.
2005/0154360 A1 7/2005 Harvie
2005/0177070 A1 8/2005 Levinson et al.
2005/0197639 A1 9/2005 Mombrinie
2005/0197645 A1 9/2005 Karpowicz et al.
2005/0215969 A1 9/2005 Mizutani et al.
2005/0273069 A1 12/2005 Mizutani et al.
2005/0273920 A1 12/2005 Marinas
2005/0277903 A1 12/2005 Mizutani et al.
2005/0277904 A1 12/2005 Chase et al.
2005/0279359 A1 12/2005 LeBlanc et al.
2006/0004332 A1 1/2006 Marx
2006/0005307 A1 1/2006 Arguelles
2006/0015080 A1 1/2006 Mahnensmith
2006/0015081 A1 1/2006 Suzuki et al.
2006/0016778 A1 1/2006 Park
2006/0069359 A1 3/2006 Dipalma et al.
2006/0079852 A1 4/2006 Bubb et al.
2006/0079854 A1 4/2006 Kay et al.
2006/0100596 A1 5/2006 Miskie
2006/0111648 A1 5/2006 Vermaak
2006/0113334 A1 6/2006 Mikhail et al.
2006/0155214 A1 7/2006 Wightman
2006/0166350 A1 7/2006 Lowe et al.
2006/0171997 A1 8/2006 Gruenbacher et al.
2006/0180566 A1 8/2006 Mataya
2006/0200102 A1 9/2006 Cooper
2006/0229575 A1 10/2006 Boiarski
2006/0229576 A1 10/2006 Conway et al.
2006/0231648 A1 10/2006 Male et al.
2006/0235266 A1 10/2006 Nan
2006/0235359 A1 10/2006 Marland
2006/0241553 A1 10/2006 Harvie
2006/0269439 A1 11/2006 White
2006/0277670 A1 12/2006 Baker et al.
2007/0006368 A1 1/2007 Key et al.
2007/0010797 A1 1/2007 Nishtala et al.
2007/0016152 A1 1/2007 Karpowicz et al.
2007/0025886 A1 2/2007 Yong
2007/0038194 A1 2/2007 Wada et al.
2007/0055209 A1 3/2007 Patel et al.
2007/0073252 A1 3/2007 Forgrave
2007/0106177 A1 5/2007 Hama
2007/0117880 A1 5/2007 Elson et al.
2007/0118993 A1 5/2007 Bates
2007/0135786 A1 6/2007 Schmidt et al.
2007/0137718 A1 6/2007 Rushlander et al.
2007/0149935 A1 6/2007 Dirico
2007/0191804 A1 8/2007 Coley
2007/0203464 A1 8/2007 Green et al.
2007/0214553 A1 9/2007 Carromba et al.
2007/0225663 A1 9/2007 Watt et al.
2007/0225666 A1 9/2007 Otto
2007/0225668 A1 9/2007 Otto
2007/0266486 A1 11/2007 Ramirez
2007/0270716 A1 11/2007 Wu et al.
2007/0282309 A1 12/2007 Bengtson et al.
2008/0004576 A1 1/2008 Tanaka et al.
2008/0015526 A1 1/2008 Reiner et al.
2008/0015527 A1 1/2008 House
2008/0033386 A1 2/2008 Okabe et al.
2008/0041869 A1 2/2008 Backaert
2008/0077099 A1 3/2008 House
2008/0091153 A1 4/2008 Harvie
2008/0091158 A1 4/2008 Yang
2008/0091162 A1 4/2008 Maldonado et al.
2008/0114327 A1 5/2008 Barge
2008/0140033 A1 6/2008 Burgess et al.
2008/0167634 A1 7/2008 Kouta et al.
2008/0183157 A1 7/2008 Walters
2008/0200884 A1 8/2008 Perkins et al.
2008/0215031 A1 9/2008 Belfort et al.
2008/0234642 A1 9/2008 Patterson et al.
2008/0269703 A1 10/2008 Collins et al.
2008/0281282 A1 11/2008 Finger et al.
2008/0287894 A1 11/2008 Van Den Heuvel et al.
2008/0312550 A1 12/2008 Nishtala et al.
2009/0025717 A1 1/2009 Pinel
2009/0048570 A1 2/2009 Jensen
2009/0056003 A1 3/2009 Ivie et al.
2009/0069761 A1 3/2009 Vogel
2009/0069765 A1 3/2009 Wortham
2009/0120179 A1 5/2009 Nylander et al.
2009/0192482 A1 7/2009 Dodge et al.
2009/0199857 A1 8/2009 Peake et al.
2009/0226541 A1 9/2009 Scholz et al.
2009/0234312 A1 9/2009 OToole et al.
2009/0247968 A1 10/2009 Brooks et al.
2009/0251510 A1 10/2009 Noro et al.
2009/0254040 A1 10/2009 Bierman et al.
2009/0259206 A1 10/2009 Kai et al.
2009/0264840 A1 10/2009 Virginio
2009/0270822 A1 10/2009 Medeiros
2009/0281510 A1 11/2009 Fisher
2009/0283982 A1 11/2009 Thomas
2009/0306610 A1 12/2009 Van Den Heuvel et al.
2010/0004612 A1 1/2010 Thevenin
2010/0030189 A1 2/2010 Fleming
2010/0031429 A1 2/2010 Kim et al.
2010/0032789 A1 2/2010 Schoen et al.
2010/0058660 A1 3/2010 Williams
2010/0121289 A1 5/2010 Parks et al.
2010/0158168 A1 6/2010 Murthy et al.
2010/0160882 A1 6/2010 Lowe
2010/0174250 A1 7/2010 Hu et al.
2010/0179493 A1 7/2010 Heagle et al.
2010/0185168 A1 7/2010 Graauw et al.
2010/0198172 A1 8/2010 Wada et al.
2010/0211032 A1 8/2010 Tsai et al.
2010/0234820 A1 9/2010 Tsai et al.
2010/0241104 A1 9/2010 Gilbert
2010/0263113 A1 10/2010 Shelton et al.
2010/0310845 A1 12/2010 Bond et al.
2011/0022011 A1 1/2011 Edward
2011/0028920 A1 2/2011 Johannison
2011/0028922 A1 2/2011 Kay et al.
2011/0034889 A1 2/2011 Smith
2011/0036837 A1 2/2011 Shang
2011/0040267 A1 2/2011 Wada et al.
2011/0040271 A1 2/2011 Rogers et al.
2011/0054426 A1 3/2011 Stewart et al.
2011/0060299 A1 3/2011 Wada et al.
2011/0060300 A1 3/2011 Weig et al.
2011/0077495 A1 3/2011 Gilbert
2011/0077606 A1 3/2011 Wilcox et al.

(56) References Cited

U.S. PATENT DOCUMENTS

| | | | |
|---|---|---|---|
| 2011/0087337 | A1 | 4/2011 | Forsell |
| 2011/0137273 | A1 | 6/2011 | Muellejans et al. |
| 2011/0145993 | A1 | 6/2011 | Rader et al. |
| 2011/0152802 | A1 | 6/2011 | Dicamillo et al. |
| 2011/0152842 | A1 | 6/2011 | Graffam et al. |
| 2011/0164147 | A1 | 7/2011 | Takahashi et al. |
| 2011/0172620 | A1 | 7/2011 | Khambatta |
| 2011/0172625 | A1 | 7/2011 | Wada et al. |
| 2011/0198904 | A1 | 8/2011 | Thomas et al. |
| 2011/0202024 | A1 | 8/2011 | Cozzens |
| 2011/0238023 | A1 | 9/2011 | Slayton |
| 2011/0240648 | A1 | 10/2011 | Tucker |
| 2011/0251572 | A1 | 10/2011 | Nishtala et al. |
| 2011/0265889 | A1 | 11/2011 | Tanaka et al. |
| 2011/0276020 | A1 | 11/2011 | Mitsui |
| 2012/0004079 | A1 | 1/2012 | Hyacinth |
| 2012/0029452 | A1 | 2/2012 | Roedsten |
| 2012/0035577 | A1 | 2/2012 | Tomes et al. |
| 2012/0041400 | A1 | 2/2012 | Christensen |
| 2012/0059328 | A1 | 3/2012 | Dikeman et al. |
| 2012/0066825 | A1 | 3/2012 | Birbara et al. |
| 2012/0103347 | A1 | 5/2012 | Wheaton et al. |
| 2012/0116336 | A1 | 5/2012 | Sharma et al. |
| 2012/0137420 | A1 | 6/2012 | Gordon et al. |
| 2012/0165768 | A1 | 6/2012 | Sekiyama et al. |
| 2012/0165786 | A1 | 6/2012 | Chappa et al. |
| 2012/0209216 | A1 | 8/2012 | Jensen et al. |
| 2012/0209225 | A1 | 8/2012 | Hu et al. |
| 2012/0210503 | A1 | 8/2012 | Anzivino et al. |
| 2012/0215187 | A1 | 8/2012 | Tippet et al. |
| 2012/0233761 | A1 | 9/2012 | Huang |
| 2012/0245541 | A1 | 9/2012 | Suzuki et al. |
| 2012/0245542 | A1 | 9/2012 | Suzuki et al. |
| 2012/0245547 | A1 | 9/2012 | Wilcox et al. |
| 2012/0253303 | A1 | 10/2012 | Suzuki et al. |
| 2012/0271259 | A1 | 10/2012 | Ulert |
| 2012/0296305 | A1 | 11/2012 | Barraza Khaled et al. |
| 2012/0316522 | A1 | 12/2012 | Carter et al. |
| 2012/0330256 | A1 | 12/2012 | Wilcox et al. |
| 2013/0006206 | A1 | 1/2013 | Wada et al. |
| 2013/0019374 | A1 | 1/2013 | Schwartz |
| 2013/0036544 | A1 | 2/2013 | Lee et al. |
| 2013/0045651 | A1 | 2/2013 | Esteves et al. |
| 2013/0046258 | A1 | 2/2013 | Chambers |
| 2013/0053804 | A1 | 2/2013 | Soerensen et al. |
| 2013/0096523 | A1 | 4/2013 | Chang et al. |
| 2013/0110059 | A1 | 5/2013 | Kossow et al. |
| 2013/0138064 | A1 | 5/2013 | Stroebech et al. |
| 2013/0144240 | A1 | 6/2013 | Ellis |
| 2013/0150813 | A1 | 6/2013 | Gordon et al. |
| 2013/0158494 | A1 | 6/2013 | Ong et al. |
| 2013/0165880 | A1 | 6/2013 | Amos et al. |
| 2013/0211385 | A1 | 8/2013 | Lazarus |
| 2013/0218112 | A1 | 8/2013 | Thompson |
| 2013/0245496 | A1 | 9/2013 | Wells et al. |
| 2013/0245586 | A1 | 9/2013 | Jha |
| 2013/0253528 | A1 | 9/2013 | Haffner et al. |
| 2013/0274711 | A1 | 10/2013 | O'Day |
| 2013/0292537 | A1 | 11/2013 | Dirico |
| 2013/0324954 | A1 | 12/2013 | Friedrich |
| 2013/0330501 | A1 | 12/2013 | Aizenberg et al. |
| 2014/0005647 | A1 | 1/2014 | Shuffler et al. |
| 2014/0031774 | A1 | 1/2014 | Bengtson |
| 2014/0039432 | A1 | 2/2014 | Dunbar et al. |
| 2014/0039440 | A1 | 2/2014 | Doescher |
| 2014/0058347 | A1 | 2/2014 | Marquette |
| 2014/0107595 | A1 | 4/2014 | Blott et al. |
| 2014/0107599 | A1 | 4/2014 | Fink et al. |
| 2014/0157499 | A1 | 6/2014 | Suzuki et al. |
| 2014/0171889 | A1 | 6/2014 | Hopman et al. |
| 2014/0182051 | A1 | 7/2014 | Tanimoto et al. |
| 2014/0196189 | A1 | 7/2014 | Lee et al. |
| 2014/0216478 | A1 | 8/2014 | Park et al. |
| 2014/0230831 | A1 | 8/2014 | Zaltsberg et al. |
| 2014/0257231 | A1 | 9/2014 | Wang et al. |
| 2014/0276501 | A1 | 9/2014 | Cisko |
| 2014/0303582 | A1 | 10/2014 | Wright et al. |
| 2014/0316381 | A1 | 10/2014 | Reglin |
| 2014/0325746 | A1 | 11/2014 | Block |
| 2014/0343516 | A1 | 11/2014 | Coulthard et al. |
| 2014/0348139 | A1 | 11/2014 | Gomez Martinez |
| 2014/0352050 | A1 | 12/2014 | Yao et al. |
| 2014/0371628 | A1 | 12/2014 | Desai |
| 2015/0045757 | A1 | 2/2015 | Lee et al. |
| 2015/0047114 | A1 | 2/2015 | Ramirez |
| 2015/0048089 | A1 | 2/2015 | Robertson |
| 2015/0135423 | A1 | 5/2015 | Sharpe et al. |
| 2015/0157300 | A1 | 6/2015 | Ealovega et al. |
| 2015/0209188 | A1 | 7/2015 | Scheremet et al. |
| 2015/0209194 | A1 | 7/2015 | Heyman |
| 2015/0216714 | A1 | 8/2015 | Sasaki et al. |
| 2015/0238687 | A1 | 8/2015 | Novakovic et al. |
| 2015/0267862 | A1 | 9/2015 | Mishler |
| 2015/0290421 | A1 | 10/2015 | Glickman et al. |
| 2015/0290425 | A1 | 10/2015 | Macy et al. |
| 2015/0320583 | A1 | 11/2015 | Harvie |
| 2015/0329255 | A1 | 11/2015 | Rzepecki |
| 2015/0342799 | A1 | 12/2015 | Michiels et al. |
| 2015/0359660 | A1 | 12/2015 | Harvie |
| 2015/0359996 | A1 | 12/2015 | Arora et al. |
| 2015/0366699 | A1 | 12/2015 | Nelson |
| 2015/0374535 | A1 | 12/2015 | Davis et al. |
| 2016/0008193 | A1 | 1/2016 | Schulke |
| 2016/0029998 | A1 | 2/2016 | Brister et al. |
| 2016/0030228 | A1 | 2/2016 | Jones |
| 2016/0038356 | A1 | 2/2016 | Yao et al. |
| 2016/0051395 | A1 | 2/2016 | Ugarte M.d. |
| 2016/0058322 | A1 | 3/2016 | Brister et al. |
| 2016/0060001 | A1 | 3/2016 | Wada et al. |
| 2016/0100976 | A1 | 4/2016 | Conway et al. |
| 2016/0106604 | A1 | 4/2016 | Timm |
| 2016/0113809 | A1 | 4/2016 | Kim |
| 2016/0135792 | A1 | 5/2016 | Cai |
| 2016/0136338 | A1 | 5/2016 | Lee et al. |
| 2016/0183689 | A1 | 6/2016 | Miner |
| 2016/0256022 | A1 | 9/2016 | Le |
| 2016/0270982 | A1 | 9/2016 | Raycheck et al. |
| 2016/0278662 | A1 | 9/2016 | Brister et al. |
| 2016/0327553 | A1 | 11/2016 | Edwards et al. |
| 2016/0357400 | A1 | 12/2016 | Penha et al. |
| 2016/0366699 | A1 | 12/2016 | Zhang et al. |
| 2016/0367226 | A1 | 12/2016 | Newton et al. |
| 2016/0367411 | A1 | 12/2016 | Justiz et al. |
| 2016/0367726 | A1 | 12/2016 | Gratzer |
| 2016/0374848 | A1 | 12/2016 | Sanchez et al. |
| 2017/0007438 | A1 | 1/2017 | Harvie |
| 2017/0014560 | A1 | 1/2017 | Minskoff et al. |
| 2017/0028110 | A1 | 2/2017 | Smith et al. |
| 2017/0042724 | A1 | 2/2017 | Ugarte |
| 2017/0042748 | A1 | 2/2017 | Griffin |
| 2017/0049605 | A1 | 2/2017 | Wisniewski |
| 2017/0100276 | A1 | 4/2017 | Joh |
| 2017/0107312 | A1 | 4/2017 | Hinayama et al. |
| 2017/0128638 | A1 | 5/2017 | Giezendanner et al. |
| 2017/0136209 | A1 | 5/2017 | Burnett et al. |
| 2017/0143534 | A1 | 5/2017 | Sanchez |
| 2017/0165100 | A1 | 6/2017 | Jackson et al. |
| 2017/0165405 | A1 | 6/2017 | Muser et al. |
| 2017/0189225 | A1 | 7/2017 | Voorhees et al. |
| 2017/0202692 | A1 | 7/2017 | Laniado |
| 2017/0216081 | A1 | 8/2017 | Accosta |
| 2017/0238911 | A1 | 8/2017 | Duval |
| 2017/0246026 | A1 | 8/2017 | Laniado |
| 2017/0252014 | A1 | 9/2017 | Siller Gonzalez et al. |
| 2017/0252202 | A9 | 9/2017 | Sanchez et al. |
| 2017/0266031 | A1 | 9/2017 | Sanchez et al. |
| 2017/0266658 | A1 | 9/2017 | Bruno et al. |
| 2017/0281399 | A1 | 10/2017 | Vanmiddendorp et al. |
| 2017/0281419 | A1 | 10/2017 | Pintado |
| 2017/0312116 | A1 | 11/2017 | Laniado |
| 2017/0312405 | A1 | 11/2017 | Newton |
| 2017/0325788 | A1 | 11/2017 | Ealovega et al. |
| 2017/0333244 | A1 | 11/2017 | Laniado |
| 2017/0340489 | A1 | 11/2017 | Yamada |

(56) References Cited

U.S. PATENT DOCUMENTS

2017/0348139 A1 12/2017 Newton et al.
2017/0354532 A1 12/2017 Holt
2017/0354551 A1 12/2017 Gawley et al.
2017/0367873 A1 12/2017 Grannum
2018/0002075 A1 1/2018 Lee
2018/0008451 A1 1/2018 Stroebech
2018/0008804 A1 1/2018 Laniado
2018/0021218 A1* 1/2018 Brosch .................. A61J 1/1487 428/35.2
2018/0028349 A1 2/2018 Newton et al.
2018/0037384 A1 2/2018 Archeny et al.
2018/0049910 A1 2/2018 Newton
2018/0064572 A1 3/2018 Wiltshire
2018/0104131 A1 4/2018 Killian
2018/0127187 A1 5/2018 Sewell
2018/0149635 A1 5/2018 Abir
2018/0169281 A1 6/2018 Russell et al.
2018/0193215 A1 7/2018 Davies et al.
2018/0200101 A1 7/2018 Su
2018/0214297 A1 8/2018 Hughett et al.
2018/0215649 A1 8/2018 Wada et al.
2018/0221216 A1 8/2018 Benz et al.
2018/0228642 A1 8/2018 Davis et al.
2018/0229014 A1 8/2018 Guirguis et al.
2018/0256384 A1 9/2018 Kasirye
2018/0271694 A1 9/2018 Fernandez et al.
2018/0280236 A1 10/2018 Ludin et al.
2018/0317892 A1 11/2018 Catlin
2018/0325748 A1 11/2018 Sharma et al.
2019/0001029 A1 1/2019 Davie et al.
2019/0001030 A1 1/2019 Braga et al.
2019/0021899 A1 1/2019 Vlet
2019/0029869 A1 1/2019 Huchthausen
2019/0038451 A1 2/2019 Harvie
2019/0046102 A1 2/2019 Kushnir et al.
2019/0059938 A1 2/2019 Holsten
2019/0060138 A1 2/2019 Marquez et al.
2019/0091059 A1 3/2019 Gabriel
2019/0100362 A1 4/2019 Meyers et al.
2019/0133126 A1 5/2019 Modak et al.
2019/0133814 A1 5/2019 Tammen et al.
2019/0142624 A1 5/2019 Sanchez et al.
2019/0224036 A1 7/2019 Sanchez et al.
2019/0226189 A1 7/2019 Braxton
2019/0240079 A1 8/2019 Tuli
2019/0247222 A1 8/2019 Ecklund et al.
2019/0247223 A1 8/2019 Brun et al.
2019/0247623 A1 8/2019 Helm et al.
2019/0282391 A1* 9/2019 Johannes ................ A61F 5/443
2019/0314189 A1 10/2019 Acosta
2019/0314190 A1 10/2019 Sanchez et al.
2019/0321587 A1 10/2019 Mcmenamin et al.
2019/0344934 A1 11/2019 Faerber et al.
2019/0365303 A1 12/2019 Bullington et al.
2019/0365307 A1 12/2019 Laing et al.
2019/0365561 A1 12/2019 Newton et al.
2019/0374373 A1 12/2019 Joh
2020/0008985 A1 1/2020 Nguyen et al.
2020/0016012 A1 1/2020 Dutkiewicz
2020/0030595 A1 1/2020 Boukidjian et al.
2020/0040561 A1 2/2020 Sugawara
2020/0046544 A1 2/2020 Godinez et al.
2020/0055638 A1 2/2020 Lau et al.
2020/0070392 A1 3/2020 Huber et al.
2020/0085609 A1 3/2020 Schelch et al.
2020/0085610 A1 3/2020 Cohn et al.
2020/0086090 A1 3/2020 Von Weymarn-schärli et al.
2020/0107518 A1 4/2020 Hiroshima et al.
2020/0129322 A1 4/2020 Leuckel
2020/0171217 A9 6/2020 Braga et al.
2020/0179177 A1 6/2020 Erdem et al.
2020/0187918 A1 6/2020 Wiygul
2020/0206015 A1 7/2020 Langer
2020/0206039 A1 7/2020 Mclain
2020/0214910 A1 7/2020 Varona et al.
2020/0216898 A1 7/2020 Hubbell
2020/0216989 A1 7/2020 Kinugasa et al.
2020/0229964 A1 7/2020 Staali et al.
2020/0231343 A1 7/2020 Freedman et al.
2020/0232841 A1 7/2020 Satish et al.
2020/0246172 A1 8/2020 Ho
2020/0246203 A1 8/2020 Tulk et al.
2020/0255189 A1 8/2020 Liu
2020/0261280 A1 8/2020 Heyman
2020/0276046 A1 9/2020 Staali et al.
2020/0306075 A1 10/2020 Newton et al.
2020/0315837 A1 10/2020 Radl et al.
2020/0315838 A1 10/2020 Eckert
2020/0315872 A1 10/2020 Viens et al.
2020/0315874 A1 10/2020 Viens et al.
2020/0331672 A1 10/2020 Bertram et al.
2020/0345332 A1 11/2020 Duval
2020/0352774 A1 11/2020 Rabinowitz et al.
2020/0353135 A1 11/2020 Gregory et al.
2020/0367677 A1 11/2020 Silsby et al.
2020/0369444 A1 11/2020 Silsby et al.
2020/0375781 A1 12/2020 Staali et al.
2020/0375810 A1 12/2020 Carlin et al.
2020/0384242 A1 12/2020 Havard et al.
2020/0385179 A1 12/2020 Mccourt
2020/0390591 A1 12/2020 Glithero et al.
2020/0390592 A1 12/2020 Merrill
2020/0398024 A1 12/2020 Fletter et al.
2020/0405521 A1 12/2020 Glasroe
2020/0405523 A1 12/2020 Obst et al.
2021/0007910 A1 1/2021 Furukawa
2021/0008771 A1 1/2021 Huber et al.
2021/0009323 A1 1/2021 Markarian et al.
2021/0020072 A1 1/2021 Moehring et al.
2021/0023279 A1 1/2021 Radl et al.
2021/0059853 A1 3/2021 Davis et al.
2021/0061523 A1 3/2021 Bytheway
2021/0069005 A1 3/2021 Sanchez et al.
2021/0069008 A1 3/2021 Blabas et al.
2021/0069009 A1 3/2021 Im
2021/0069030 A1 3/2021 Nishikawa et al.
2021/0077993 A1 3/2021 Nazareth et al.
2021/0113749 A1 4/2021 Radl et al.
2021/0121318 A1* 4/2021 Pinlac ..................... A61F 5/441
2021/0137724 A1 5/2021 Ecklund et al.
2021/0138190 A1 5/2021 Erbey et al.
2021/0154055 A1 5/2021 Villarreal
2021/0170079 A1 6/2021 Radl et al.
2021/0178390 A1 6/2021 Oueslati et al.
2021/0186742 A1 6/2021 Newton et al.
2021/0186744 A1 6/2021 Spector
2021/0206144 A1 7/2021 Ewell
2021/0211568 A1 7/2021 Zhou et al.
2021/0212865 A1 7/2021 Wallajapet et al.
2021/0220162 A1 7/2021 Jamison
2021/0220163 A1 7/2021 Mayrand
2021/0228400 A1 7/2021 Glithero
2021/0228401 A1* 7/2021 Becker .................... A61F 5/453
2021/0228795 A1 7/2021 Hughett et al.
2021/0229877 A1 7/2021 Ragias et al.
2021/0236323 A1 8/2021 Austermann et al.
2021/0236324 A1 8/2021 Sweeney
2021/0251814 A1 8/2021 Jönegren et al.
2021/0267787 A1 9/2021 Nazemi
2021/0275343 A1 9/2021 Sanchez et al.
2021/0275344 A1 9/2021 Wing
2021/0290454 A1 9/2021 Yamada
2021/0290464 A1 9/2021 Furuta
2021/0315726 A1 10/2021 Lin
2021/0315727 A1 10/2021 Jiang
2021/0353449 A1 11/2021 Sharma et al.
2021/0353450 A1* 11/2021 Sharma ................. A61F 5/4408
2021/0361469 A1* 11/2021 Liu ....................... A61F 5/4401
2021/0369495 A1 12/2021 Cheng et al.
2021/0386925 A1 12/2021 Hartwell et al.
2021/0393433 A1 12/2021 Godinez et al.
2022/0015958 A1 1/2022 Ito
2022/0023091 A1 1/2022 Ecklund et al.
2022/0026546 A1 1/2022 Aono et al.

(56) References Cited

U.S. PATENT DOCUMENTS

| | | | |
|---|---|---|---|
| 2022/0031290 | A1 | 2/2022 | Weed |
| 2022/0031523 | A1 | 2/2022 | Pierpoint |
| 2022/0039995 | A1 | 2/2022 | Johannes et al. |
| 2022/0047410 | A1 | 2/2022 | Walthall |
| 2022/0062025 | A1 | 3/2022 | Shields et al. |
| 2022/0062027 | A1 | 3/2022 | Mitchell et al. |
| 2022/0062028 | A1 | 3/2022 | Mitchell et al. |
| 2022/0062029 | A1 | 3/2022 | Johannes et al. |
| 2022/0066825 | A1 | 3/2022 | Saraf et al. |
| 2022/0071811 | A1 | 3/2022 | Cheng et al. |
| 2022/0071826 | A1 | 3/2022 | Kulkarni et al. |
| 2022/0104965 | A1 | 4/2022 | Vaninetti et al. |
| 2022/0104976 | A1 | 4/2022 | Hoeger et al. |
| 2022/0104981 | A1 | 4/2022 | Jones |
| 2022/0117773 | A1 | 4/2022 | Davis et al. |
| 2022/0117774 | A1 | 4/2022 | Meyer et al. |
| 2022/0117775 | A1 | 4/2022 | Jones et al. |
| 2022/0118165 | A1 | 4/2022 | Knapp et al. |
| 2022/0133524 | A1 | 5/2022 | Davis |
| 2022/0151817 | A1 | 5/2022 | Mann |
| 2022/0160949 | A1 | 5/2022 | Simiele et al. |
| 2022/0168159 | A1 | 6/2022 | Triado et al. |
| 2022/0193312 | A1 | 6/2022 | Lee et al. |
| 2022/0211536 | A1 | 7/2022 | Johannes et al. |
| 2022/0218510 | A1 | 7/2022 | Metzger et al. |
| 2022/0229053 | A1* | 7/2022 | Levin ............... G01N 33/54373 |
| 2022/0241106 | A1 | 8/2022 | Johannes et al. |
| 2022/0241115 | A1 | 8/2022 | Lang et al. |
| 2022/0247407 | A1 | 8/2022 | Yamamoto et al. |
| 2022/0248836 | A1 | 8/2022 | Cagle et al. |
| 2022/0257407 | A1 | 8/2022 | Johannes et al. |
| 2022/0265460 | A1 | 8/2022 | Coker |
| 2022/0265462 | A1 | 8/2022 | Alder et al. |
| 2022/0270711 | A1 | 8/2022 | Feala et al. |
| 2022/0273482 | A1 | 9/2022 | Johannes et al. |
| 2022/0280357 | A1 | 9/2022 | Jagannathan et al. |
| 2022/0280710 | A1 | 9/2022 | Agrawal et al. |
| 2022/0287689 | A1 | 9/2022 | Johannes |
| 2022/0287691 | A1 | 9/2022 | Wormser et al. |
| 2022/0287867 | A1 | 9/2022 | Jones et al. |
| 2022/0287868 | A1 | 9/2022 | Garvey et al. |
| 2022/0296408 | A1 | 9/2022 | Evans et al. |
| 2022/0305191 | A1 | 9/2022 | Joseph et al. |
| 2022/0313222 | A1 | 10/2022 | Austermann et al. |
| 2022/0313474 | A1 | 10/2022 | Kriscovich et al. |
| 2022/0331170 | A1 | 10/2022 | Erdem et al. |
| 2022/0339023 | A1 | 10/2022 | Davis et al. |
| 2022/0339024 | A1 | 10/2022 | Johannes et al. |
| 2022/0354685 | A1 | 11/2022 | Davis et al. |
| 2022/0362049 | A1 | 11/2022 | Austermann et al. |
| 2022/0370231 | A1 | 11/2022 | Wang et al. |
| 2022/0370234 | A1 | 11/2022 | Hughett et al. |
| 2022/0370235 | A1 | 11/2022 | Johannes et al. |
| 2022/0370237 | A1 | 11/2022 | Parmar et al. |
| 2022/0387001 | A1 | 12/2022 | Askenazi et al. |
| 2022/0387693 | A1 | 12/2022 | Bannwart et al. |
| 2022/0395390 | A1 | 12/2022 | Brooks |
| 2022/0395391 | A1 | 12/2022 | Saunders et al. |
| 2022/0401252 | A1 | 12/2022 | Warren |
| 2022/0409419 | A1 | 12/2022 | Garvey et al. |
| 2022/0409422 | A1 | 12/2022 | Schneider et al. |
| 2023/0018845 | A1 | 1/2023 | Lee |
| 2023/0020563 | A1* | 1/2023 | Sharma ................... A61F 5/443 |
| 2023/0031640 | A1 | 2/2023 | Hughett et al. |
| 2023/0037159 | A1 | 2/2023 | Brennan et al. |
| 2023/0049924 | A1 | 2/2023 | Johannes et al. |
| 2023/0052238 | A1 | 2/2023 | Oluwasogo |
| 2023/0062994 | A1 | 3/2023 | Ecklund et al. |
| 2023/0070347 | A1 | 3/2023 | Watson et al. |
| 2023/0073708 | A1 | 3/2023 | Xu et al. |
| 2023/0089032 | A1 | 3/2023 | Hughett et al. |
| 2023/0091118 | A1 | 3/2023 | Watson |
| 2023/0099821 | A1 | 3/2023 | Radl et al. |
| 2023/0099991 | A1 | 3/2023 | Bianchi et al. |
| 2023/0105001 | A1 | 4/2023 | Whittome et al. |
| 2023/0110577 | A1 | 4/2023 | Choi |
| 2023/0138269 | A1 | 5/2023 | Abdelal et al. |
| 2023/0145365 | A1 | 5/2023 | Martin et al. |
| 2023/0155253 | A1 | 5/2023 | Mn et al. |
| 2023/0190511 | A1 | 6/2023 | Sharma et al. |
| 2023/0210504 | A1 | 7/2023 | Kuroda et al. |
| 2023/0210685 | A1 | 7/2023 | Fallows et al. |
| 2023/0218426 | A1 | 7/2023 | Hughett |
| 2023/0240884 | A1 | 8/2023 | Davis et al. |
| 2023/0248562 | A1 | 8/2023 | Sanchez et al. |
| 2023/0248564 | A1 | 8/2023 | Mann et al. |
| 2023/0255812 | A1 | 8/2023 | Sanchez et al. |
| 2023/0255813 | A1 | 8/2023 | Sanchez et al. |
| 2023/0255815 | A1 | 8/2023 | Newton |
| 2023/0263650 | A1 | 8/2023 | Sanchez et al. |
| 2023/0263655 | A1 | 8/2023 | Johannes et al. |
| 2023/0277360 | A1 | 9/2023 | Lambert et al. |
| 2023/0277362 | A1 | 9/2023 | Davis et al. |
| 2023/0285178 | A1 | 9/2023 | Sanchez et al. |
| 2023/0293339 | A1 | 9/2023 | James |
| 2023/0301846 | A1 | 9/2023 | Greenwood |
| 2023/0355423 | A1 | 11/2023 | Stevenson et al. |
| 2023/0389900 | A1 | 12/2023 | Xie et al. |
| 2023/0404791 | A1 | 12/2023 | Ecklund et al. |
| 2024/0008444 | A1 | 1/2024 | Su et al. |
| 2024/0009023 | A1 | 1/2024 | Johannes et al. |
| 2024/0024170 | A1 | 1/2024 | Scott |
| 2024/0033148 | A1 | 2/2024 | Gordon et al. |
| 2024/0041638 | A1 | 2/2024 | Johannes et al. |
| 2024/0058157 | A1 | 2/2024 | Davis |
| 2024/0058160 | A1 | 2/2024 | Young Joyner et al. |
| 2024/0058161 | A1 | 2/2024 | Ulreich et al. |
| 2024/0058520 | A1 | 2/2024 | Yin et al. |
| 2024/0065881 | A1 | 2/2024 | Kuroda et al. |
| 2024/0082044 | A1 | 3/2024 | Nguyen et al. |
| 2024/0099874 | A1 | 3/2024 | Sanchez et al. |
| 2024/0108268 | A1 | 4/2024 | Woodard et al. |
| 2024/0110318 | A1 | 4/2024 | Bendt et al. |
| 2024/0122773 | A1 | 4/2024 | Nguyen et al. |
| 2024/0123134 | A1 | 4/2024 | Kharkar et al. |
| 2024/0130885 | A1 | 4/2024 | Young Joyner et al. |
| 2024/0148539 | A1 | 5/2024 | Austermann et al. |
| 2024/0156633 | A1 | 5/2024 | Fallows et al. |
| 2024/0164935 | A1 | 5/2024 | Newton |
| 2024/0180737 | A1 | 6/2024 | Newton |
| 2024/0252343 | A1 | 8/2024 | Voda |
| 2024/0261131 | A1 | 8/2024 | Garvey et al. |
| 2024/0268986 | A1 | 8/2024 | Barnes et al. |
| 2024/0268989 | A1 | 8/2024 | Martin et al. |
| 2024/0268991 | A1 | 8/2024 | Davis |
| 2024/0269027 | A1 | 8/2024 | Tourchak et al. |
| 2024/0285425 | A1 | 8/2024 | Donohoe et al. |
| 2024/0325190 | A1 | 10/2024 | Minchew et al. |
| 2024/0335599 | A1 | 10/2024 | Cheng et al. |
| 2024/0341998 | A1 | 10/2024 | Julian et al. |
| 2024/0358539 | A1 | 10/2024 | Gallup |
| 2024/0358542 | A1 | 10/2024 | Richardson et al. |
| 2024/0374414 | A1 | 11/2024 | Richardson et al. |
| 2025/0009552 | A1 | 1/2025 | Blabas et al. |
| 2025/0073055 | A1 | 3/2025 | Ecklund et al. |
| 2025/0107920 | A1 | 4/2025 | Fallows et al. |
| 2025/0107921 | A1 | 4/2025 | Sanchez et al. |
| 2025/0367358 | A1 | 12/2025 | Smith et al. |
| 2026/0020972 | A1 | 1/2026 | Godinez et al. |

FOREIGN PATENT DOCUMENTS

| | | | |
|---|---|---|---|
| AU | 2022349367 | A1 | 4/2024 |
| CA | 2165286 | C | 9/1999 |
| CA | 2335223 | A1 | 1/2000 |
| CA | 2354132 | A1 | 6/2000 |
| CA | 2359091 | C | 9/2003 |
| CA | 2488867 | C | 8/2007 |
| CA | 3031934 | A1 | 2/2018 |
| CA | 3050918 | A1 | 8/2018 |
| CA | 3098571 | A1 | 11/2019 |
| CA | 3144181 | A1 | 1/2021 |
| CA | 3188651 | A1 | 7/2023 |
| CN | 2269203 | Y | 12/1997 |

(56) References Cited

FOREIGN PATENT DOCUMENTS

| | | | | |
|---|---|---|---|---|
| CN | 1332620 | A | 1/2002 | |
| CN | 1434693 | A | 8/2003 | |
| CN | 2569779 | Y | 9/2003 | |
| CN | 1533755 | A | 10/2004 | |
| CN | 1579348 | A | 2/2005 | |
| CN | 1602825 | A | 4/2005 | |
| CN | 1638708 | A | 7/2005 | |
| CN | 1720888 | A | 1/2006 | |
| CN | 2936204 | Y | 8/2007 | |
| CN | 101262836 | A | 9/2008 | |
| CN | 101522148 | A | 9/2009 | |
| CN | 102159159 | A | 8/2011 | |
| CN | 202184840 | U | 4/2012 | |
| CN | 102481441 | A | 5/2012 | |
| CN | 202463712 | U | 10/2012 | |
| CN | 202950810 | U | 5/2013 | |
| CN | 103533968 | A | 1/2014 | |
| CN | 103717180 | A | 4/2014 | |
| CN | 204562697 | U | 8/2015 | |
| CN | 105411783 | A | 3/2016 | |
| CN | 105451607 | A | 3/2016 | |
| CN | 105451693 | A | 3/2016 | |
| CN | 105534632 | A | 5/2016 | |
| CN | 105616072 | A | 6/2016 | |
| CN | 106132360 | A | 11/2016 | |
| CN | 106137631 | A | 11/2016 | |
| CN | 205849719 | U | 1/2017 | |
| CN | 205924282 | U | 2/2017 | |
| CN | 106726089 | A | 5/2017 | |
| CN | 107847384 | A | 3/2018 | |
| CN | 107920912 | A | 4/2018 | |
| CN | 108420590 | A | 8/2018 | |
| CN | 207785556 | U | 8/2018 | |
| CN | 110171118 | A | 8/2019 | |
| CN | 209285902 | U | 8/2019 | |
| CN | 110381883 | A | 10/2019 | |
| CN | 111465375 | A | 7/2020 | |
| CN | 211198839 | U | 8/2020 | |
| CN | 111991136 | A | 11/2020 | |
| CN | 112022488 | A | 12/2020 | |
| CN | 212234893 | U | 12/2020 | |
| CN | 212466312 | U | 2/2021 | |
| CN | 112566550 | A | 3/2021 | |
| CN | 112603184 | A | 4/2021 | |
| CN | 213490035 | U | 6/2021 | |
| CN | 114007493 | A | 2/2022 | |
| CN | 114375187 | A | 4/2022 | |
| CN | 116096332 | A * | 5/2023 | ........... A61F 5/4404 |
| DE | 79818 | C | 10/1893 | |
| DE | 1516466 | A1 | 6/1969 | |
| DE | 2721330 | A1 | 11/1977 | |
| DE | 2742298 | A1 | 3/1978 | |
| DE | 3104356 | A1 | 9/1982 | |
| DE | 9407554.9 | U1 | 5/1995 | |
| DE | 4443710 | A1 | 6/1995 | |
| DE | 4416094 | A1 | 11/1995 | |
| DE | 4236097 | C2 | 10/1996 | |
| DE | 19619597 | A1 | 11/1997 | |
| DE | 202005013173 | U1 | 6/2006 | |
| DE | 102005037762 | B3 | 9/2006 | |
| DE | 202006018506 | U1 | 3/2007 | |
| DE | 102011103783 | A1 | 12/2012 | |
| DE | 102012112818 | A1 | 6/2014 | |
| DE | 202015104597 | U1 | 7/2016 | |
| DE | 102018118570 | A1 | 2/2020 | |
| DE | 102020121462 | B3 | 1/2022 | |
| DK | 9600118 | | 11/1996 | |
| EP | 0032138 | A2 | 7/1981 | |
| EP | 0066070 | B1 | 12/1982 | |
| EP | 0068712 | A1 | 1/1983 | |
| EP | 0140470 | A1 | 5/1985 | |
| EP | 0220962 | A1 | 5/1987 | |
| EP | 0140471 | B1 | 5/1988 | |
| EP | 0274753 | A2 | 7/1988 | |
| EP | 0119143 | B1 | 11/1988 | |
| EP | 0483592 | A1 | 5/1992 | |
| EP | 0483730 | A1 | 5/1992 | |
| EP | 0610638 | A1 | 8/1994 | |
| EP | 0613355 | A1 | 9/1994 | |
| EP | 0711536 | A1 | 5/1996 | |
| EP | 0613355 | B1 | 1/1997 | |
| EP | 0680296 | B1 | 5/1997 | |
| EP | 0 787 472 | A1 * | 6/1997 | |
| EP | 0945231 | A2 | 9/1999 | |
| EP | 0966936 | A1 | 12/1999 | |
| EP | 0987293 | A1 | 3/2000 | |
| EP | 1063953 | A1 | 1/2001 | |
| EP | 0653928 | B1 | 10/2002 | |
| EP | 1332738 | A1 | 8/2003 | |
| EP | 1382318 | A1 | 1/2004 | |
| EP | 1089684 | B1 | 10/2004 | |
| EP | 1616542 | A1 | 1/2006 | |
| EP | 1382318 | B1 | 5/2006 | |
| EP | 1063953 | B1 | 1/2007 | |
| EP | 1658831 | B1 | 1/2008 | |
| EP | 1872752 | A1 | 1/2008 | |
| EP | 2180907 | A1 | 5/2010 | |
| EP | 2380532 | A1 | 10/2011 | |
| EP | 2389908 | A1 | 11/2011 | |
| EP | 2601916 | A1 | 6/2013 | |
| EP | 2676643 | A1 | 12/2013 | |
| EP | 2470251 | B1 | 12/2014 | |
| EP | 2997950 | A2 | 3/2016 | |
| EP | 2879534 | B1 | 3/2017 | |
| EP | 3424471 | A1 | 1/2019 | |
| EP | 3169292 | B1 | 11/2019 | |
| EP | 3753492 | A1 | 12/2020 | |
| EP | 3777801 | A1 | 2/2021 | |
| EP | 3788992 | A1 | 3/2021 | |
| EP | 3576689 | B1 | 3/2022 | |
| EP | 3752110 | B1 | 3/2022 | |
| EP | 3787570 | B1 | 3/2022 | |
| EP | 4025163 | A1 | 7/2022 | |
| EP | 3463180 | B1 | 3/2023 | |
| EP | 3749230 | B1 | 3/2023 | |
| EP | 3569205 | B1 | 6/2023 | |
| EP | 4192402 | A1 | 6/2023 | |
| EP | 4218702 | A1 | 8/2023 | |
| EP | 3624742 | B1 | 1/2024 | |
| EP | 4382082 | A2 | 6/2024 | |
| EP | 4445881 | A2 | 10/2024 | |
| EP | 4464288 | A2 | 11/2024 | |
| EP | 4215134 | B1 | 1/2025 | |
| EP | 4494611 | A2 | 1/2025 | |
| EP | 4527361 | A2 | 3/2025 | |
| FR | 2294812 | A1 | 7/1976 | |
| FR | 2826704 | A1 | 1/2003 | |
| GB | 871820 | A | 7/1961 | |
| GB | 0873045 | A | 7/1961 | |
| GB | 996370 | A | 6/1965 | |
| GB | 1011517 | A | 12/1965 | |
| GB | 1467144 | A | 3/1977 | |
| GB | 2106395 | A | 4/1983 | |
| GB | 2106784 | A | 4/1983 | |
| GB | 2148126 | A | 5/1985 | |
| GB | 2171315 | A | 8/1986 | |
| GB | 2181953 | A | 5/1987 | |
| GB | 2148126 | B | 7/1987 | |
| GB | 2191095 | A | 12/1987 | |
| GB | 2199750 | A | 7/1988 | |
| GB | 2260907 | A | 5/1993 | |
| GB | 2415386 | A | 12/2005 | |
| GB | 2462267 | A | 2/2010 | |
| GB | 2469496 | A | 10/2010 | |
| GB | 2490327 | A | 10/2012 | |
| GB | 2507318 | A | 4/2014 | |
| GB | 2612752 | A | 5/2023 | |
| IT | 201800009129 | A1 | 4/2020 | |
| JP | S498638 | U | 1/1974 | |
| JP | S5410596 | A | 1/1979 | |
| JP | S5410596 | Y2 | 5/1979 | |
| JP | S54155729 | U | 10/1979 | |
| JP | S55155618 | A | 12/1980 | |
| JP | S56152629 | U | 11/1981 | |

(56) References Cited

FOREIGN PATENT DOCUMENTS

| | | | |
|---|---|---|---|
| JP | S57142534 | U | 9/1982 |
| JP | S5888596 | U | 6/1983 |
| JP | S58130026 | A | 8/1983 |
| JP | S58188016 | U | 12/1983 |
| JP | S59118161 | A | 7/1984 |
| JP | S61502100 | A | 9/1986 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H0515928 | U | 3/1993 |
| JP | H05123349 | A | 5/1993 |
| JP | H05123350 | A | 5/1993 |
| JP | H0625981 | U | 4/1994 |
| JP | H0626264 | U | 4/1994 |
| JP | 3087938 | B2 | 10/1995 |
| JP | H085630 | A | 1/1996 |
| JP | H08117271 | A | 5/1996 |
| JP | H08510924 | A | 11/1996 |
| JP | 2686634 | B2 | 12/1997 |
| JP | H1038669 | A | 2/1998 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000152953 | A | 6/2000 |
| JP | 2000185068 | A | 7/2000 |
| JP | 2000225139 | A | 8/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2002502667 | A | 1/2002 |
| JP | 2002102285 | A | 4/2002 |
| JP | 2003038563 | A | 2/2003 |
| JP | 2003505152 | A | 2/2003 |
| JP | 2003126242 | A | 5/2003 |
| JP | 2003180722 | A | 7/2003 |
| JP | 2003227004 | A | 8/2003 |
| JP | 2003528691 | A | 9/2003 |
| JP | 2004057578 | A | 2/2004 |
| JP | 2004130056 | A | 4/2004 |
| JP | 2004267400 | A | 9/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 2005518901 | A | 6/2005 |
| JP | 3749097 | B2 | 12/2005 |
| JP | 2006026108 | A | 2/2006 |
| JP | 3123547 | B2 | 6/2006 |
| JP | 2006136491 | A | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 2007259898 | A | 10/2007 |
| JP | 4039641 | B2 | 11/2007 |
| JP | 2008005975 | A | 1/2008 |
| JP | 2008278928 | A | 11/2008 |
| JP | 2009500111 | A | 1/2009 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010058795 | A | 3/2010 |
| JP | 2010081981 | A | 4/2010 |
| JP | 2010166954 | A | 8/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011522584 | A | 8/2011 |
| JP | 2011202664 | A | 10/2011 |
| JP | 2011218130 | A | 11/2011 |
| JP | 2011224070 | A | 11/2011 |
| JP | 3175719 | U | 4/2012 |
| JP | 2012522014 | A | 9/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 2015513678 | A | 5/2015 |
| JP | 3198994 | B2 | 7/2015 |
| JP | 2015221390 | A | 12/2015 |
| JP | 2016521191 | A | 7/2016 |
| JP | 2017014698 | A | 1/2017 |
| JP | 3208707 | U | 2/2017 |
| JP | 3209321 | U | 3/2017 |
| JP | 2017070400 | A | 4/2017 |
| JP | 2017512603 | A | 5/2017 |
| JP | 2017127596 | A | 7/2017 |
| JP | 2017201272 | A | 11/2017 |
| JP | 2019010375 | A | 1/2019 |
| JP | 2019076342 | A | 5/2019 |
| JP | 2019525811 | A | 9/2019 |
| JP | 2019170942 | A | 10/2019 |
| JP | 2019533492 | A | 11/2019 |
| JP | 2020510464 | A | 4/2020 |
| JP | 2020520775 | A | 7/2020 |
| JP | 2020124425 | A | 8/2020 |
| JP | 2021007472 | A | 1/2021 |
| JP | 2021041145 | A | 3/2021 |
| JP | 2021074491 | A | 5/2021 |
| JP | 2021120686 | A | 8/2021 |
| JP | 2021520952 | A | 8/2021 |
| JP | 2021522009 | A | 8/2021 |
| JP | 2021522013 | A | 8/2021 |
| JP | 2021522019 | A | 8/2021 |
| JP | 7129493 | B2 | 8/2022 |
| JP | 2022536986 | A | 8/2022 |
| JP | 2022554252 | A | 12/2022 |
| JP | 2023532132 | A | 7/2023 |
| KR | 200290061 | Y1 | 9/2002 |
| KR | 20030047451 | A | 6/2003 |
| KR | 20080005516 | A | 1/2008 |
| KR | 20090072069 | A | 7/2009 |
| KR | 20090104426 | A | 10/2009 |
| KR | 20090110359 | A | 10/2009 |
| KR | 20100137210 | A | 12/2010 |
| KR | 101035745 | B1 | 5/2011 |
| KR | 20120005922 | A | 1/2012 |
| KR | 20140039485 | A | 4/2014 |
| KR | 101432639 | B1 | 8/2014 |
| KR | 20180022173 | A | 3/2018 |
| KR | 20180106659 | A | 10/2018 |
| KR | 20180108774 | A | 10/2018 |
| KR | 101976679 | B1 | 5/2019 |
| KR | 101998130 | B1 | 7/2019 |
| KR | 20230034343 | A | 3/2023 |
| PT | 2068717 | E | 6/2013 |
| SE | 505542 | C2 | 9/1997 |
| TW | 408207 | B | 10/2000 |
| TW | 202123903 | A | 7/2021 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9303690 | A1 | 3/1993 |
| WO | 9307839 | A1 | 4/1993 |
| WO | 9309736 | A2 | 5/1993 |
| WO | 9309736 | A3 | 6/1993 |

(56) References Cited

FOREIGN PATENT DOCUMENTS

| | | | |
|---|---|---|---|
| WO | 9416914 | A1 | 8/1994 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03015671 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005003725 | A2 | 1/2005 |
| WO | 2005051252 | A1 | 6/2005 |
| WO | 2005060558 | A2 | 7/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012020506 | A1 | 2/2012 |
| WO | 2012065274 | A1 | 5/2012 |
| WO | 2012097462 | A1 | 7/2012 |
| WO | 2012098796 | A1 | 7/2012 |
| WO | 2012101288 | A1 | 8/2012 |
| WO | 2012175916 | A1 | 12/2012 |
| WO | 2013018435 | A1 | 2/2013 |
| WO | 2013033429 | A1 | 3/2013 |
| WO | 2013055434 | A1 | 4/2013 |
| WO | 2013082397 | A1 | 6/2013 |
| WO | 2013103291 | A2 | 7/2013 |
| WO | 2013131109 | A1 | 9/2013 |
| WO | 2013167478 | A1 | 11/2013 |
| WO | 2013177716 | A1 | 12/2013 |
| WO | 2014041534 | A1 | 3/2014 |
| WO | 2014046420 | A1 | 3/2014 |
| WO | 2014118518 | A1 | 8/2014 |
| WO | 2014160852 | A1 | 10/2014 |
| WO | 2015023599 | A1 | 2/2015 |
| WO | 2015052348 | A1 | 4/2015 |
| WO | 2015068384 | A1 | 5/2015 |
| WO | 2015169403 | A1 | 11/2015 |
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017100511 | A1 | 6/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018200721 | A1 | 11/2018 |
| WO | 2018235026 | A1 | 12/2018 |
| WO | 2018235065 | A1 | 12/2018 |
| WO | 2019004404 | A1 | 1/2019 |
| WO | 2019038732 | A1 | 2/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020033752 | A1 | 2/2020 |

(56) References Cited

FOREIGN PATENT DOCUMENTS

| | | | |
|---|---|---|---|
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016056 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022029662 | A1 | 2/2022 |
| WO | 2022031943 | A1 | 2/2022 |
| WO | 2022035745 | A1 | 2/2022 |
| WO | 2022051220 | A1 | 3/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150290 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022173803 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2022251184 | A1 | 12/2022 |
| WO | 2022251425 | A1 | 12/2022 |
| WO | 2022271783 | A1 | 12/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023018656 | A1 | 2/2023 |
| WO | 2023018657 | A1 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049156 | A1 | 3/2023 |
| WO | 2023049175 | A1 | 3/2023 |
| WO | 2023086394 | A1 | 5/2023 |
| WO | 2023146529 | A1 | 8/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023163725 | A1 | 8/2023 |
| WO | 2023191764 | A1 | 10/2023 |
| WO | 2023244238 | A1 | 12/2023 |
| WO | 2024043871 | A1 | 2/2024 |
| WO | 2024058788 | A1 | 3/2024 |
| WO | 2024253655 | A1 | 12/2024 |
| WO | 2025034959 | A1 | 2/2025 |
| WO | 2025038087 | A1 | 2/2025 |
| WO | 2025038088 | A1 | 2/2025 |
| WO | 2025048789 | A1 | 3/2025 |
| WO | 2025071622 | A1 | 4/2025 |
| WO | 2025179267 | A1 | 8/2025 |
| WO | 2026035497 | A1 | 2/2026 |

OTHER PUBLICATIONS

Advisory Action for U.S. Appl. No. 14/722,613 mailed Mar. 4, 2019.

Advisory Action for U.S. Appl. No. 14/952,591 mailed Jun. 1, 2018.

Advisory Action for U.S. Appl. No. 15/238,427 mailed Apr. 10, 2019.

Advisory Action for U.S. Appl. No. 16/452,258 mailed Oct. 26, 2022.

Advisory Action for U.S. Appl. No. 16/478,180 mailed Sep. 21, 2022.

Advisory Action for U.S. Appl. No. 16/899,956 mailed Jul. 9, 2021.

Advisory Action for U.S. Appl. No. 16/904,868 mailed Jul. 2, 2021.

Advisory Action for U.S. Appl. No. 16/904,868 mailed Jun. 15, 2022.

Advisory Action for U.S. Appl. No. 16/905,400 mailed Feb. 16, 2022.

Advisory Action for U.S. Appl. No. 16/905,400 mailed Jun. 9, 2021.

Advisory Action for U.S. Appl. No. 17/662,700 mailed Jan. 30, 2023.

Corrected International Search Report and Written Opinion for International Application No. PCT/US2017/043025 mailed Jan. 11, 2018.

Corrected Notice of Allowability for U.S. Appl. No. 15/221,106 mailed Jul. 2, 2019.

Corrected Notice of Allowability for U.S. Appl. No. 15/612,325 mailed Mar. 17, 2021.

Corrected Notice of Allowability for U.S. Appl. No. 17/330,657 mailed Dec. 9, 2021.

Final Office Action for U.S. Appl. No. 14/722,613 mailed on Nov. 29, 2018.

(56) References Cited

OTHER PUBLICATIONS

Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 17/662,700 mailed Sep. 30, 2022.
Final Office Action for U.S. Appl. No. 29/624,661 mailed Feb. 18, 2020.
International Search Report and Written Opinion from International Application No. PCT/IB2021/057173 mailed Nov. 5, 2021.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.

(56) References Cited

OTHER PUBLICATIONS

International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/042719 mailed Dec. 5, 2022.
International Search Report and Written Opinion from International Application No. PCT/US2022/044107 mailed Dec. 23, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 29/624,661 mailed Aug. 4, 2021.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.

(56) References Cited

OTHER PUBLICATIONS

Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Dec. 20, 2022.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/051,550 mailed Dec. 15, 2022.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 17/451,345 mailed Dec. 7, 2022.
Non-Final Office Action for U.S. Appl. No. 17/662,700 mailed Jul. 22, 2022.
Non-Final Office Action for U.S. Appl. No. 29/624,661 mailed Jul. 18, 2019.
Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/461,036 mailed Oct. 6, 2022.
Notice of Allowance for U.S. Appl. No. 17/663,046 mailed Jan. 30, 2023.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
Restriction Requirement for U.S. Appl. No. 17/446,256 mailed Jan. 23, 2023.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/384,196, filed Dec. 19, 2016.
U.S. Appl. No. 15/611,587, filed Jun. 1, 2017.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.

(56) References Cited

OTHER PUBLICATIONS

U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036, filed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 17/999,648, filed Nov. 22, 2022.
U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.

(56) References Cited

OTHER PUBLICATIONS

U.S. Appl. No. 63/159,186, filed Mar. 10, 2021.
U.S. Appl. No. 63/159,210, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims To Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/US/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinx!, 7 pages.
"Urine Bag Cover-Catheter Bag Cover 2000 ml Volume-Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota , et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.

(56) References Cited

OTHER PUBLICATIONS

Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Macaulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
Purewick , "Incontinence Relief for Women", Presentation, Sep. 23, 2015, 7 pages.
Pytlik , "Super Absorbent Polymers", University of Buffallo.
Sachtman , "New Relief for Pilots? It Depends", Wired, 2008, 2 pages.
Tsipenyuk , et al., "Use of biomimetic hexagonal surface texture in friction against lubricated skin", Journal of The Royal Society—Interface, 2014, pp. 1-6.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Feb. 15, 2023.
Advisory Action for U.S. Appl. No. 16/478,180 mailed Sep. 7, 2023.
Advisory Action for U.S. Appl. No. 17/051,550 mailed Sep. 8, 2023.
Advisory Action for U.S. Appl. No. 17/444,792 mailed Aug. 25, 2023.
Final Office Action for U.S. Appl. No. 16/369,676 mailed Aug. 31, 2023.
Final Office Action for U.S. Appl. No. 16/433,773 mailed Oct. 10, 2023.
Final Office Action for U.S. Appl. No. 16/478,180 mailed May 31, 2023.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/451,345 mailed May 3, 2023.
Final Office Action for U.S. Appl. No. 17/453,260 mailed Oct. 5, 2023.
Final Office Action for U.S. Appl. No. 17/653,137 mailed Sep. 21, 2023.
Final Office Action for U.S. Appl. No. 17/655,464 mailed Sep. 1, 2023.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
Issue Notification for U.S. Appl. No. 16/899,956 mailed Mar. 29, 2023.
Non-Final Office Action for U.S. Appl. No. 16/433,773 mailed Apr. 11, 2023.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,258 mailed Apr. 26, 2023.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,585 mailed Mar. 29, 2023.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/446,256 mailed Apr. 13, 2023.
Non-Final Office Action for U.S. Appl. No. 17/446,654 mailed Sep. 8, 2023.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/501,591 mailed Apr. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.

(56) References Cited

OTHER PUBLICATIONS

Non-Final Office Action for U.S. Appl. No. 17/664,487 mailed Jun. 8, 2023.
Non-Final Office Action for U.S. Appl. No. 18/139,523 mailed Aug. 17, 2023.
Non-Final Office Action for U.S. Appl. No. 18/140,751 mailed Sep. 14, 2023.
Notice of Allowance for U.S. Appl. No. 16/245,726 mailed Jul. 6, 2023.
Notice of Allowance for U.S. Appl. No. 17/051,554 mailed Jul. 6, 2023.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 18/299,788 mailed Jul. 24, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Text Messages to Lorena Eckert Re Prototype PureWick Holder dated Apr. 16, 2022.
U.S. Appl. No. 17/664,487, filed May 23, 2022.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 63/150,640, filed Feb. 18, 2021.
U.S. Appl. No. 63/308,190, filed Feb. 9, 2022.
*PureWick Corporation* v. *Sage Products, LLC* Transcripts vol. 2 , Mar. 29, 2022.
PureWick Corporation v. Sage Products, LLC Transcripts vol. 3 , Mar. 30, 2022.
*PureWick Corporation* v. *Sage Products, LLC* Transcripts vol. 4 , Mar. 31, 2022.
*PureWick Corporation* v. *Sage Products, LLC* Transcripts vol. 5 , Apr. 1, 2022.
*PureWick Corporation* v. *Sage Products, LLC* Transcripts vol. 1 , Mar. 28, 2022.
"AMXD Control Starter Kit" , Omni Medical Systems, Inc. , 1 page.
"AMXDmax Advanced Mission Extender Device User & Maintenance Guide" , Omni Medical , Jan. 11, 2010 , 10 pages.
"AMXDmax Development History 2002-2014" , Omni Medical Systems, Inc. , 2 pages.
"Combat Force Multiplier in Flight Bladder Relief Cockpit Essential Equipment Brochure" , Omni Medical , 20 pages.
"GSA Price List" , Omni Medical , Apr. 2011 , 2 pages.
"How is Polypropylene Fiber Made" , https:www.yarnsandfibers.com/textile-resources/synthetic-fibers/polypropylene-fiber/polypropylene-fiber-production-raw- materials/how-is-polypropylene-fiber-made/ last accessed 2020 , Oct. 7, 2020 , 3 pages.
"Letter to Mark Harvie of Omni Measurement Systems" , Department of Veterans Affairs , Nov. 1, 2007 , 11 pages.
"Revised AMXDmax Advanced Mission Extender Device User & Maintenance Guide" , Omni Medical Systems , Oct. 8, 2019 , 52 pages.
Merriam-Webster Dictionary, , "Embed Definition & Meaning" , https://www.merriam-webster.com/dictionary/embed last accessed Aug. 3, 2023 , 2003.
Pieper , et al. , "An external urine-collection device for women: A clinical trial" , Journal of ER Nursing, vol. 20, No. 2 , Mar./Apr. 1993 , pp. 51-55.
Vinas , "A Solution For An Awkward—But Serious—Subject" , http://www.aero-news.net/index.cfm?do=main.textpost&id=69ae2bb1-838b-4098-a7b5-7flbb2505688 last accessed Feb. 8, 2021.
Advisory Action for U.S. Appl. No. 16/433,773 mailed Dec. 29, 2023.
Advisory Action for U.S. Appl. No. 16/449,039 mailed Jan. 25, 2024.
Advisory Action for U.S. Appl. No. 16/904,868 mailed Jan. 2, 2024.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/653,137 mailed Dec. 1, 2023.
Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/663,330 mailed Feb. 27, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/904,868 mailed Nov. 2, 2023.

(56) References Cited

OTHER PUBLICATIONS

Final Office Action for U.S. Appl. No. 17/051,399 mailed Jan. 8, 2024.
Final Office Action for U.S. Appl. No. 17/179,116 mailed Oct. 31, 2023.
Final Office Action for U.S. Appl. No. 17/446,654 mailed Jan. 31, 2024.
Final Office Action for U.S. Appl. No. 17/450,864 mailed Dec. 28, 2023.
Final Office Action for U.S. Appl. No. 17/451,354 mailed Oct. 30, 2023.
Final Office Action for U.S. Appl. No. 17/501,591 mailed Nov. 14, 2023.
Final Office Action for U.S. Appl. No. 17/646,771 mailed Dec. 21, 2023.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 18/139,523 mailed Dec. 22, 2023.
Final Office Action for U.S. Appl. No. 18/140,751 mailed Jan. 17, 2024.
International Search Report and Written Opinion from International Application No. PCT/US2023/024805 mailed Dec. 14, 2023.
Issue Notification for U.S. Appl. No. 16/245,726 mailed Oct. 18, 2023.
Issue Notification for U.S. Appl. No. 17/461,036 mailed Oct. 11, 2023.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,145 mailed Nov. 2, 2023.
Non-Final Office Action for U.S. Appl. No. 16/478,180 mailed Nov. 7, 2023.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/444,792 mailed Nov. 17, 2023.
Non-Final Office Action for U.S. Appl. No. 17/446,256 mailed Feb. 13, 2024.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/451,345 mailed Jan. 17, 2024.
Non-Final Office Action for U.S. Appl. No. 17/453,560 mailed Oct. 16, 2023.
Non-Final Office Action for U.S. Appl. No. 17/645,821 mailed Oct. 25, 2023.
Non-Final Office Action for U.S. Appl. No. 17/653,137 mailed Jan. 18, 2024.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/134,857 mailed Jan. 25, 2024.
Non-Final Office Action for U.S. Appl. No. 18/140,163 mailed Nov. 9, 2023.
Non-Final Office Action for U.S. Appl. No. 18/198,464 mailed Dec. 7, 2023.
Notice of Allowance for U.S. Appl. No. 16/369,676 mailed Nov. 14, 2023.
Notice of Allowance for U.S. Appl. No. 17/051,550 mailed Feb. 7, 2024.
Notice of Allowance for U.S. Appl. No. 17/051,554 mailed Oct. 18, 2023.
Notice of Allowance for U.S. Appl. No. 17/326,980 mailed Jan. 29, 2024.
Notice of Allowance for U.S. Appl. No. 17/453,560 mailed Jan. 31, 2024.
Notice of Allowance for U.S. Appl. No. 17/662,700 mailed Nov. 15, 2023.
Notice of Allowance for U.S. Appl. No. 18/299,788 mailed Nov. 6, 2023.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/451,719, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 63/596,012, filed Nov. 3, 2023.
U.S. Appl. No. 63/608,553, filed Dec. 11, 2023.
Wikipedia Article, “Zylinder (Geometrie)”, https://de.wikipedia.org/w/index.php?title=Zylinder (Geometrie)&oldid=154862081, version of Jun. 1, 2016, 7 pages.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/446,654 mailed Apr. 15, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 17/444,792 mailed Apr. 3, 2024.
Final Office Action for U.S. Appl. No. 17/447,123 mailed May 14, 2024.

(56) References Cited

OTHER PUBLICATIONS

Final Office Action for U.S. Appl. No. 17/451,345 mailed Apr. 18, 2024.
Final Office Action for U.S. Appl. No. 17/645,821 mailed Apr. 3, 2024.
Final Office Action for U.S. Appl. No. 17/808,354 mailed Apr. 10, 2024.
Final Office Action for U.S. Appl. No. 18/140,163 mailed Mar. 27, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/077208 mailed May 10, 2024.
Issue Notification for U.S. Appl. No. 16/449,039 mailed Jun. 19, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/657,474 mailed Jun. 19, 2024.
Non-Final Office Action for U.S. Appl. No. 16/452,258 mailed Jun. 20, 2024.
Non-Final Office Action for U.S. Appl. No. 16/904,868 mailed Mar. 12, 2024.
Non-Final Office Action for U.S. Appl. No. 17/450,864 mailed May 29, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,673 mailed Mar. 20, 2024.
Non-Final Office Action for U.S. Appl. No. 17/646,771 mailed Apr. 24, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/664,487 mailed Jun. 17, 2024.
Non-Final Office Action for U.S. Appl. No. 18/003,029 mailed Mar. 26, 2024.
Non-Final Office Action for U.S. Appl. No. 18/389,009 mailed May 24, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 17/326,980 mailed Apr. 5, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 18/198,464 mailed Apr. 17, 2024.
Restriction Requirement for U.S. Appl. No. 17/527,769 mailed Jun. 17, 2024.
Restriction Requirement for U.S. Appl. No. 17/667,097 mailed Mar. 20, 2024.
U.S. Appl. No. 17/444,792, filed Aug. 10, 2021.
U.S. Appl. No. 18/249,577, filed Oct. 19, 2021.
U.S. Appl. No. 18/610,523, filed Mar. 20, 2024.
U.S. Appl. No. 18/662,216, filed May 13, 2024.
U.S. Appl. No. 18/693,638, filed Mar. 20, 2024.
U.S. Appl. No. 18/694,090, filed Mar. 21, 2024.
U.S. Appl. No. 63/561,893, filed Dec. 11, 2023.
Wikipedia Article, "Decibel", https://web.archive.org/web/20200415219177/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Final Office Action for U.S. Appl. No. 17/451,345 mailed Feb. 6, 2025,.
Final Office Action for U.S. Appl. No. 17/653,314 mailed Jan. 30, 2025,.
International Search Report and Written Opinion from International Application No. PCT/US2024/053681 mailed Jan. 27, 2025,.
Issue Notification for U.S. Appl. No. 17/661,090 mailed Feb. 5, 2025,.
Issue Notification for U.S. Appl. No. 18/140,751 mailed Feb. 12, 2025,.
Non-Final Office Action for U.S. Appl. No. 17/653,137 mailed Jan. 28, 2025,.
Notice of Allowance for U.S. Appl. No. 16/904,868 mailed Jan. 21, 2025,.
Notice of Allowance for U.S. Appl. No. 17/596,629 mailed Jan. 29, 2025,.
Notice of Allowance for U.S. Appl. No. 17/749,340 mailed Feb. 14, 2025.
U.S. Appl. No. 19/038,774, filed Jan. 28, 2025.
U.S. Appl. No. 19/039,165, filed Jan. 28, 2025.
U.S. Appl. No. 19/046,047, filed Feb. 5, 2025.
U.S. Appl. No. 19/047,728, filed Feb. 7, 2025.
U.S. Appl. No. 19/048,004, filed Feb. 7, 2025.
U.S. Appl. No. 19/049,501, filed Feb. 10, 2025.
U.S. Appl. No. 19/049,783, filed Feb. 10, 2025.
U.S. Appl. No. 19/103,165, filed Feb. 11, 2025.
U.S. Appl. No. 63/181,709, filed Apr. 29, 2021.
Advisory Action for U.S. Appl. No. 17/051,585 mailed Oct. 8, 2024.
Advisory Action for U.S. Appl. No. 17/444,792 mailed Jul. 8, 2024.
Advisory Action for U.S. Appl. No. 17/446,256 mailed Nov. 19, 2024.
Advisory Action for U.S. Appl. No. 17/451,345 mailed Jul. 3, 2024.
Advisory Action for U.S. Appl. No. 17/597,673 mailed Jan. 7, 2025.
Advisory Action for U.S. Appl. No. 17/645,821 mailed Jul. 2, 2024.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 18/003,029 mailed Jan. 8, 2025.
Advisory Action for U.S. Appl. No. 18/134,857 mailed Oct. 23, 2024.
Corrected Notice of Allowability for U.S. Appl. No. 17/450,864 mailed Oct. 24, 2024.
Corrected Notice of Allowability for U.S. Appl. No. 17/501,591 mailed Aug. 9, 2024.
Corrected Notice of Allowability for U.S. Appl. No. 17/646,771 mailed Jan. 17, 2025.

(56) References Cited

OTHER PUBLICATIONS

Corrected Notice of Allowability for U.S. Appl. No. 17/664,914 mailed Aug. 9, 2024.
Corrected Notice of Allowability for U.S. Appl. No. 18/426,795 mailed Dec. 4, 2024.
Final Office Action for U.S. Appl. No. 16/433,773 mailed Sep. 9, 2024.
Final Office Action for U.S. Appl. No. 16/452,258 mailed Jan. 6, 2025.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/446,256 mailed Aug. 7, 2024.
Final Office Action for U.S. Appl. No. 17/446,654 mailed Dec. 18, 2024.
Final Office Action for U.S. Appl. No. 17/451,354 mailed Oct. 28, 2024.
Final Office Action for U.S. Appl. No. 17/595,747 mailed Dec. 12, 2024.
Final Office Action for U.S. Appl. No. 17/597,673 mailed Oct. 22, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 17/655,464 mailed Nov. 29, 2024.
Final Office Action for U.S. Appl. No. 17/664,487 mailed Jan. 13, 2025.
Final Office Action for U.S. Appl. No. 18/003,029 mailed Oct. 22, 2024.
Final Office Action for U.S. Appl. No. 18/134,857 mailed Jul. 25, 2024.
International Search Report and Written Opinion from International Application No. PCT/US2023/036238 mailed Jul. 22, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077168 mailed Jun. 24, 2024.
International Search Report and Written Opinion from International Application No. PCT/US2023/080680 mailed Jul. 22, 2024.
International Search Report and Written Opinion from International Application No. PCT/US2023/085516 mailed Aug. 26, 2024.
Issue Notification for U.S. Appl. No. 16/369,676 mailed Oct. 2, 2024.
Issue Notification for U.S. Appl. No. 16/452,145 mailed Oct. 23, 2024.
Issue Notification for U.S. Appl. No. 17/179,116 mailed Dec. 25, 2024.
Issue Notification for U.S. Appl. No. 17/326,980 mailed Jul. 10, 2024.
Issue Notification for U.S. Appl. No. 17/447,123 mailed Nov. 13, 2024.
Issue Notification for U.S. Appl. No. 17/448,811 mailed Jul. 3, 2024.
Issue Notification for U.S. Appl. No. 17/450,864 mailed Jan. 8, 2025.
Issue Notification for U.S. Appl. No. 17/453,260 mailed Jul. 10, 2024.
Issue Notification for U.S. Appl. No. 17/453,560 mailed Aug. 7, 2024.
Issue Notification for U.S. Appl. No. 17/662,700 mailed Oct. 23, 2024.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/198,464 mailed Nov. 20, 2024.
Issue Notification for U.S. Appl. No. 18/389,009 mailed Dec. 18, 2024.
Non-Final Office Action for U.S. Appl. No. 16/478,180 mailed Aug. 7, 2024.
Non-Final Office Action for U.S. Appl. No. 17/378,015 mailed Jul. 5, 2024.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/446,654 mailed Jun. 25, 2024.
Non-Final Office Action for U.S. Appl. No. 17/451,345 mailed Jul. 25, 2024.
Non-Final Office Action for U.S. Appl. No. 17/597,408 mailed Aug. 15, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/645,821 mailed Sep. 6, 2024.
Non-Final Office Action for U.S. Appl. No. 17/653,314 mailed Aug. 29, 2024.
Non-Final Office Action for U.S. Appl. No. 17/653,920 mailed Nov. 27, 2024.
Non-Final Office Action for U.S. Appl. No. 17/663,330 mailed Jul. 1, 2024.
Non-Final Office Action for U.S. Appl. No. 17/749,340 mailed Aug. 14, 2024.
Non-Final Office Action for U.S. Appl. No. 17/757,311 mailed Oct. 22, 2024.
Non-Final Office Action for U.S. Appl. No. 17/758,316 mailed Aug. 28, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/907,125 mailed Dec. 13, 2024.
Non-Final Office Action for U.S. Appl. No. 18/139,523 mailed Aug. 26, 2024.
Non-Final Office Action for U.S. Appl. No. 18/140,751 mailed Jun. 21, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Non-Final Office Action for U.S. Appl. No. 18/584,002 mailed Sep. 19, 2024.
Notice of Allowance for U.S. Appl. No. 16/452,145 mailed Jul. 11, 2024.
Notice of Allowance for U.S. Appl. No. 16/478,180 mailed Dec. 16, 2024.
Notice of Allowance for U.S. Appl. No. 16/904,868 mailed Sep. 29, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/447,123 mailed Jul. 26, 2024.
Notice of Allowance for U.S. Appl. No. 17/450,864 mailed Sep. 18, 2024.

(56) References Cited

OTHER PUBLICATIONS

Notice of Allowance for U.S. Appl. No. 17/501,591 mailed Jul. 31, 2024.
Notice of Allowance for U.S. Appl. No. 17/501,591 mailed Nov. 20, 2024.
Notice of Allowance for U.S. Appl. No. 17/527,769 mailed Nov. 20, 2024.
Notice of Allowance for U.S. Appl. No. 17/646,771 mailed Dec. 17, 2024.
Notice of Allowance for U.S. Appl. No. 17/661,090 mailed Oct. 30, 2024.
Notice of Allowance for U.S. Appl. No. 17/663,330 mailed Nov. 20, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/140,751 mailed Nov. 1, 2024.
Notice of Allowance for U.S. Appl. No. 18/198,464 mailed Jul. 30, 2024.
Notice of Allowance for U.S. Appl. No. 18/389,009 mailed Aug. 28, 2024.
Notice of Allowance for U.S. Appl. No. 18/415,080 mailed Dec. 30, 2024.
Notice of Allowance for U.S. Appl. No. 18/426,795 mailed Nov. 20, 2024.
Notice of Allowance for U.S. Appl. No. 18/584,002 mailed Jan. 8, 2025.
Restriction Requirement for U.S. Appl. No. 17/596,629 mailed Sep. 19, 2024.
Restriction Requirement for U.S. Appl. No. 17/625,941 mailed Aug. 7, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/809,083 mailed Dec. 31, 2024.
Restriction Requirement for U.S. Appl. No. 17/878,268 mailed Sep. 20, 2024.
U.S. Appl. No. 17/013,822, filed Sep. 7, 2020.
U.S. Appl. No. 17/654,156, filed Mar. 9, 2022.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 63/564,696, filed Mar. 13, 2024.
U.S. Appl. No. 63/159,280, filed Mar. 10, 2021.
U.S. Appl. No. 63/568,615, filed Mar. 22, 2024.
U.S. Appl. No. 63/683,428, filed Aug. 15, 2024.
U.S. Appl. No. 63/711,438, filed Oct. 24, 2024.
U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Advisory Action for U.S. Appl. No. 17/446,654 mailed Feb. 28, 2025.
Advisory Action for U.S. Appl. No. 17/595,747 mailed Mar. 17, 2025.
Advisory Action for U.S. Appl. No. 17/655,464 mailed Feb. 25, 2025.
Corrected Notice of Allowability for U.S. Appl. No. 18/134,857 mailed Mar. 14, 2025.
Final Office Action for U.S. Appl. No. 17/625,941 mailed Feb. 18, 2025.
International Search Report and Written Opinion from International Application No. PCT/US2023/031432 mailed Feb. 29, 2024.
Issue Notification for U.S. Appl. No. 16/478,180 mailed Mar. 5, 2025.
Issue Notification for U.S. Appl. No. 17/501,591 mailed Mar. 5, 2025.
Issue Notification for U.S. Appl. No. 17/529,769 mailed Feb. 19, 2025.
Issue Notification for U.S. Appl. No. 17/663,330 mailed Feb. 26, 2025.
Issue Notification for U.S. Appl. No. 18/426,795 mailed Feb. 19, 2025.
Non-Final Office Action for U.S. Appl. No. 16/433,773 mailed Feb. 28, 2025.
Non-Final Office Action for U.S. Appl. No. 17/051,600 mailed Feb. 28, 2025.
Non-Final Office Action for U.S. Appl. No. 17/394,055 mailed Mar. 13, 2025.
Non-Final Office Action for U.S. Appl. No. 17/809,083 mailed Mar. 7, 2025.
Non-Final Office Action for U.S. Appl. No. 17/878,268 mailed Mar. 17, 2025.
Non-Final Office Action for U.S. Appl. No. 17/996,064 mailed Mar. 6, 2025.
Notice of Allowance for U.S. Appl. No. 17/597,673 mailed Feb. 26, 2025.
Notice of Allowance for U.S. Appl. No. 17/996,155 mailed Mar. 11, 2025.
Notice of Allowance for U.S. Appl. No. 18/134,857 mailed Feb. 20, 2025.
Restriction Requirement for U.S. Appl. No. 17/929,887 mailed Mar. 10, 2025.
U.S. Appl. No. 19/058,726, filed Feb. 20, 2025.
U.S. Appl. No. 19/069,480, filed Mar. 4, 2025.
U.S. Appl. No. 19/078,602, filed Mar. 13, 2025.
U.S. Appl. No. 19/110,938, filed Mar. 12, 2025.
U.S. Appl. No. 19/111,921, filed Mar. 14, 2025.
Advisory Action for U.S. Appl. No. 17/653,314 mailed Apr. 8, 2025.
Final Office Action for U.S. Appl. No. 17/597,408 mailed Mar. 24, 2025.
Final Office Action for U.S. Appl. No. 17/757,311 mailed Mar. 31, 2025.
Issue Notification for U.S. Appl. No. 17/051,585 mailed Mar. 26, 2025.
Issue Notification for U.S. Appl. No. 17/646,771 mailed Mar. 19, 2025.

(56) References Cited

OTHER PUBLICATIONS

Issue Notification for U.S. Appl. No. 18/415,080 mailed Apr. 9, 2025.
Non-Final Office Action for U.S. Appl. No. 17/394,055 mailed Mar. 19, 2025.
Non-Final Office Action for U.S. Appl. No. 17/451,354 mailed Mar. 19, 2025.
Non-Final Office Action for U.S. Appl. No. 17/631,619 mailed Mar. 19, 2025.
Non-Final Office Action for U.S. Appl. No. 17/645,821 mailed Mar. 31, 2025.
Non-Final Office Action for U.S. Appl. No. 17/655,464 mailed Mar. 20, 2025.
Non-Final Office Action for U.S. Appl. No. 17/754,736 mailed Mar. 31, 2025.
Non-Final Office Action for U.S. Appl. No. 17/758,152 mailed Apr. 8, 2025.
Non-Final Office Action for U.S. Appl. No. 17/809,083 mailed Apr. 2, 2025.
Notice of Allowance for U.S. Appl. No. 17/444,792 mailed Mar. 28, 2025.
Notice of Allowance for U.S. Appl. No. 17/758,316 mailed Mar. 24, 2025.
Notice of Allowance for U.S. Appl. No. 17/996,253 mailed Apr. 11, 2025.
Notice of Allowance for U.S. Appl. No. 17/996,468 mailed Apr. 14, 2025.
Supplemental Notice of Allowance for U.S. Appl. No. 17/597,673 mailed Apr. 10, 2025.
U.S. Appl. No. 19/092,262, filed Mar. 27, 2025.
U.S. Appl. No. 19/171,983, filed Apr. 7, 2025.
Foamtech, “Foam Packaging Isnert: Best Selection Guide”, https://web/archive. org/web/20170922162235/http://www.foamtechchina/com:80/foam-packaging-insert/, Sep. 22, 2017, 25 pages.
“Proximate Definition & Meaning” <https://www.merriam-webster.com/dictionary/> 2025.
“Surface Energy Data for Cellulose acetate, CAS # 9004-35-7”, Diviersified Enterprises, 2009, 1 page.
“Tube Definition & Meaning” Merriam Webster Dictionary, 2025, <https://www.merriam-webster.com/dictionary/tube>.
Advisory Action for U.S. Appl. No. 16/452,258 mailed Apr. 17, 2026.
Advisory Action for U.S. Appl. No. 16/452,258 mailed May 5, 2025.
Advisory Action for U.S. Appl. No. 17/378,015 mailed Oct. 28, 2025.
Advisory Action for U.S. Appl. No. 17/394,055 mailed Jan. 9, 2026.
Advisory Action for U.S. Appl. No. 17/446,256 mailed Nov. 6, 2025.
Advisory Action for U.S. Appl. No. 17/446,654 mailed Apr. 16, 2026.
Advisory Action for U.S. Appl. No. 17/450,864 mailed Mar. 21, 2024.
Advisory Action for U.S. Appl. No. 17/451,345 mailed May 13, 2025.
Advisory Action for U.S. Appl. No. 17/664,487 mailed Apr. 24, 2025.
Advisory Action for U.S. Appl. No. 17/664,487 mailed Apr. 9, 2026.
Advisory Action for U.S. Appl. No. 17/757,311 mailed Jul. 2, 2025.
Advisory Action for U.S. Appl. No. 17/929,887 mailed Apr. 16, 2026.
Advisory Action for U.S. Appl. No. 18/006,807 mailed May 4, 2026.
Advisory Action for U.S. Appl. No. 18/042,842 mailed Apr. 14, 2026.
Advisory Action for U.S. Appl. No. 18/247,986 mailed Apr. 1, 2026.
Advisory Action for U.S. Appl. No. 18/265,736 mailed Mar. 4, 2026.
Corrected Notice of Allowability for U.S. Appl. No. 17/444,792 mailed Jun. 24, 2025.
Corrected Notice of Allowability for U.S. Appl. No. 17/653,314 mailed Oct. 29, 2025.
Corrected Notice of Allowability for U.S. Appl. No. 17/754,736 mailed Feb. 12, 2026.
Corrected Notice of Allowability for U.S. Appl. No. 17/808,354 mailed Nov. 25, 2025.
Corrected Notice of Allowability for U.S. Appl. No. 17/996,253 mailed Apr. 28, 2025.
Corrected Notice of Allowability for U.S. Appl. No. 18/041,109 mailed Apr. 2, 2026.
Corrected Notice of Allowability for U.S. Appl. No. 18/249,577 mailed Apr. 15, 2026.
Corrected Notice of Allowability for U.S. Appl. No. 18/260,122 mailed Aug. 11, 2025.
Corrected Notice of Allowability for U.S. Appl. No. 18/264,004 mailed Feb. 10, 2026.
Corrected Notice of Allowability for U.S. Appl. No. 18/264,004 mailed Feb. 3, 2026.
Corrected Notice of Allowability for U.S. Appl. No. 18/294,370 mailed Mar. 31, 2026.
Decision Granting Institution of Inter Partes Review for U.S. Pat. No. 8,287,508, Feb. 17, 2021,39 pages.
Di Mauro, et al., “Penile length and circumference dimensions: A large study in young Italian men” Reconstructive Urology, Men’s Health Working Parties of the European Association of Urology (EAU) Young Academic Urologists (YAU). pp. 1-7, Mar. 8, 2021.
Final Office Action for U.S. Appl. No. 16/452,258 mailed Feb. 11, 2026.
Final Office Action for U.S. Appl. No. 17/051,600 mailed Aug. 6, 2025.
Final Office Action for U.S. Appl. No. 17/378,015 mailed Jun. 18, 2025.
Final Office Action for U.S. Appl. No. 17/394,055 mailed Sep. 24, 2025.
Final Office Action for U.S. Appl. No. 17/446,256 mailed Jun. 11, 2025.
Final Office Action for U.S. Appl. No. 17/446,654 mailed Dec. 22, 2025.
Final Office Action for U.S. Appl. No. 17/595,747 mailed Feb. 19, 2026.
Final Office Action for U.S. Appl. No. 17/614,173 mailed May 20, 2025.
Final Office Action for U.S. Appl. No. 17/628,411 mailed Apr. 30, 2025.
Final Office Action for U.S. Appl. No. 17/628,411 mailed Apr. 7, 2026.
Final Office Action for U.S. Appl. No. 17/631,619 mailed Oct. 1, 2025.
Final Office Action for U.S. Appl. No. 17/653,137 mailed Jun. 25, 2025.
Final Office Action for U.S. Appl. No. 17/653,920 mailed Apr. 24, 2025.
Final Office Action for U.S. Appl. No. 17/655,464 mailed Feb. 17, 2026.
Final Office Action for U.S. Appl. No. 17/664,487 mailed Jan. 5, 2026.
Final Office Action for U.S. Appl. No. 17/756,201 mailed Dec. 30, 2025.
Final Office Action for U.S. Appl. No. 17/758,152 mailed Apr. 7, 2026.
Final Office Action for U.S. Appl. No. 17/759,697 mailed Jun. 4, 2025.
Final Office Action for U.S. Appl. No. 17/808,354 mailed Jun. 13, 2025.
Final Office Action for U.S. Appl. No. 17/809,083 mailed Jan. 23, 2026.
Final Office Action for U.S. Appl. No. 17/907,125 mailed Apr. 30, 2025.
Final Office Action for U.S. Appl. No. 17/929,887 filed Jan. 13, 2026.
Final Office Action for U.S. Appl. No. 17/933,590 mailed Feb. 19, 2026.

(56) References Cited

OTHER PUBLICATIONS

Final Office Action for U.S. Appl. No. 18/003,029 mailed Nov. 26, 2025.
Final Office Action for U.S. Appl. No. 18/006,807 mailed Dec. 23, 2025.
Final Office Action for U.S. Appl. No. 18/042,842 mailed Jan. 27, 2026.
Final Office Action for U.S. Appl. No. 18/043,618 mailed Nov. 26, 2025.
Final Office Action for U.S. Appl. No. 18/139,523 mailed May 8, 2025.
Final Office Action for U.S. Appl. No. 18/150,360 mailed Apr. 10, 2026.
Final Office Action for U.S. Appl. No. 18/247,986 mailed Jan. 7, 2026.
Final Office Action for U.S. Appl. No. 18/254,638 mailed Apr. 8, 2026.
Final Office Action for U.S. Appl. No. 18/265,736 mailed Dec. 1, 2025.
Final Office Action for U.S. Appl. No. 18/548,152 mailed Apr. 15, 2026.
International Search Report and Written Opinion from International Application No. PCT/US2023/036875 mailed May 31, 2024.
International Search Report and Written Opinion from International Application No. PCT/US2023/077205 mailed Jul. 19, 2024.
International Search Report and Written Opinion from International Application No. PCT/US2024/058598 mailed Mar. 28, 2025.
International Search Report and Written Opinion from International Application No. PCT/US2025/018907 mailed May 16, 2025.
International Search Report and Written Opinion from International Application No. PCT/US2025/018909 mailed May 20, 2025.
International Search Report and Written Opinion from International Application No. PCT/US2025/018913 mailed Jun. 18, 2025.
Issue Notification for U.S. Appl. No. 16/433,773 mailed Jan. 21, 2026.
Issue Notification for U.S. Appl. No. 16/904,868 mailed Apr. 30, 2025.
Issue Notification for U.S. Appl. No. 17/051,399 mailed Mar. 4, 2026.
Issue Notification for U.S. Appl. No. 17/051,600 mailed Apr. 29, 2026.
Issue Notification for U.S. Appl. No. 17/444,792 mailed Jun. 25, 2025.
Issue Notification for U.S. Appl. No. 17/451,354 mailed Feb. 25, 2026.
Issue Notification for U.S. Appl. No. 17/597,673 mailed Jun. 4, 2025.
Issue Notification for U.S. Appl. No. 17/625,941 mailed Feb. 25, 2026.
Issue Notification for U.S. Appl. No. 17/645,821 mailed Apr. 1, 2026.
Issue Notification for U.S. Appl. No. 17/653,137 mailed Feb. 4, 2025.
Issue Notification for U.S. Appl. No. 17/653,314 mailed Feb. 11, 2026.
Issue Notification for U.S. Appl. No. 17/653,920 mailed Oct. 22, 2025.
Issue Notification for U.S. Appl. No. 17/749,340 mailed May 28, 2025.
Issue Notification for U.S. Appl. No. 17/755,236 mailed Oct. 29, 2025.
Issue Notification for U.S. Appl. No. 17/758,316 mailed Jun. 25, 2025.
Issue Notification for U.S. Appl. No. 17/808,354 mailed Mar. 4, 2026.
Issue Notification for U.S. Appl. No. 17/878,268 mailed Feb. 4, 2026.
Issue Notification for U.S. Appl. No. 17/907,125 mailed Dec. 30, 2025.
Issue Notification for U.S. Appl. No. 17/912,147 mailed Mar. 18, 2026.
Issue Notification for U.S. Appl. No. 17/996,064 mailed Nov. 5, 2025.
Issue Notification for U.S. Appl. No. 17/996,155 mailed Oct. 8, 2025.
Issue Notification for U.S. Appl. No. 17/996,253 mailed Oct. 29, 2025.
Issue Notification for U.S. Appl. No. 17/996,468 mailed Nov. 26, 2025.
Issue Notification for U.S. Appl. No. 18/007,105 mailed Oct. 1, 2025.
Issue Notification for U.S. Appl. No. 18/044,413 mailed Dec. 30, 2025.
Issue Notification for U.S. Appl. No. 18/134,857 mailed May 28, 2025.
Issue Notification for U.S. Appl. No. 18/260,122 mailed Nov. 12, 2025.
Issue Notification for U.S. Appl. No. 18/584,002 mailed Apr. 16, 2025.
Non-Final Office Action for U.S. Appl. No. 16/452,258 mailed Sep. 24, 2025.
Non-Final Office Action for U.S. Appl. No. 17/378,015 mailed Dec. 12, 2025.
Non-Final Office Action for U.S. Appl. No. 17/446,256 mailed Dec. 2, 2025.
Non-Final Office Action for U.S. Appl. No. 17/446,654 mailed May 1, 2025.
Non-Final Office Action for U.S. Appl. No. 17/595,747 mailed Jun. 12, 2025.
Non-Final Office Action for U.S. Appl. No. 17/597,408 mailed Apr. 7, 2026.
Non-Final Office Action for U.S. Appl. No. 17/614,173 mailed Dec. 29, 2025.
Non-Final Office Action for U.S. Appl. No. 17/628,411 mailed Dec. 22, 2025.
Non-Final Office Action for U.S. Appl. No. 17/635,866 mailed Jul. 29, 2025.
Non-Final Office Action for U.S. Appl. No. 17/653,314 mailed May 8, 2025.
Non-Final Office Action for U.S. Appl. No. 17/664,487 mailed May 19, 2025.
Non-Final Office Action for U.S. Appl. No. 17/756,201 mailed Apr. 24, 2025.
Non-Final Office Action for U.S. Appl. No. 17/757,311 mailed Sep. 2, 2025.
Non-Final Office Action for U.S. Appl. No. 17/759,587 mailed Jan. 26, 2026.
Non-Final Office Action for U.S. Appl. No. 17/759,697 mailed Sep. 17, 2025.
Non-Final Office Action for U.S. Appl. No. 17/912,147 mailed May 29, 2025.
Non-Final Office Action for U.S. Appl. No. 17/929,887 mailed Jun. 25, 2025.
Non-Final Office Action for U.S. Appl. No. 17/930,238 mailed Jun. 30, 2025.
Non-Final Office Action for U.S. Appl. No. 17/933,590 mailed Jul. 29, 2025.
Non-Final Office Action for U.S. Appl. No. 17/996,556 mailed Dec. 22, 2025.
Non-Final Office Action for U.S. Appl. No. 18/003,029 mailed Apr. 18, 2025.
Non-Final Office Action for U.S. Appl. No. 18/003,029 mailed Apr. 20, 2026.
Non-Final Office Action for U.S. Appl. No. 18/006,807 mailed May 29, 2025.
Non-Final Office Action for U.S. Appl. No. 18/034,902 mailed Mar. 20, 2026.
Non-Final Office Action for U.S. Appl. No. 18/042,842 mailed May 22, 2025.
Non-Final Office Action for U.S. Appl. No. 18/043,618 mailed May 1, 2026.

(56) References Cited

OTHER PUBLICATIONS

Non-Final Office Action for U.S. Appl. No. 18/043,618 mailed May 19, 2025.
Non-Final Office Action for U.S. Appl. No. 18/043,807 mailed Feb. 10, 2026.
Non-Final Office Action for U.S. Appl. No. 18/115,444 mailed Oct. 22, 2025.
Non-Final Office Action for U.S. Appl. No. 18/139,523 mailed Nov. 19, 2025.
Non-Final Office Action for U.S. Appl. No. 18/150,360 mailed Nov. 5, 2025.
Non-Final Office Action for U.S. Appl. No. 18/246,121 mailed Jan. 22, 2026.
Non-Final Office Action for U.S. Appl. No. 18/247,986 mailed Jun. 4, 2025.
Non-Final Office Action for U.S. Appl. No. 18/249,577 mailed Nov. 17, 2025.
Non-Final Office Action for U.S. Appl. No. 18/254,638 mailed Nov. 17, 2025.
Non-Final Office Action for U.S. Appl. No. 18/259,626 mailed Jan. 30, 2026.
Non-Final Office Action for U.S. Appl. No. 18/259,626 mailed Jul. 11, 2025.
Non-Final Office Action for U.S. Appl. No. 18/260,391 mailed Apr. 29, 2026.
Non-Final Office Action for U.S. Appl. No. 18/260,394 mailed Jan. 13, 2026.
Non-Final Office Action for U.S. Appl. No. 18/263,800 mailed Feb. 5, 2026.
Non-Final Office Action for U.S. Appl. No. 18/264,004 mailed May 15, 2025.
Non-Final Office Action for U.S. Appl. No. 18/264,278 mailed Nov. 10, 2025.
Non-Final Office Action for U.S. Appl. No. 18/265,736 mailed Jul. 1, 2025.
Non-Final Office Action for U.S. Appl. No. 18/335,579 mailed Apr. 24, 2026.
Non-Final Office Action for U.S. Appl. No. 18/376,274 mailed Mar. 9, 2026.
Non-Final Office Action for U.S. Appl. No. 18/546,465 mailed Apr. 1, 2026.
Non-Final Office Action for U.S. Appl. No. 18/548,152 mailed Sep. 16, 2025.
Non-Final Office Action for U.S. Appl. No. 18/549,387 mailed Mar. 4, 2026.
Non-Final Office Action for U.S. Appl. No. 18/551,492 mailed Mar. 19, 2026.
Non-Final Office Action for U.S. Appl. No. 18/553,625 mailed Oct. 2, 2025.
Non-Final Office Action for U.S. Appl. No. 18/556,945 mailed Dec. 19, 2025.
Non-Final Office Action for U.S. Appl. No. 18/562,626 mailed Feb. 11, 2026.
Non-Final Office Action for U.S. Appl. No. 18/563,672 mailed Feb. 12, 2026.
Non-Final Office Action for U.S. Appl. No. 18/569,711 mailed Mar. 30, 2026.
Non-Final Office Action for U.S. Appl. No. 18/569,778 mailed May 1, 2026.
Non-Final Office Action for U.S. Appl. No. 18/662,216 mailed Mar. 9, 2026.
Non-Final Office Action for U.S. Appl. No. 18/681,987 mailed Mar. 30, 2026.
Non-Final Office Action for U.S. Appl. No. 18/682,006 mailed Mar. 4, 2026.
Non-Final Office Action for U.S. Appl. No. 18/689,532 mailed Mar. 19, 2026.
Non-Final Office Action for U.S. Appl. No. 18/690,392 mailed Feb. 9, 2026.
Non-Final Office Action for U.S. Appl. No. 18/694,090 mailed Mar. 17, 2026.
Non-Final Office Action for U.S. Appl. No. 18/757,964 mailed Aug. 20, 2025.
Non-Final Office Action for U.S. Appl. No. 18/757,964 mailed Mar. 27, 2026.
Non-Final Office Action for U.S. Appl. No. 18/835,444 mailed Apr. 24, 2026.
Non-Final Office Action for U.S. Appl. No. 19/237,368 mailed Apr. 6, 2026.
Non-Final Office Action for U.S. Appl. No. 29/892,478 mailed Mar. 12, 2026.
Notice of Allowance for U.S. Appl. No. 16/433,773 mailed Oct. 10, 2025.
Notice of Allowance for U.S. Appl. No. 17/051,399 mailed Nov. 17, 2025.
Notice of Allowance for U.S. Appl. No. 17/051,600 mailed Jan. 5, 2026.
Notice of Allowance for U.S. Appl. No. 17/394,055 mailed Mar. 20, 2026.
Notice of Allowance for U.S. Appl. No. 17/451,345 mailed Jun. 24, 2025.
Notice of Allowance for U.S. Appl. No. 17/451,354 mailed Nov. 18, 2025.
Notice of Allowance for U.S. Appl. No. 17/596,629 mailed May 27, 2025.
Notice of Allowance for U.S. Appl. No. 17/625,887 mailed Mar. 3, 2026.
Notice of Allowance for U.S. Appl. No. 17/625,941 mailed Nov. 13, 2025.
Notice of Allowance for U.S. Appl. No. 17/635,866 mailed Mar. 2, 2026.
Notice of Allowance for U.S. Appl. No. 17/645,821 mailed Nov. 24, 2025.
Notice of Allowance for U.S. Appl. No. 17/653,137 mailed Oct. 22, 2025.
Notice of Allowance for U.S. Appl. No. 17/653,314 mailed Oct. 20, 2025.
Notice of Allowance for U.S. Appl. No. 17/653,920 mailed Jul. 9, 2025.
Notice of Allowance for U.S. Appl. No. 17/754,736 mailed Jan. 28, 2026.
Notice of Allowance for U.S. Appl. No. 17/755,236 mailed Jul. 17, 2025.
Notice of Allowance for U.S. Appl. No. 17/759,697 mailed Jan. 30, 2026.
Notice of Allowance for U.S. Appl. No. 17/808,354 mailed Nov. 12, 2025.
Notice of Allowance for U.S. Appl. No. 17/878,268 mailed Oct. 15, 2025.
Notice of Allowance for U.S. Appl. No. 17/907,125 mailed Sep. 26, 2025.
Notice of Allowance for U.S. Appl. No. 17/912,147 mailed Dec. 3, 2025.
Notice of Allowance for U.S. Appl. No. 17/930,238 mailed Dec. 16, 2025.
Notice of Allowance for U.S. Appl. No. 17/996,064 mailed Jul. 29, 2025.
Notice of Allowance for U.S. Appl. No. 17/996,155 mailed Jun. 24, 2025.
Notice of Allowance for U.S. Appl. No. 17/996,253 mailed Jul. 11, 2025.
Notice of Allowance for U.S. Appl. No. 17/996,468 mailed Jul. 15, 2025.
Notice of Allowance for U.S. Appl. No. 18/007,105 mailed Jun. 17, 2025.
Notice of Allowance for U.S. Appl. No. 18/041,109 mailed Mar. 25, 2026.
Notice of Allowance for U.S. Appl. No. 18/044,413 mailed Sep. 16, 2025.
Notice of Allowance for U.S. Appl. No. 18/249,577 mailed Mar. 31, 2026.

(56) References Cited

OTHER PUBLICATIONS

Notice of Allowance for U.S. Appl. No. 18/260,122 mailed Jul. 30, 2025.
Notice of Allowance for U.S. Appl. No. 18/264,004 mailed Jan. 30, 2026.
Notice of Allowance for U.S. Appl. No. 18/264,278 mailed Apr. 24, 2026.
Notice of Allowance for U.S. Appl. No. 18/294,370 mailed Mar. 17, 2026.
Notice of Allowance for U.S. Appl. No. 18/553,625 mailed Apr. 15, 2026.
Notice of Allowance for U.S. Appl. No. 18/610,523 mailed Mar. 4, 2026.
Restriction Requirement for U.S. Appl. No. 17/625,887 mailed Sep. 2, 2025.
Restriction Requirement for U.S. Appl. No. 17/755,236 mailed Apr. 24, 2025.
Restriction Requirement for U.S. Appl. No. 17/930,238 mailed Apr. 17, 2025.
Restriction Requirement for U.S. Appl. No. 17/996,556 mailed Aug. 11, 2025.
Restriction Requirement for U.S. Appl. No. 18/034,902 mailed Nov. 6, 2025.
Restriction Requirement for U.S. Appl. No. 18/041,109 mailed Jun. 4, 2025.
Restriction Requirement for U.S. Appl. No. 18/041,109 mailed Oct. 23, 2025.
Restriction Requirement for U.S. Appl. No. 18/150,360 mailed May 19, 2025.
Restriction Requirement for U.S. Appl. No. 18/246,121 mailed Jul. 25, 2025.
Restriction Requirement for U.S. Appl. No. 18/249,577 mailed Aug. 25, 2025.
Restriction Requirement for U.S. Appl. No. 18/254,638 mailed Jul. 21, 2025.
Restriction Requirement for U.S. Appl. No. 18/260,394 mailed Jul. 25, 2025.
Restriction Requirement for U.S. Appl. No. 18/294,370 mailed Nov. 26, 2025.
Restriction Requirement for U.S. Appl. No. 18/294,403 mailed Jan. 27, 2026.
Restriction Requirement for U.S. Appl. No. 18/335,579 mailed Nov. 26, 2025.
Restriction Requirement for U.S. Appl. No. 18/373,424 mailed Nov. 14, 2025.
Restriction Requirement for U.S. Appl. No. 18/376,274 mailed Dec. 10, 2025.
Restriction Requirement for U.S. Appl. No. 18/549,387 mailed Dec. 9, 2025.
Restriction Requirement for U.S. Appl. No. 18/551,492 mailed Nov. 10, 2025.
Restriction Requirement for U.S. Appl. No. 18/558,502 mailed Jan. 29, 2026.
Restriction Requirement for U.S. Appl. No. 18/569,711 mailed Jan. 6, 2026.
Restriction Requirement for U.S. Appl. No. 18/569,778 mailed Jan. 15, 2026.
Restriction Requirement for U.S. Appl. No. 18/662,216 mailed Nov. 26, 2025.
Restriction Requirement for U.S. Appl. No. 18/687,117 mailed Mar. 26, 2026.
Restriction Requirement for U.S. Appl. No. 19/237,368 mailed Dec. 18, 2025.
U.S. Appl. No. 17/051,399, filed Oct. 28, 2020.
U.S. Appl. No. 17/596,629, filed Dec. 15, 2021.
U.S. Appl. No. 17/625,941, filed Jan. 10, 2022.
U.S. Appl. No. 18/034,902, filed May 2, 2023.
U.S. Appl. No. 18/546,465, filed Aug. 15, 2023.
U.S. Appl. No. 19/127,234, filed May 5, 2025.
U.S. Appl. No. 19/179,540, filed Apr. 15, 2025.
U.S. Appl. No. 19/202,862, filed May 8, 2025.
U.S. Appl. No. 19/207,699, filed May 14, 2025.
U.S. Appl. No. 19/215,723, filed May 22, 2025.
U.S. Appl. No. 19/237,368, filed Jun. 13, 2025.
U.S. Appl. No. 19/240,380, filed Jun. 17, 2025.
U.S. Appl. No. 19/329,723, filed Sep. 16, 2025.
U.S. Appl. No. 19/337,217, filed Sep. 23, 2025.
U.S. Appl. No. 19/353,151, filed Oct. 8, 2025.
U.S. Appl. No. 19/356,506, filed Oct. 13, 2025.
U.S. Appl. No. 19/358,647, filed Oct. 15, 2025.
U.S. Appl. No. 19/370,361, filed Oct. 27, 2025.
U.S. Appl. No. 19/418,150, filed Dec. 12, 2025.
U.S. Appl. No. 19/443,729, filed Jan. 8, 2026.
U.S. Appl. No. 19/447,347, filed Jan. 13, 2026.
U.S. Appl. No. 19/451,614, filed Jan. 16, 2026.
U.S. Appl. No. 19/491,481, filed Dec. 9, 2025.
U.S. Appl. No. 19/494,631, filed Dec. 18, 2025.
U.S. Appl. No. 19/510,850, filed Feb. 12, 2026.
U.S. Appl. No. 19/513,755, filed Feb. 24, 2026.
U.S. Appl. No. 19/513,838, filed Feb. 24, 2026.
U.S. Appl. No. 19/514,100, filed Feb. 25, 2026.
U.S. Appl. No. 19/534,156, filed Feb. 9, 2026.
U.S. Appl. No. 19/535,649, filed Feb. 10, 2026.
U.S. Appl. No. 19/539,961, filed Feb. 13, 2026.
U.S. Appl. No. 19/541,655, filed Feb. 17, 2026.
U.S. Appl. No. 19/544,501, filed Feb. 19, 2026.
U.S. Appl. No. 19/554,125, filed Mar. 2, 2026.
U.S. Appl. No. 19/579,050, filed Apr. 16, 2026.
U.S. Appl. No. 19/582,525, filed Apr. 28, 2026.
U.S. Appl. No. 19/638,741, filed Apr. 3, 2026.
U.S. Appl. No. 19/657,823, filed Apr. 24, 2026.
U.S. Appl. No. 62/665,711, filed May 2, 2018.

* cited by examiner

MALE FLUID COLLECTION ASSEMBLIES AND SYSTEMS, METHODS OF USING, AND METHODS OF MANUFACTURING THE SAME

CROSS-REFERENCE TO RELATED APPLICATIONS

This application is a continuation of PCT International Application No. PCT/US2022/014285 filed on Jan. 28, 2022, the disclosure of which is incorporated herein, in its entirety, by this reference.

BACKGROUND

In various circumstances, a person or animal may have limited or impaired mobility such that typical urination processes are challenging or impossible. For example, a person may experience or have a disability that impairs mobility. A person may have restricted travel conditions such as those experienced by pilots, drivers, and workers in hazardous areas. Additionally, sometimes urine collection is needed for monitoring purposes or clinical testing.

Urinary catheters, such as a Foley catheter, can be used to address some of these circumstances, such as incontinence. Unfortunately, however, urinary catheters can be uncomfortable, painful, and can lead to complications, such as infections. Additionally, bed pans, which are receptacles used for the toileting of bedridden patients, such as those in a health care facility, are sometimes used. Bed pans, however, can be prone to discomfort, spills, and other hygiene issues.

Males who suffer the most severe consequences of urinary incontinence, such as discomfort, rashes, and sores are typically elderly and often bedbound. They also require continuous assistance to maintain hygiene. Characteristics often found in these patients: they typically lay on their back, the size of the penis often decreases with age, skin rolls containing fat tissue cause the penis to recede, often pointing upward while in a laying position, patients have difficulty reaching the penis and manipulating devices. A urine capture device should be designed with reference to these characteristics.

Available solutions are typically for use while standing up (such as cups and funnels), with a urine discharge port opposite to the distal end of the penis. Other designs such as condom-style catheters are difficult for patients to manipulate, too often they are dimensionally incompatible; and they do not stay on reliably.

Thus, there is a need for a device capable of collecting urine from a person or animal, particularly a male, comfortably and with minimal contamination of the user and/or the surrounding area.

SUMMARY

Embodiments disclosed herein are directed to male fluid collection assemblies, systems including the same, methods of manufacturing the same, and methods of using the same. In an embodiment, a fluid collection assembly is disclosed. The fluid collection assembly includes a sheath. The sheath includes a fluid impermeable barrier including a proximal region and a distal region extending from the proximal region. The proximal region exhibits a first width and the distal region exhibiting a second width that is less than the first width. The proximal region defines an opening and the distal region defines a fluid outlet. The fluid impermeable barrier at least defines a chamber. The sheath also includes at least one porous material disposed in the chamber. The fluid collection assembly also includes a base secured to or configured to be secured to the proximal region of the sheath. The base is configured to be attached to skin surrounding a penis. The base defines an aperture that corresponds to the opening of the sheath.

In an embodiment, a system is disclosed. The system includes a fluid collection assembly. The fluid collection assembly includes a sheath. The sheath includes a fluid impermeable barrier including a proximal region and a distal region extending from the proximal region. The proximal region exhibits a first width and the distal region exhibiting a second width that is less than the first width. The proximal region defines an opening and the distal region defines a fluid outlet. The fluid impermeable barrier at least defines a chamber. The sheath also includes at least one porous material disposed in the chamber. The fluid collection assembly also includes a base secured to or configured to be secured to the proximal region of the sheath. The base is configured to be attached to skin surrounding a penis. The base defines an aperture that corresponds to the opening of the sheath. The system also includes a vacuum source configured to apply a vacuum force, a fluid storage container, and at least one conduit connected to the outlet and in fluid communication with the vacuum source and the fluid storage container.

In an embodiment, a method of manufacturing a fluid collection assembly is disclosed. The method includes attaching a base to a fluid impermeable barrier of a sheath. The sheath including a fluid impermeable barrier including a proximal region and a distal region extending from the proximal region. The proximal region exhibits a first width and the distal region exhibiting a second width that is less than the first width. The proximal region defines an opening and the distal region defines a fluid outlet. The fluid impermeable barrier at least defines a chamber. The base is configured to be attached to skin surrounding a penis. The base defines an aperture that corresponds to the opening of the sheath after attaching the base to the fluid impermeable barrier. The method also includes disposing at least one porous material in the chamber.

In an embodiment, a method of using a system to collect bodily fluids from an individual is disclosed. The method includes attaching a base to skin surrounding a penis. The base secured to or configured to be secured to a sheath. The sheath includes a fluid impermeable barrier including a proximal region and a distal region extending from the proximal region. The proximal region exhibits a first width and the distal region exhibiting a second width that is less than the first width. The proximal region defines an opening and the distal region defines a fluid outlet. The fluid impermeable barrier at least defines a chamber. The sheath also includes at least one porous material disposed in the chamber.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments disclosed herein are directed to male fluid collection assemblies, systems including the same, methods of manufacturing the same, and methods of using the same. An example fluid collection assembly includes a sheath and a base. The sheath includes a fluid impermeable barrier having a proximal region and a distal region extending from the proximal region. The proximal region exhibits a first width and the distal region exhibits a second width that is less than the first width. The proximal region defines an opening and the distal region defines a fluid outlet. The fluid impermeable barrier defines a chamber. The sheath also includes at least one porous material disposed in the chamber. The base may be attached (e.g., permanently attached) to the sheath or the base may be configured to be secured to the sheath at some time period in the future. The base defines an aperture that is aligned with the opening when the base is attached to the sheath. The base is configured to be secured to a region about a penis of an individual with the aperture positioned over the penis.

An example method of using the fluid collection assembly includes securing the base to the region about the penis of an individual. The base is positioned on the individual such that the penis extends through (e.g., the penis is not buried) or is adjacent to (e.g., the penis is buried) the aperture defined by the base. If sheath is not already attached to the base, the sheath may also be attached to the base. For example, the sheath may be attached to the base before, during, or after securing the base to the region about the penis. After the base is secured to the region about the penis and the sheath is attached to the base, the individual may discharge bodily fluids from the penis. The bodily fluids may include urine or sweat. The bodily fluids enter the chamber of the sheath. The porous material may receive at least some of the bodily fluids that enter the chamber and direct the bodily fluids towards the fluid outlet. The method may include removing the bodily fluids from the chamber through the fluid outlet, for instance, when a vacuum force is applied to the outlet via a vacuum source that is in fluid communication with the chamber. Although the fluid collection assemblies disclosed herein are discussed as being male fluid collection assemblies that are used with penises, it is noted that the fluid collection assemblies may be female fluid collection assemblies that are used to collect bodily fluids from females.

Figure 1A:
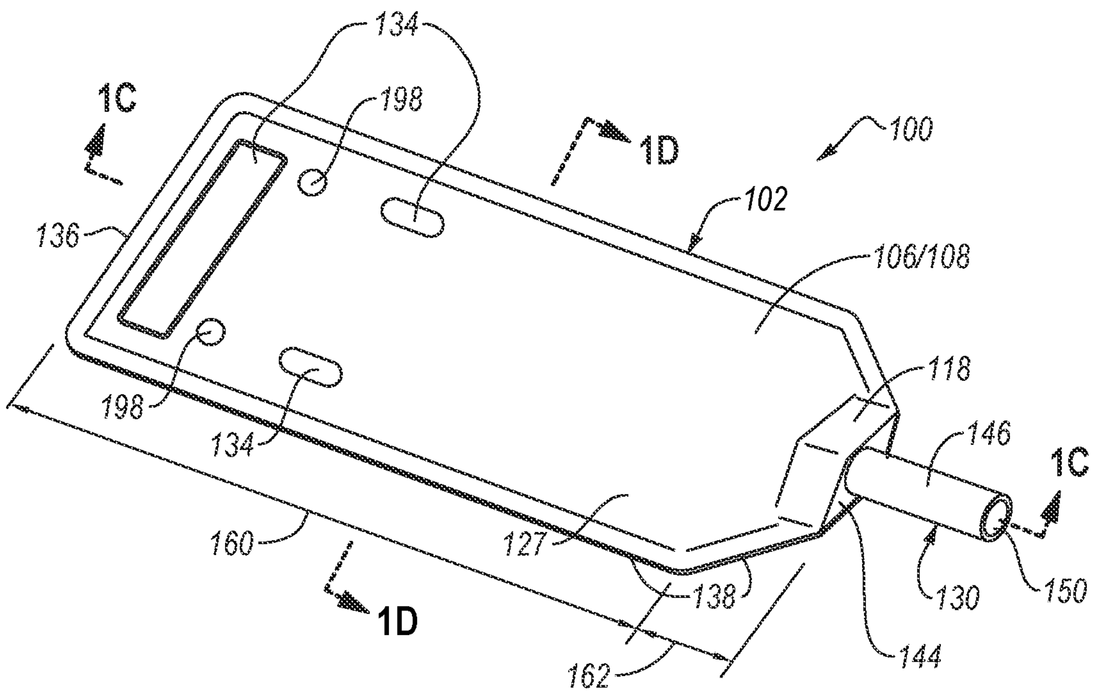
FIGS. 1A and 1B are isometric top and bottom views, respectively, of a fluid collection assembly, according to an embodiment.
Figure 1B:
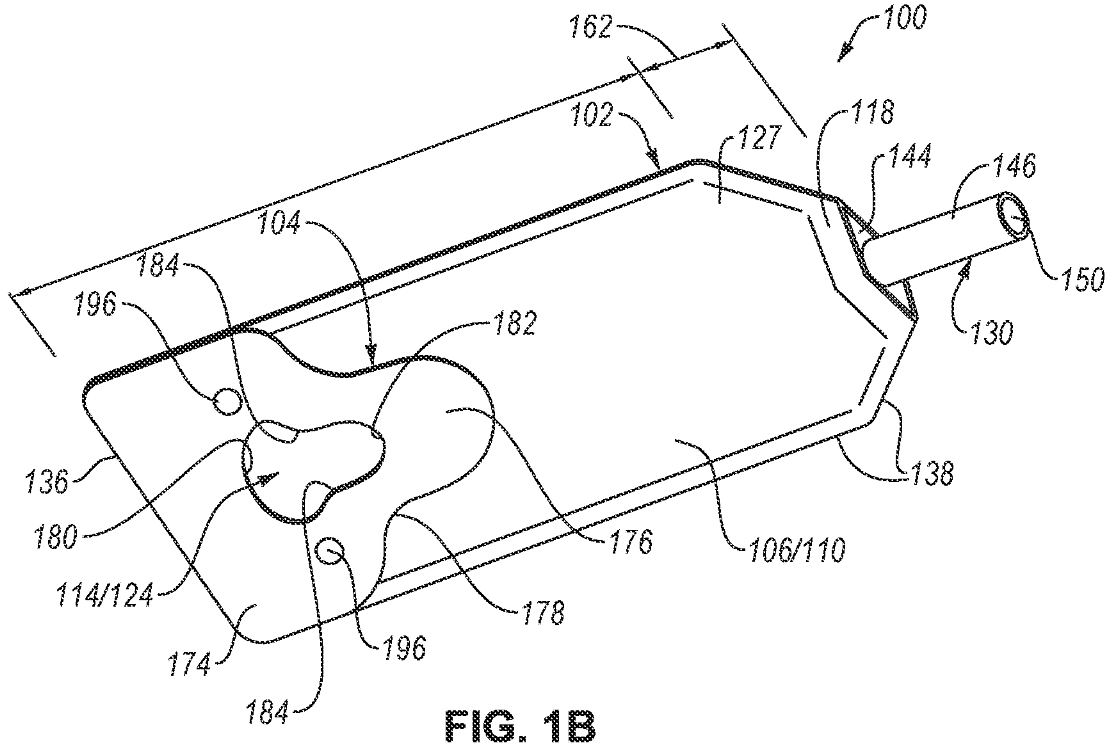
Figure 1C:
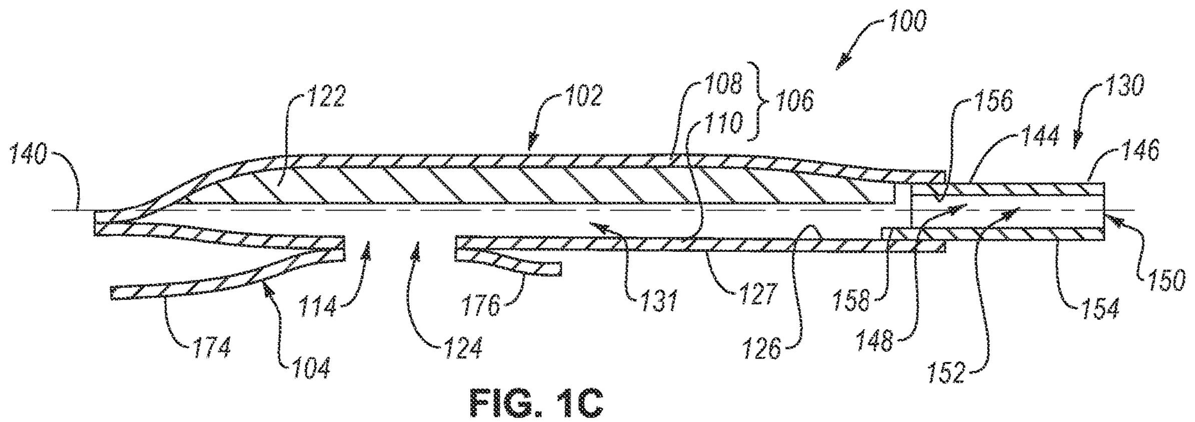
FIGS. 1C and 1D are cross-sectional schematics of the fluid collection assembly taken along planes C-C and D-D, respectively, according to any embodiment.
Figure 1D:
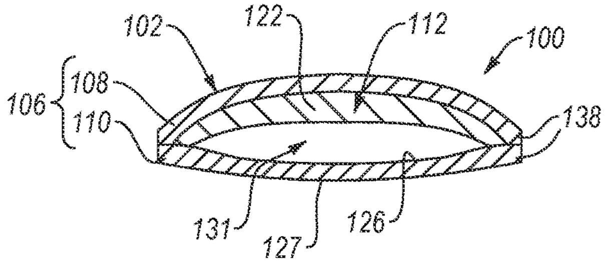
Figure 1E:
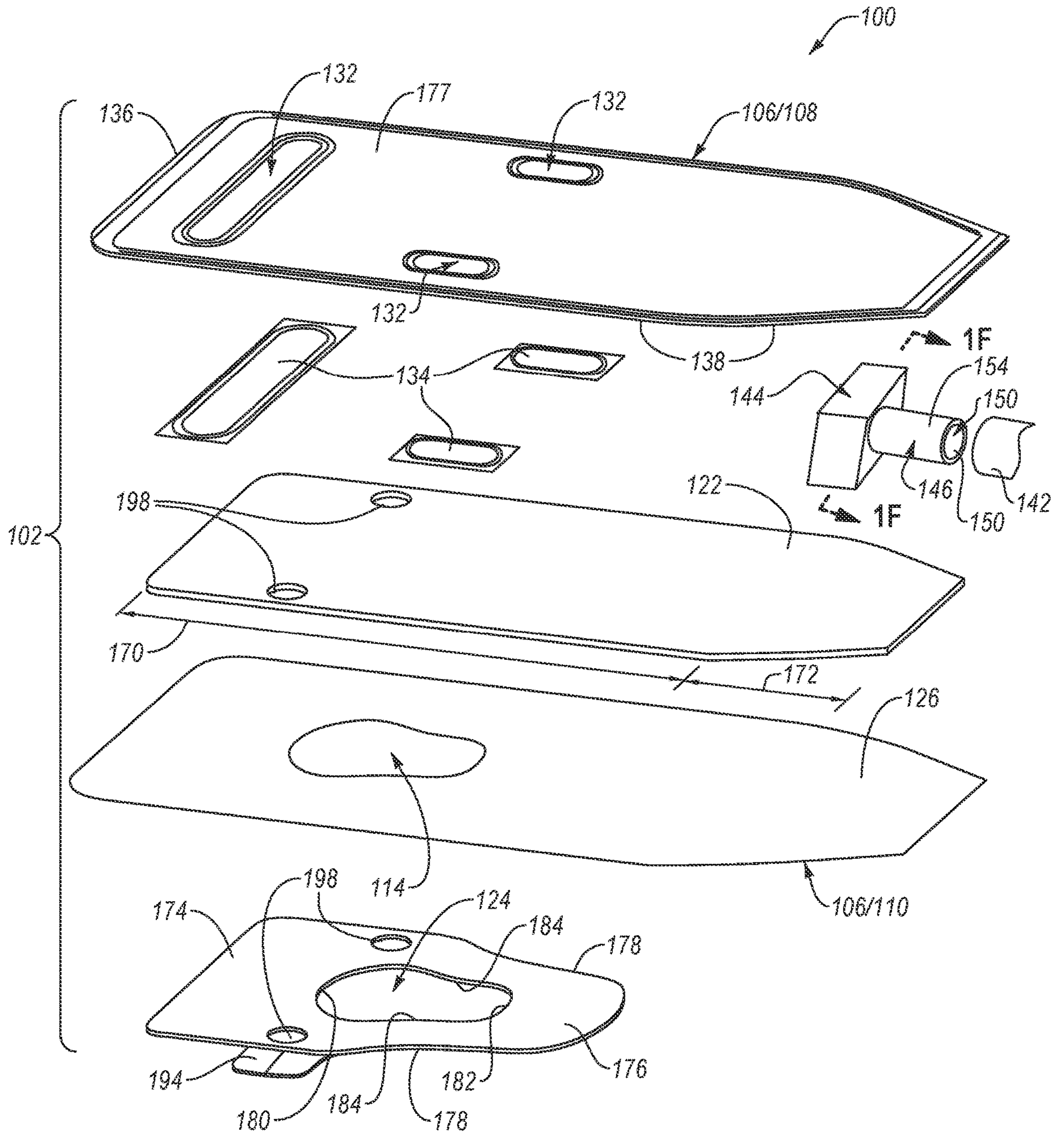
FIG. 1E is an exploded isometric view of the the fluid collection assembly shown in FIGS. 1A and 1B.

FIGS. 1A and 1B are isometric top and bottom views, respectively, of a fluid collection assembly 100, according to an embodiment. FIGS. 1C and 1D are cross-sectional schematics of the fluid collection assembly 100 taken along planes C-C and D-D, respectively, according to any embodiment. FIG. 1E is an exploded view of the fluid collection assembly 100. The fluid collection assembly 100 includes a sheath 102 and a base 104. In an embodiment, the sheath 102 includes a fluid impermeable barrier 106 that is at least partially formed from a first panel 108 attached to a second panel 110. In an embodiment, as illustrated, the first panel 108 and the second panel 110 are distinct sheets. The fluid impermeable barrier 106 also defines a chamber 112 between the first panel 108 and the second panel, an opening 114, and a fluid outlet 118. The sheath 102 also includes at least one porous material 122 disposed in the chamber 112. The base 104 includes an aperture 124. The base 104 is attached to the proximal region 160 of the fluid impermeable barrier 106 such that the aperture 124 is aligned with the opening 114.

The inner surfaces 126 of the fluid impermeable barrier 106 (e.g., inner surfaces of the first and second panels 108, 110) at least partially defines the chamber 112 within the fluid collection assembly 100. The fluid impermeable barrier 106 temporarily stores the bodily fluids in the chamber 112.

The fluid impermeable barrier 106 may be formed of any suitable fluid impermeable material(s), such as a fluid impermeable polymer (e.g., silicone, polypropylene, polyethylene, polyethylene terephthalate, polyurethane, polyethylene, polyvinyl chloride, a polycarbonate, etc.), a metal film, natural rubber, another suitable material, or combinations thereof. As such, the fluid impermeable barrier 106 substantially prevents the bodily fluids from passing through the fluid impermeable barrier 106. In an example, the fluid impermeable barrier 106 may be air permeable and fluid impermeable thus preventing leaks while allowing air flow through the chamber 112 when a vacuum force is applied thereto (i.e., the chamber 112 remains at about atmospheric pressure thereby preventing the vacuum force from causing a hickie or kinking the conduit 142). In such an example, the fluid impermeable barrier 106 may be formed of a hydrophobic material that defines a plurality of pores. At least one or more portions of at least an outer surface 127 of the fluid impermeable barrier 106 may be formed from a soft and/or smooth material, thereby reducing chaffing.

In an embodiment, the fluid impermeable barrier 106 is formed from polyurethane, such as formed only from polyurethane. It has been found in clinical trials that forming the fluid impermeable barrier 106 from polyurethane improves the functionality of the fluid collection assembly 100. For example, the fluid impermeable barrier 106 may exhibit a flexibility when formed from polyurethane that is greater than when the fluid impermeable barrier 106 is formed from another material. The increased flexibility of the fluid impermeable barrier 106 formed from the polyurethane makes it easier to attach the fluid collection assembly 100 to the individual and maintain the fluid collection assembly 100 attached to the individual. The increased flexibility of the fluid impermeable barrier 106 formed from the polyurethane also help allow the fluid collection assembly 100 to conform to the individual and/or fit underneath the clothing of the individual thereby increasing patient comfort. The increased flexibility of the fluid impermeable barrier 106 prevents or at least inhibits corners formed in the fluid impermeable barrier 106, if present, from uncomfortably pressing into the individual using the fluid collection assembly 100 thereby making the fluid collection assembly 100 more comfortable to use. The polyurethane may also remain flexible when welded or otherwise have seals formed therein. It has also been found that individuals using the fluid collection assembly 100 describe the fluid impermeable barrier 106 formed from polyurethane as being more smooth than when the fluid impermeable barrier 106 is formed from other materials. The smoother feel of the fluid impermeable barrier 106 formed from polyurethane makes wearing the fluid collection assembly 100 more comfortable. It has also been found that forming the fluid impermeable barrier 106 from the polyurethane allows the fluid impermeable barrier 106 to be bent (e.g., crumpled, wrinkled, etc.) more quietly than if the fluid impermeable barrier 106 was formed from another material. The improved quietness of the fluid impermeable barrier 106 allows the fluid collection assembly 100 to be used more discreetly. For example, movement of an individual using the fluid collection assembly 100 is likely to cause the fluid impermeable barrier 106 to bend. Forming the fluid impermeable barrier 106 from polyurethane allows the individual to move more substantially without the fluid impermeable barrier 106 generating noise. Finally, it has been found that the fluid impermeable barrier 106 that includes polyurethane is able to be welded to a variety of materials thereby facilitating attachment of the base 104, the vents 134, and the port 130 to the fluid impermeable barrier 106.

In an embodiment, at least one of the first panel 108 or the second panel 110 is formed from an at least partially transparent fluid impermeable material, such as polyethylene, polypropylene, polyurethane, polycarbonate, or polyvinyl chloride. Forming at least one of the first panel 108 or the second panel 110 from an at least partially transparent fluid impermeable material allows a person (e.g., medical practitioner) to examiner the penis. In some embodiments, both the first panel 108 and the second panel 110 are formed from at least partially transparent fluid impermeable material. For example, some conventional fluid collection assemblies that include a sheath and a base may allow the sheath to be reversibly detached from the base after the base is secured to the region about the penis. Detaching the sheath from the base allows the person to examine the penis. However, configuring the sheath to be detachable from the base may allow leaks between the sheath and the base. As previously discussed, the sheath 102 may be permanently attached to the base 104, which substantially prevents leaks between the sheath 102 and the base 104 when the base 104 is appropriately attached to the sheath 102 (e.g., no wrinkles were allowed to form between the sheath 102 and base 104). Selecting at least one of the first panel 108 or the second panel 110 to be formed from an at least partially transparent impermeable material allows the penis to be examined without detaching the entire fluid collection assembly 100 from the region about the penis. For example, the chamber 112 may include a penis receiving area 131 that is configured to receive the penis of the individual when the penis extends into the chamber 112. The penis receiving area 131 may be defined by at least the porous material 122 and at least a portion of the at least partially transparent material of the first panel 108 and/or the second panel 110. In other words, the porous material 122 is positioned in the chamber 112 such that the porous material is not positioned between the penis and at least a portion of the transparent portion of the first panel 108 and/or second panel 110 when the penis is inserted into the chamber 112 through the opening 114. The porous material 122 is generally not transparent and, thus, the portion of the at least partially transparent material of the first panel 108 and/or the second panel 110 that defines the penis receiving area 131 forms a window which allows the person to view into the penis receiving area 131 and examine the penis.

In an embodiment, the second panel 110 is at least partially formed from the at least partially transparent material and forms the window that allows the person to view into the penis receiving area 131. Further, the porous material 122 is positioned between the penis receiving area 131 and at least a portion of the first panel 108. Such an embodiment may help maintain the dignity of the individual using the fluid collection assembly 100. For example, during use, the second panel 110 is generally adjacent to the individual, such as adjacent to the thighs and/or perineum. Thus, the second panel 110 is generally obscured during use and a person cannot view the penis without first lifting the sheath 102 away from the individual. Meanwhile, the first panel 108 may face away from the individual and be more easily viewable than the second panel 110. However, a person (e.g., a passerby, a visitor, etc.) cannot view the penis through the first panel 108 because the porous material 122 is not transparent and/or the first panel 108 is formed from a non-transparent material. Thus, in such an embodiment, the first panel 108 and/or the porous material 122 prevent person(s) from viewing the penis unless such examination is necessary, thereby preserving the dignity of the individual using the fluid collection assembly 100. In an embodiment, the first panel 108 is formed from the at least partially transparent material and forms the window that allows the person to view into the penis receiving area 131. Further, the porous material 122 is positioned between the penis receiving area 131 and at least a portion of the second panel 110. In such an embodiment, the person does not need to perform the additional act of lifting the sheath 102 to view into the penis receiving area 131 but may not maintain the dignity of the individual using the fluid collection assembly 100 since passersby may also view into the penis receiving area 131.

As previously discussed, at least a portion of the first panel 108 and at least a portion of the second panel 110 are attached together. In an embodiment, as shown, the first and second panels 108, 110 are attached together along at least a portion of the outer edges thereof (e.g., the top and lateral edges 136, 138). In such an embodiment, the first and second panels 108, 110 are attached using any suitable technique, such as with an adhesive, sewing, heat sealing, impulse heating, direct heating, radio frequency ("RF") welding, ultrasonic ("US") welding, or any other technique. In a particular embodiment, the first and second panels 108 are attached together using impulse heating since impulse heating is quick and is effective at attaching polyurethane panels together. As will be discussed in more detail below, forming the fluid impermeable barrier 106 from the first panel 108 and the second panel 110 may improve the rate of manufacturing the fluid collection assembly 100, especially when the first panel 108 and the second panel 110 are attached together using a non-sewing technique.

In an embodiment, the fluid impermeable barrier 106 defines one or more orifices 132 extending therethrough. The sheath 102 includes one or more vents 134 attached to the fluid impermeable barrier 106 that extend across the one or more orifices 132. The vents 134 are configured to allow air to flow therethrough while preventing water (a major constituent of bodily fluids) from flowing therethrough. The vents 134 facilitate air flow through the chamber 112. For example, as previously discussed, a vacuum may be provided to the chamber 112 from a vacuum source. The vacuum may pull air through the vents 134, thereby allowing air flow from the vents 134 to the fluid outlet 118. The air flow from the vents 134 helps move bodily fluids towards the fluid outlet 118. The vents 134 also prevent the vacuum applied to the chamber 112 from bursting small superficial blood vessels (e.g., cause a hickie) in or otherwise damage the penis or the area about the penis.

The vents 134 may include a porous hydrophobic material. The pores defined by the porous hydrophobic material may be interconnected thereby allowing air to flow through the vents 134. The hydrophobic properties of the porous hydrophobic material may prevent water from flowing through the vents 134. In an example, the average size of the pores (e.g., the average maximum lateral dimension of the pores) of the porous hydrophobic material may be selected to be about 1 μm or greater, about 5 μm or greater, about 10 μm or greater, about 20 μm or greater, about 30 μm or greater, about 40 μm or greater, about 50 μm or greater, about 60 μm or greater, about 80 μm or greater, about 100 μm or greater, about 125 μm or greater, about 150 μm or greater, about 175 μm or greater, about 200 μm or greater, about 250 μm or greater, about 300 μm or greater, about 400 μm or greater, about 500 μm or greater, about 1 mm or less, about 750 μm or less, about 500 μm or less, or in ranges of about 1 μm to about 10 μm, about 5 μm to about 20 μm, about 10 μm to about 30 μm, about 20 μm to about 40 μm, about 30 μm to about 50 μm, about 40 μm to about 60 μm, about 50 μm to about 80 μm, about 60 μm to about 100 μm, about 80 μm to about 125 μm, about 100 μm to about 150 μm, about 125 μm to about 175 μm, about 150 μm to about 200 μm, about 175 μm to about 250 μm, about 200 μm to about 300 μm, about 250 μm to about 400 μm, about 300 μm to about 500 μm, about 400 μm to about 750 μm, or about 500 μm to about 1 mm. In an example, the porous hydrophobic material may exhibit a contact angle with water that is greater than 90°, such as in ranges of about 90° to about 110°, about 100° to about 120°, about 110° to about 130°, about 120° to about 140°, about 130° to about 150°, about 140° to about 160°, about 150° to about 170°, or about 160° to 180°. Generally, the size of the pores is dependent on the hydrophobicity of the porous hydrophobic material and vice versa. For example, increasing the hydrophobicity of the porous hydrophobic material allows the size of the pores to be increased.

In an embodiment, the vents 134 may include a porous polytetrafluoroethylene ("PTFE") layer. It is currently believed that the porous PTFE layer is exceptionally effectively at allowing air to flow therethrough while preventing water from flow therethrough even when the porous PTFE layer is exposed to acidic bodily fluids. However, porous PTFE is difficult to weld to other materials, such as polyurethane. As such, the porous PTFE layer may be attached to a substrate. The substrate may include a porous material or define one or more passageways therethrough. The substrate may be selected to be easily attached to the porous PTFE layer and the fluid impermeable barrier 106. For example, the substrate may be selected to be formed from polyvinyl chloride since polyvinyl chloride may be easily attached to the porous PTFE layer and attached to the fluid impermeable barrier 106.

In an embodiment, the orifices 132 are formed in and the vents 134 are attached to the first panel 108 of the fluid impermeable barrier 106. In such an embodiment, the orifices 132 and the vents 134 are unlikely to be covered by and contact the skin of the individual. Covering the orifices 132 and the vents 134 with the skin may prevent or at least inhibit air flow through the portions of the orifices 132 and the vents 134 at are covered by the skin. Further, an individual may find the vents 134 contacting the skin to be uncomfortable and, thus, disposing the vents 134 on the first panel 108 may make the fluid collection assembly 100 more comfortable to wear. In an embodiment, the vents 134 are attached to an interior of the first panel 108 to prevent the edges of the vents 134 from rubbing or otherwise irritating the skin of the individual.

In an embodiment, as illustrated, at least one of the orifices 132 is formed in and at least one of the vents 134 is attached to a portion of the fluid impermeable barrier 106 that is at or near to top edge 136 of the fluid impermeable barrier 106. The top edge 136 of the fluid impermeable barrier 106 may include an edge of the fluid impermeable barrier 106 that is above the opening 114 when the individual is standing and the fluid collection assembly 100 is allowed to freely hang from the pubic region of the individual. Forming the orifices 132 and attaching the vents 134 at or near the top edge 136 causes air flowing through the vents 134 to pass over the penis (thereby keeping the penis dry) and inhibits pooling of the bodily fluids near the top edge 136. In an embodiment, as illustrated, at least one of the orifices 132 is formed in and at least one of the vents 134 is attached to a portion of the fluid impermeable barrier 106 that is at or near to a lateral edge 138 of the fluid impermeable barrier 106. The lateral edge 138 of the fluid impermeable barrier 106 may include an edge of the fluid impermeable barrier 106 that extends from or near the top edge 136. Generally, air preferentially flows in a path extending from the vents 134 towards the fluid outlet 118. When the vents 134 are spaced from the lateral edges 138 and/or at or near the top edge 136, the preferential air flow from these vents 134 may cause at least some of the portions of the chamber 112 adjacent to the lateral edges 138 to have minimal air flow therethrough. Positioning the orifices 132 and the vents 134 at or near the lateral edges 138 may increase the air flow through the portions of the chamber 112 adjacent to the lateral edges 138 thereby preventing or at least inhibiting pooling of bodily fluids in such portions of the chamber 112.

In an embodiment, the orifices 132 and the vents 134 may exhibit an elongated shape. In an example, the orifices 132 and the vents 134 at or near the top edge 136 may exhibit an elongated shape that is generally parallel to the top edge 136 and/or generally perpendicular to a longitudinal axis 140 of the fluid collection assembly 100. In such an example, the elongated shape of the orifices 132 and the vents 134 cause the air to preferentially flow through a greater percentage of the chamber 112 than if the orifices 132 and the vents 134 did not exhibit an elongated shape and/or were oriented differently. In an example, the orifices 132 and the vents 134 at or near the lateral edge 138 may exhibit an elongated shape that is generally parallel to the lateral edge 138 and/or generally parallel to the longitudinal axis 140 of the fluid collection assembly 100. In such an example, the elongated shape of the orifices 132 and the vents 134 may cause the air to preferentially flow through a greater percentage of the chamber 112 (e.g., the portions of the chamber 112 adjacent to the lateral edges 138) than if the orifices 132 and the vents 134 did not exhibit an elongated shape and/or were oriented differently.

The opening 114 defined by the fluid impermeable barrier 106 provides an ingress route for fluids to enter the chamber 112 when the penis is a buried penis and allow the penis to enter the chamber 112 (e.g., the penis receiving area 131) when the penis is not buried. The opening 114 may be defined by the fluid impermeable barrier 106 (e.g., an inner edge of the fluid impermeable barrier 106). For example, the opening 114 is formed in and extends through the fluid impermeable barrier 106, from the outer surface 127 to the inner surface 126, thereby enabling bodily fluids to enter the chamber 112 from outside of the fluid collection assembly 100.

In an embodiment, the second panel 110 defines the entirety of the opening 114. For example, the opening 114 is a cutout defined by the second panel 110 that is spaced from the outer periphery (e.g., edges) of the second panel 110. In such an example, the second panel 110 may exhibit a shape that substantially corresponds to the shape of the first panel 108 which may facilitate attaching the first panel 108 to the second panel 110 along the outer periphery thereof. It also allows the first panel 108 and the second panel 110 to lie substantially flat when the penis is not in the chamber 112 and the sheath 102 is lying on a flat surface. The ability of the first and second panels 108, 110 to lie substantially flat may make wearing the fluid collection assembly 100 more discrete and inhibit pooling of bodily fluids against the individual. However, in some embodiments, the opening 114 is not spaced from the outer periphery of the second panel 110. In such embodiments, the opening 114 may be a cutout extending inwardly from at least one outer periphery of the second panel 110. Other examples of forming the opening 114 in the second panel 110 are disclosed in International Patent Application No. PCT/US2021/039866 filed on Jun. 30, 2021, the disclosure of which is incorporated herein, in its entirety, by this reference.

As previously discussed, the fluid impermeable barrier 106 includes a proximal region 160 and a distal region 162 extending from the proximal region 160, for example, to the fluid outlet 118 (e.g., to the port 130). The proximal region 160 may define the opening 114 and the distal region 162 may define the fluid outlet 118. Both the proximal region 160 and the distal region 162 define the chamber 112.

In an embodiment, the fluid impermeable barrier 106 exhibits a generally bullet shape. As used, herein, the fluid impermeable barrier 106 exhibits the generally bullet shape when the proximal region 160 of the fluid impermeable barrier 106 exhibits a substantially constant first width and the distal region 162 of the fluid impermeable barrier 106 exhibits a second width that is less than the first width. The first and second widths may be measured perpendicularly to the longitudinal axis 140 and may be greater than a thickness of the sheath 102 when the sheath 102 lies on a flat surface. The generally bullet shape of the fluid impermeable barrier 106 facilitates operation of the fluid collection assembly 100 while making the sheath 102 more comfortable. For example, the substantially constant first width maintains contact with the upper portions of the thighs of the individual thereby maintaining the position of the fluid collection assembly 100. Also, the substantially constant first width makes it easier for the penis to become erect since the substantially constant first width inhibits the sheath 102 falling between the thighs of the individual and the erect penis from lifting the portions of the sheath 102 that fell between the thighs. The decreased second width makes the sheath 102 thinner thereby allowing the portions of the sheath 102 that are less likely to receive the penis to drop between the thighs of the individual. This drop allows gravity to assist in moving the bodily fluids towards the fluid outlet 118. The decreased second width also funnels the bodily fluids towards the fluid outlet 118 and the port 130.

In an embodiment, the second width of the distal region 162 may vary (e.g., decrease) along a length of the distal region 162 measured perpendicularly to the longitudinal axis 140. In an example, the second width of the distal region 162 may decrease at a constant rate from the proximal region 160 towards (e.g., to) the fluid outlet 118. The constant rate at which the second width decreases causes the lateral edges 138 of the fluid impermeable barrier 106 that defines the distal region 162 to be straight. The straight lateral edges 138 may form corners at the intersection between the proximal and distal regions 160, 162 that may uncomfortably press into the individual. In an example, the second width of the distal region 162 may decrease at a variable (e.g., increasing) rate from the proximal region 160 towards (e.g., to) the fluid outlet 118. The variable rate at which the second width decreases causes the lateral edges 138 of the fluid impermeable barrier 106 that defines the distal region 162 to be curved, such as convexly curved. The curved lateral edges 138 may prevent the formation of corners that may press into the individual thereby making the fluid collection assembly 100 more comfortable than if the lateral edges 138 of the distal region 162 were straight. However, it is noted that the air flow through the distal region 162 may be more uniform when the lateral edges 138 of the distal region 162 are straight instead of curved.

It is noted that the fluid impermeable barrier 106 may exhibit a shape other than the generally bullet shape. In an example, the fluid impermeable barrier 106 may exhibit a generally rectangular shape, as discussed in more detail in International Patent Application No. PCT/US2021/039866 filed on Jun. 30, 2021, the disclosure of which was previously incorporated herein. In an example, the fluid impermeable barrier 106 may exhibit a generally triangular shape, a semi-oval shape, or any other suitable shape.

The fluid impermeable barrier 106 defines a fluid outlet 118. The fluid outlet 118 may be formed from a portion of the first panel 108 and the second panel 110 that are not attached together. In an embodiment, not shown, the fluid outlet 118 is configured to be directly attached to a conduit 142. In such an embodiment, the conduit 142 may be at least partially disposed in the chamber 112 or otherwise in fluid communication with the chamber 112 through the fluid outlet 118. The fluid outlet 118 may be sized and shaped to form an at least substantially fluid tight seal against the conduit 142, thereby substantially preventing the bodily fluids from escaping the chamber 112. The conduit 142 may be attached to the fluid outlet 118 (e.g., to the first and second panels 108, 110) using an adhesive, a weld, an interference or friction fit, or otherwise bonding the fluid outlet 118 to the fluid outlet 118. Attaching the conduit 142 to the fluid outlet 118 may prevent leaks and may prevent the conduit 142 from inadvertently becoming detached from the fluid outlet 118. In an example, the conduit 142 may be attached to the fluid outlet 118 in the same manufacturing step that attaches the first and second panels 108, 110 together. In an embodiment, as shown, the fluid outlet 118 is configured to be indirectly attached to the conduit 142. In such an embodiment, the sheath 102 may include a port 130 that is directly attached to the fluid impermeable barrier 106 and configured to be attached to the conduit 142.

Figure 1F:
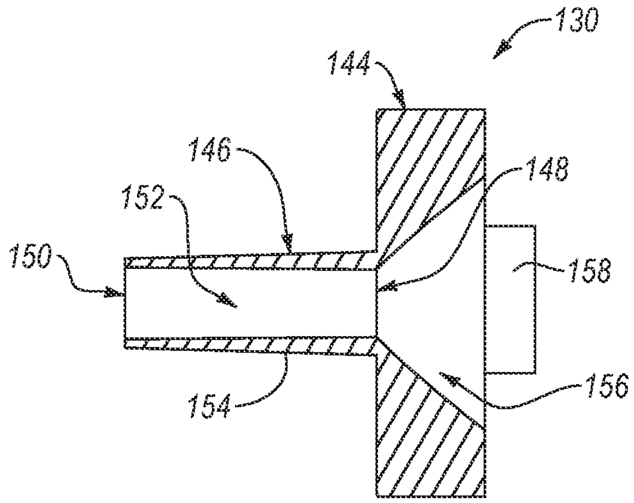
FIG. 1F is a cross-sectional view of the port taken along plane 1F-1F shown in FIG. 1A, according to an embodiment.

FIG. 1F is a cross-sectional view of the port 130 taken along plane 1F-1F shown in FIG. 1E, according to an embodiment. The port 130 includes a first part 144 and a second part 146. The first part 144 is configured to be attached to the fluid impermeable barrier 106 and, optionally, to be at least partially disposed in the chamber 112. The second part 146 is configured to attach to the conduit 142. The first part 144 defines an inlet 148 and the second part 146 defines an outlet 150 of the port 130 that is downstream from the inlet 148. The port 130 also defines a channel 152 extending from the inlet 148 to the outlet 150. It is noted that the inlet 148 refers to the inlet of the channel 152 and not necessarily the inlet of the port 130. In an example, the inlet 148 may be the inlet of both the port 130 and the channel 152 when the port 130 does not include a sink 156. In an example, as illustrated, the inlet 148 may not be the inlet of the port 130 when the port 130 includes sink 156 since the sink 156 forms the inlet of the port 130.

The first part 144 of the port 130 may be attached to the fluid impermeable barrier 106 using any suitable technique. In an embodiment, the first part 144 is disposed between the first and second panels 108, 110 before attaching the first part 144 to the fluid impermeable barrier 106. In such an embodiment, the first part 144 abuts and is attached to the inner surface 126 of the fluid impermeable barrier 106. In an embodiment, the first part 144 is attached to the fluid impermeable barrier 106 using at least one of an adhesive, impulse heating, direct heating, US welding, RF welding, any other attachment technique disclosed herein, or another other suitable attachment technique.

At least the second part 146 exhibits a rigidity that is greater than the fluid impermeable barrier 106. The second part 146 may exhibit a rigidity that is greater than the fluid impermeable barrier 106 because at least one of second part 146 exhibits a thickness that is greater than the fluid impermeable barrier 106 or at least a portion of the second part 146 is formed from a material exhibiting a Young's modulus (i.e., modulus of elasticity) that is greater than a Young's modulus of a material forming at least a portion of the fluid impermeable barrier 106. The increased rigidity of the second part 146 relative to the fluid impermeable barrier 106 allows the second part 146 to be attached to the conduit 142 using techniques that may be difficult or impossible to do when the conduit 142 is directly attached to the fluid impermeable barrier 106. In an example, the conduit 142 may be attached to the second part 146 using an interference fit which may be difficult or impossible to do when the conduit 142 is directly attached to the fluid impermeable barrier 106. In such an example, a surface of the second part 146 that is configured to abut the conduit 142 is tapered. The tapered surface of the second part 146 may make inserting the second part 146 into the conduit 142 easier when the second part 146 forms a male connector and may make receiving the conduit 142 into the second part 146 easier when the second part 146 forms a female connector. The tapered surface of the second part 146 also allows the strength of the interference fit between the second part 146 and the conduit 142 to be controlled by controlling how much the second part 146 is inserted into the conduit 142 or how much the conduit 142 is inserted into the second part 146. In an example, not shown, a surface of the second part 146 is configured to be threadedly attached to the conduit 142 which may be difficult or impossible to do when the conduit 142 is directly attached to the fluid impermeable barrier 106. In such an example, the second part 146 may include one or more helically extending ridges extending from a surface of the second part 146 that contacts or is closest to the conduit 142. It is noted that the surface of the second part 146 that includes the threads and/or the threads may be tapered. In an example, not shown, a surface of the second part 146 that contacts or is closest to the conduit 142 may include circumferentially extending ridges. It is noted that the surface of the second part 146 that includes the ridges and/or the ridges may be tapered.

In an embodiment, at least the second part 146 exhibits a rigidity that is greater than the conduit 142. The second part 146 may exhibit a rigidity that is greater than the conduit 142 because at least one of the second part 146 exhibits a thickness that is greater than the conduit 142 or at least a portion of the second part 146 is formed from a material exhibiting a Young's modulus that is greater than a Young's modulus of a material forming at least a portion of the conduit 142. The increased rigidity of the second part 146 prevents collapse of the channel 152. For example, it has been found that, in certain circumstances, directly attaching the conduit 142 to the fluid impermeable barrier 106 may cause the portions of the conduit 142 attached to the fluid impermeable barrier 106 to at least partially collapse when a strong vacuum is applied to the chamber 112. However, the increased rigidity of the port 130 prevents such collapse.

In an embodiment, the first part 144 exhibits a rigidity that is greater than the fluid impermeable barrier 106 and/or the conduit 142. For example, the first part 144 may exhibit a rigidity that is comparable to the second part 146. The increased rigidity of the first part 144 prevents collapse of the inlet 148, any portions of the channel 152 defined thereby, and the sink 156. The increased rigidity of the first part 144 may also make attaching the port 130 to the first part 144 easier since pressure may be applied to the first part 144 during the attachment process substantially without deforming the first part 144.

The first part 144 may exhibit a shape that is different than the second part 146. For example, the first part 144 may exhibit a first elongated shape that extend in a direction that is generally perpendicular to the longitudinal axis 140 and the second part 146 may exhibit a second elongated shape (e.g., generally cylindrical shape) that extends generally parallel to the longitudinal axis 140. The first elongated shape of the first part 144 may strengthen the attachment between the first part 144 and the fluid impermeable barrier 106 by increasing the surface area of the first part 144 that is attached to the fluid impermeable barrier 106. The first elongated shape of the first part 144 also prevents or at least inhibits twisting of the sheath 102. Examples of the first elongated shape include a generally rectangular cross-sectional shape, a generally oval cross-sectional shape, a generally elliptical cross-sectional shape, or a generally diamond cross-sectional shape. In a particular example, the first elongated shape is a generally diamond cross-sectional shape since the relatively sharp corners of the generally diamond cross-sectional shape that are furthest spaced from the second part 146 facilitate attaching the fluid impermeable barrier 106 to the first part 144 without forming a gap between the first part 144, the first panel 108, and the second panel 110 compared to a more rounded corner. In a particular example, the first elongated shape included rounded corners since the rounded corners are less likely to uncomfortably press into the individual than sharp corners. The second elongated shape of the second part 146 that extends parallel to the longitudinal axis 140 may facilitate attachment to the conduit 142.

The first part 144 may exhibit a first maximum thickness and the second part 146 may exhibit a second maximum thickness. As discussed in more detail elsewhere, the sheath 102 is configured to lie substantially flat when disposed on a flat surface which allows the fluid collection assembly 100 to be worn discretely, prevents or at least inhibits pooling of bodily fluids in the chamber 112, and allows the fluid collection assembly 100 to be used with buried penises. It is noted that "substantially flat" allows for deviations that generally do not prevent the fluid collection assembly 100 from being worn discretely, still inhibits pooling of bodily fluids, and allows the fluid collection assembly 100 to be used by a buried penis, such as deviations caused by the port 130, the vents 134, or minor bulges or waves formed in the fluid impermeable barrier 106. Generally, the port 130 is configured to minimize the first maximum thickness and the second maximum thickness thereby preventing or at least inhibiting the ability of the sheath 102 to lay flat. The second maximum thickness is generally dictated by the need to attach the conduit 142 to the second part 146. For example, the second maximum thickness may need to be slightly greater than the inner diameter of the conduit 142 when the second part 146 is a male connector and greater than the outer diameter of the conduit 142 when the second part 146 is a female connector. In an particular example, the second part 146 is a male connector since the second maximum thickness of the second part 146 is smaller when the second part 146 is a male connector than when the second part 146 is a female connector. It is noted that, when the second part 146 is a male connector, the second part 146 has less of an adverse effect on the ability of the sheath 102 to lay flat than if the conduit 142 is directly attached to the fluid impermeable barrier 106 since the second maximum thickness may be less than an outer diameter of the conduit 142.

Generally, the first maximum thickness of the first part 144 is substantially equal to or less than the second maximum thickness to minimize the adverse effect that the first part 144 has on the ability of the sheath 102 to lay flat. In an example, when the second maximum thickness is at or near an intersection between the first and second parts 144, 146, the first maximum thickness may be substantially equal to the second maximum thickness to prevent formation of corners that may press uncomfortably into the individual. The second maximum thickness may be at or near the intersection between the first and second parts 144, 146 when the outer surface 154 of the second part 146 is tapered.

In an embodiment, the first maximum thickness of the first part 144 is greater than a collective thickness of the fluid impermeable barrier 106 (e.g., the collective thickness of the first and second panels 108, 110) and the porous material 122. The increased thickness of the first maximum thickness of the first part 144 relative to the collective thickness of the fluid impermeable barrier 106 and the porous material 122 prevents the sheath 102 from lying flat at or near the port 130. However, it is noted that the high flexibility of the fluid impermeable barrier 106, especially when the fluid impermeable barrier 106 is formed from polyurethane, minimizes the percentage of the sheath 102 adjacent to the port 130 that does not lie flat. Further, the first part 144 is at least one of spaced from the opening 114 which prevents the first maximum thickness from affecting the ability of the fluid collection assembly 100 to be used with a buried penis, is located at the greatest air flow which inhibits pooling of bodily fluids, or the first maximum thickness is less than the maximum thickness of the conduit 142 thereby causing the conduit 142 to more adversely affect the ability to use the fluid collection assembly 100 discretely than the port 130. In an example, the first maximum thickness may be greater than the collective thickness of the fluid impermeable barrier 106 and the porous material 122 by about 500% (i.e., 5 times greater) or less, about 400% or less, about 300% or less, about 200% or less, or about 150% or less. It is noted that the first maximum thickness may be larger than the collective thickness of the fluid impermeable barrier 106 and the porous material 122 to allow the inlet 148 to be sufficiently large to remove the bodily fluids from the chamber 112 and may be dictated by the size of the conduit 142.

In an embodiment, the first part 144 of the port 130 may define a sink 156 that is distinct from the inlet 148. The sink 156 is positioned upstream from the inlet 148. For example, the inlet 148 may exhibit dimension(s) (e.g., width and/or thickness) that is comparable to corresponding dimension(s) of the channel 152 are or near the intersection of the first part 144 and the second part 146. The dimension(s) of the inlet 148 are comparable to the corresponding dimension(s) of the channel 152 when the dimension(s) of the inlet 148 differ from the dimension(s) of the channel 152 by at most about ±10% or at most about ±5%. For example, as illustrated, the inlet 148 exhibits a width that is substantially the same as the width of the channel 152 at the intersection of the first and second parts 144, 146. The sink 156 exhibits a maximum dimension that is greater than a corresponding dimension(s) of the inlet 148 and is not comparable to a corresponding dimension(s) of the channel 152 at the intersection of the first and second parts 144, 146. For example, as illustrated, the sink 156 defined by the first part 144 exhibits a maximum dimension (i.e., width) that is significantly greater than the corresponding width of the inlet 148 and the corresponding width of the channel 152 at the intersection of the first and second parts 144, 146. It is noted that the wider width of the first part 144 relative to the second part 146 allows the first part 144 to define the sink 156.

The sink 156 facilitates flow of the bodily fluids through the chamber 112, into the port 130, and through the port 130. For example, the wider dimension(s) of the sink 156 relative to the inlet 148 makes it easier for the bodily fluids to enter the port 130 than a substantially similar port 130 that does not include the sink 156 (i.e., the inlet 148 is the inlet of the port 130). The wider width of the sink 156 relative to the inlet 148 also distributes the air flow to a greater percentage of the chamber 112 than a substantially similar port 130 that does not include the sink 156. The wider dimension(s) of the sink 156 relative to the inlet 148 increases the unoccupied volume of the port 130 than if the port 130 did not include the sink 156. The greater volume of the port 130 allows the port 130 to receive and hold a greater volume of bodily fluids thereby inhibiting oversaturation of the porous material 122 with the bodily fluids since the port 130 may temporarily store the bodily fluids in addition to the porous material 122. In other words, the sink 156 may form a fluid reservoir. Also, it has been found that the sink 156 decreases turbulent flow of the bodily fluids flowing through the port 130 than if the port 130 did not include the sink 156. The decreased turbulent flow allows the bodily fluids to flow through the port 130 at a greater rate than if the port 130 did not include the sink 156 thereby inhibiting oversaturation of the bodily fluids in the porous material 122. The decreased turbulent flow of the bodily fluids caused by the sink 156 may especially facilitate the operation of the fluid collection assembly 100 when the second port 146 forms a male connector. For example, forming the second part 146 as a male connector decreases the lateral dimension(s) (e.g., diameter) of the channel 152 which causes the lateral dimensions of the second part 146 to limit the rate at which bodily fluids are removed from the chamber 112. The decreased turbulent flow of the bodily fluids through the port 130 caused by the sink 156 helps mitigate this issue.

In an embodiment, the dimension(s) of the sink 156 are maintained substantially constant. Maintaining the dimension(s) of the sink 156 substantially constant maximizes the volume of the sink 156, and by extension the volume of the port 130, that may be a fluid reservoir. However, maintaining the dimension(s) of the sink 156 substantially constant may cause a step to form at the intersection of the inlet 148 and the sink 156 which may increase turbulent flow of the bodily fluids flowing through the port 130 than if there was not step between the inlet 148 and the sink 156. In an embodiment, as illustrated, the dimension(s) of the sink 156 may be tapered along at least a portion of the length (e.g., measured parallel to the longitudinal axis 140) of the sink 156. In other words, the dimension(s) of the sink 156 may vary along at least a portion of the length thereof. The tapered dimension(s) of the sink 156 may prevent or at least decrease the step at the intersection of the inlet 148 and the sink 156. Thus, the tapered dimension(s) may decrease turbulent flow of the bodily fluids flowing through the port 130 than if the dimension(s) of the sink 156 where maintained substantially constant. It is noted that the tapered dimension(s) of the sink 156 decreases the volume of bodily fluids that may be temporarily stored in the sink 156 and, by extension, the port 130.

Due to the flexibility of the fluid impermeable barrier 106, the sheath 102 may bend to exhibit a generally L- or U-shape which may cause the fluid impermeable barrier 106 to extend across the inlet of the port 130 (e.g., extend across the sink 156 or the inlet 148 when the port 130 does not include the sink 156). For example, during use, the fluid collection assembly 100 may be positioned on the individual such that the fluid collection assembly 100 generally extends from the pubic region of the individual towards the feet of the individual. However, in many hospitals, the vacuum source is positioned behind the bed of the individual such that the conduit 142 extends from the fluid outlet 118 towards the head of the individual when the individual is lying on the bed. As such, the conduit 142 may cause the sheath 102 to bend and exhibit the generally L- or U-shape. It has been found that the fluid impermeable barrier 106 may obstruct the inlet of the port 130 thereby preventing or inhibiting bodily fluids entering the port 130 when the sheath 102 bends and exhibits the generally L- or U-shape. As such, in some embodiments, the port 130 may include at least one tab 158 extending from the first part 144 into the chamber 112.

The tab 158 extending from the first part 144 increases the likelihood that a passageway is formed that allows bodily fluids to flow to the port 130 even when the sheath 102 bends and exhibits the generally L- or U-shape. In other words, the tab 158 may allow bodily fluids to continue to flow into the port 130 and/or increase the rate at which the bodily fluids may flow into the port 130 when the sheath 102 is bent.

The tab 158 may extend from the first part 144 by a distance that is about 2 mm or more, about 3 mm or more, about 4 mm or more, about 5 mm or more, about 6 mm or more, about 7 mm or more, about 8 mm or more, about 9 mm or more, about 1 cm or more, about 1.25 cm or more, about 1.5 cm or more, or in ranges of about 1 mm to about 3 mm, about 2 mm to about 4 mm, about 3 mm to about 5 mm, about 4 mm to about 6 mm, about 5 mm to about 7 mm, about 6 mm to about 8 mm, about 7 mm to about 9 mm, about 8 mm to about 1 cm, about 9 mm to about 1.25 cm, or about 1 cm to about 1.5 cm. Generally, the ability of the tab 158 to allow bodily fluids to continue to flow into the port 130 and/or increase the rate at which the bodily fluids may flow into the port 130 when the sheath 102 is bent is improved as the distance that the tab 158 extends from the first part 144 is increased. However, increasing the distance that the tab 158 extends from the first part 144 increases the likelihood that the tab 158 uncomfortably presses into the individual, for example, when the sheath 102 is bent. The likelihood that the tab 158 uncomfortably presses into the individual may be mitigated by cushioning the tab 158 with the porous material 122. The tab 158 may be cushioned by the porous material 122 when the tab 158 is formed on a side of the first part 144 adjacent to the first panel 108 and configuring the porous material 122 to be positioned between the tab 158 and the second panel 110.

In an embodiment, the tab 158 may be formed from the same material as the rest of the port 130. In such an embodiment, the port 130 may exhibit integral construction (e.g., single-piece construction) which may make manufacturing of the port 130 more efficient. In an embodiment, the tab 158 may be distinct (e.g., formed from a different material) from the rest of the port 130. In such an embodiment, manufacturing of the port 130 may be more difficult since manufacturing of the port 130 requires forming to pieces (instead of one) and attaching the two pieces together.

Referring back to FIGS. 1A-1E, the fluid outlet 118 and the port 130 may be located at or near the distal region 162 of the sheath 102 which is expected to be the gravimetrically low point of the chamber 112 when worn by a user. Locating the fluid outlet 118 and the port 130 at or near the distal region 162 of the sheath 102 enables the conduit 142 to receive more of the bodily fluids than if the fluid outlet 118 and the port 130 was located elsewhere and reduce the likelihood of pooling (e.g., pooling of the bodily fluids may cause microbe growth and foul odors). For instance, the bodily fluids in porous material 122 due to capillary forces. However, the bodily fluids may exhibit a preference to flow in the direction of gravity, especially when at least a portion of the porous material 122 is saturated with the bodily fluids. Accordingly, the fluid outlet 118 and the port 130 may be located in the fluid collection assembly 100 in a position expected to be the gravimetrically low point in the fluid collection assembly 100 when worn by a user.

As previously discussed, the sheath 102 includes at least one porous material 122 disposed in the chamber 112. The porous material 122 may direct the bodily fluids to one or more selected regions of the chamber 112, such as away from the penis and towards the fluid outlet 118. As such, the porous material 122 may facilitate the removal of the bodily fluids from the chamber 112 and form a padding layer that prevents the penis from resting against a damp material which may cause degradation of the skin of the penis and/or make the fluid collection assembly 100 more uncomfortable to wear. The porous material 122 may also blunt a stream of urine from the penis.

In an embodiment, the porous material 122 includes a wicking material configured to wick any bodily fluids away from the opening 114 thereby preventing the bodily fluids from escaping the chamber 112. Such "wicking" may not include absorption of fluid into the wicking material. Put another way, substantially no absorption of fluid into the material may take place after the material is exposed to the fluid and removed from the fluid for a time. While no absorption is desired, the term "substantially no absorption" may allow for nominal amounts of absorption of fluid into the wicking material (e.g., absorbency), such as less than about 30 wt % of the dry weight of the wicking material, less than 20 wt %, less than 15 wt %, less than 10 wt %, less than about 7 wt %, less than about 5 wt %, less than about 3 wt %, less than about 2 wt %, less than about 1 wt %, or less than about 0.5 wt % of the dry weight of the wicking material. The wicking material may also wick the fluid generally towards an interior of the chamber 112, as discussed in more detail below. In an embodiment, the porous material 122 is configured to adsorb or absorb the bodily fluids. Similar, to the wicking material, such adsorbing or absorbing material may move bodily fluids away from the opening 114 thereby preventing the bodily fluids from escaping the chamber 112.

The porous material 122 may be formed from any suitable porous material. For example, the porous material 122 may be formed from nylon (e.g., spun nylon fibers), polyester, polyurethane, polyethylene, polypropylene, other porous polymers, hydrophobic foam, an open cell foam, wool, silk, linen, cotton (e.g., cotton gauze), felt, other fabrics, a coated porous material (e.g., a water repellent coated porous material), any other suitable porous materials, or combinations thereof.

Figure 1G:
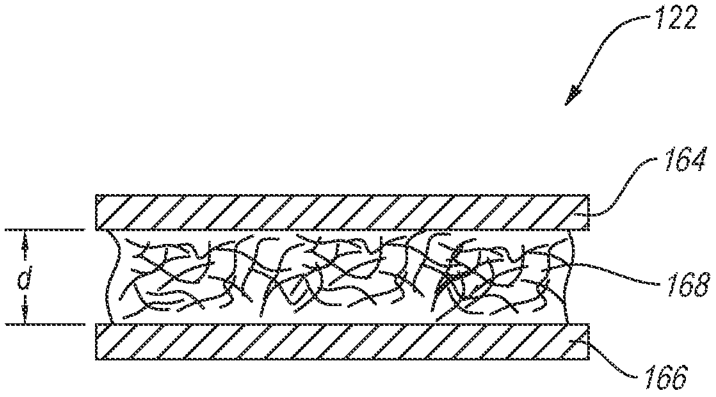
FIG. 1G is a cross-sectional schematic of a porous material, according to an embodiment.

FIG. 1G is a cross-sectional schematic of a porous material 122, according to an embodiment. The porous material 122 includes a first layer 164 and a second layer 166. The first and second layers 164, 166 may be a woven material. The porous material 122 also includes a plurality of fibers 168 forming a layer between the first layer 164 and the second layer 166. Each of the first layer 164, the second layer 166, and the plurality of fibers 168 define a plurality of pores, thereby allowing transport of the bodily fluids and air circulation through the porous material 122. The pores defined by the plurality of fibers 168 may be at least one of larger or more numerous, thereby decreasing the likelihood that dried bodily fluids clog the porous material 122. The presence of the plurality of fibers 168 also cause the porous material 122 feel soft against the penis and provides a cushioning effect to the penis. The plurality of fibers 168 may also prevent the vacuum force from collapsing the porous material.

In an embodiment, the plurality of fibers may cause the first layer 164 to be spaced from the second layer 166 by a distance d. The distance d may be selected based on the number of fibers that form the plurality of fibers 168 and the density at which the plurality of fibers 168 are packed together. For example, the distance d may be selected to be about 0.25 mm or more, about 0.5 mm or more, about 0.75 mm or more, about 1 mm or more, about 1.5 mm or more, about 2 mm or more, about 3 mm or more, about 4 mm or more, about 5 mm or more, about 6 mm or more, about 8 mm or more, about 10 mm or more, about 12.5 mm or more, about 15 mm or more, or in ranges of about 0.25 mm to about 0.75 mm, about 0.5 mm to about 1 mm, about 0.75 mm to about 1.5 mm, about 1 mm to about 2 mm, about 1.5 mm to about 3 mm, about 2 mm to about 4 mm, about 3 mm to about 5 mm, about 4 mm to about 6 mm, about 5 mm to about 8 mm, about 6 mm to about 10 mm, about 8 mm to about 12.5 mm, or about 10 mm to about 15 mm. The thickness of the distance d may be selected to adjust the absorbency of the porous material 122. For example, increasing the thickness may increase the volume of the plurality of fibers 168 and/or the porosity defined by the plurality of fibers 168 which increases the amount of bodily fluids that may be received by and at least partially stored in the porous material 122.

The first layer 164, the second layer 166, and the plurality of fibers 168 may be formed from any suitable material, such as a hydrophobic material, a hydrophilic material, polyester, cotton, or any other porous material disclosed herein. In an embodiment, one or more of the first layer 164, the second layer 166, or the plurality of fibers 168 are formed from a hydrophobic material that inhibits the porous material 122 from storing the bodily fluids therein which may facilitate removal of the bodily fluids from the chamber 112. In an embodiment, one or more of the first layer 164, and second layer 166, or the plurality of fibers 168 are formed from a hydrophilic material which allows the porous material 122 to temporarily store the bodily fluids therein thereby limiting the quantity of bodily fluids that pool around the skin of the individual. In an embodiment, two or more of the first layer 164, the second layer 166, or the plurality of fibers 168 are formed from different materials. In such an embodiment, the first layer 164 may define the penis receiving area 131 or is otherwise closer to the penis receiving area 131 than the second layer 166. The first layer 164 may be formed from a hydrophobic material while the plurality of fibers 168 are formed from a hydrophilic material. Such a configuration may cause the bodily fluids to be pulled through the first layer 164 and temporarily stored in the plurality of fibers 168. However, the first layer 164 may remain substantially dry due to the hydrophobicity thereof which allows the porous material 122 to feel dry to the penis. In an embodiment, at least one of the first layer 164 or the second layer 166 is formed from a fabric (e.g., fabric gauze) and the plurality of fibers 168 is formed from nylon fibers (e.g., spun nylon fibers).

In an embodiment, not shown, the porous material 122 may be formed from two layers instead of the three layers illustrated in FIG. 1G. For example, the porous material 122 may be formed from a fluid permeable membrane and a fluid permeable support. The fluid permeable support may define or otherwise be closer to the penis receiving area 131 than the fluid permeable support. The fluid permeable membrane may be composed and/or structured to wick bodily fluids away from the penis receiving area 131, thereby minimizing the quantity of bodily fluids that are present in the penis receiving area 131 or otherwise present against the skin of the individual. It is also noted that the fluid permeable membrane may also be configured to adsorb or absorb the bodily fluids to minimize the quantity of bodily fluids that are present in the penis receiving area 131 or otherwise present against the skin of the individual. The fluid permeable membrane may be formed from any of the porous materials disclosed herein. For example, the fluid permeable membrane may be formed from fabric, such as a gauze (e.g., silk, linen, or cotton gauze), another soft fabric, another smooth fabric, a woven or nonwoven material (e.g., spun nylon fiber), or any other suitable porous material. Forming the fluid permeable membrane from gauze, soft fabric, and/or smooth fabric (or any of the other porous materials 122 disclosed herein that may contact the penis) may reduce chaffing caused by the fluid collection assembly 100.

The fluid permeable support is configured to support the fluid permeable membrane since the fluid permeable membrane may be formed from a relatively foldable, flimsy, or otherwise easily deformable material. For example, the fluid permeable support may be positioned such that the fluid permeable membrane is disposed between the fluid permeable support and the fluid impermeable barrier 106. As such, the fluid permeable support may support and maintain the position of the fluid permeable membrane. The fluid permeable support may include any of the fluid permeable membrane materials disclosed herein above. For example, the fluid permeable membrane material(s) may be utilized in a more dense or rigid form than in the fluid permeable membrane when used as the fluid permeable support. The fluid permeable support may be formed from any fluid permeable material that is less deformable than the fluid permeable membrane. For example, the fluid permeable support may include a porous polymer (e.g., nylon, polyester, polyurethane, polyethylene, polypropylene, etc.) structure or an open cell foam. In some examples, the fluid permeable support may be formed from a natural material, such as cotton, wool, silk, or combinations thereof. In such examples, the material may have a coating to prevent or limit absorption of fluid into the material, such as a water repellent coating. In some examples, the fluid permeable support may be formed from fabric, felt, gauze, or combinations thereof.

In an embodiment, the porous material 122 may include a single layer (e.g., one of the first layer 164, the second layer 166, the layer formed from the plurality of fibers 168, the fluid permeable membrane, the fluid permeable support, or another porous layer). In an embodiment, the porous material 122 may be formed from four or more layers.

Examples of other materials that may form the porous material 122 are disclosed in U.S. Provisional Patent Application No. 63/134,754 filed on Jan. 7, 2021; U.S. Provisional Patent Application No. 63/241,575 filed on Sep. 8, 2021; and U.S. Provisional Patent Application No. 63/247,491 filed on Sep. 23, 2021; the disclosures of each of which are incorporated herein, in its entirety, by this reference.

In an embodiment, the porous material 122 may be a sheet (e.g., a multi-layer sheet). The porous material 122 is a sheet when the porous material 122 at least one of is generally planar when lying on a flat surface, does not define a cavity (e.g., is not tubular), or exhibits a length and width that is greater than a thickness thereof. Forming the porous material 122 as a sheet may facilitate the manufacturing of the fluid collection assembly 100. For example, forming the porous material 122 as a sheet allows the first panel 108, the second panel 110, and the porous material 122 to each be sheets. During the manufacturing of the fluid collection assembly 100, the first panel 108, the second panel 110, and the porous material 122 may be stacked and then attached to each other in the same manufacturing step. For instance, the porous material 122 may exhibit a shape that is the same size or, more preferably, slightly smaller than the size of the first panel 108 and the second panel 110. As such, attaching the first panel 108 and the second panel 110 together along the outer edges (e.g., top edges 136 and lateral edges 138) thereof may also attach the porous material 122 to the first panel 108 and the second panel 110. The porous material 122 may be slightly smaller than the first panel 108 and the second panel 110 such that the first panel 108 and/or the second panel 110 extend around the porous material 122 such that the porous material 122 does not form a passageway through the fluid impermeable barrier 106 through which the bodily fluids may leak. Also, attaching the porous material 122 to the first panel 108 and/or the second panel 110 may prevent the porous material 122 from significantly moving in the chamber 112, such as preventing the porous material 122 from bunching together near the fluid outlet 118. In an example, the porous material 122 may be attached to the first panel 108 or the second panel 110 (e.g., via an adhesive) before or after attaching the first panel 108 to the second panel 110. In an example, the porous material 122 may merely be disposed in the chamber 112 without attaching the porous material 122 to at least one of the first panel 108 or the second panel 110. In an embodiment, as will be discussed in more detail below, the porous material 122 may exhibit shapes other than a sheet, such as a hollow generally cylindrical shape.

The porous material 122 may exhibit a shape that generally corresponds to the shape of the fluid impermeable barrier 106 such that the porous material 122 partially or substantially completely occupies all of the chamber 112. For example, as illustrated, the porous material 122 may exhibit a generally bullet shape. The porous material 122 may exhibit a generally bullet shape when the porous material 122 includes a proximal portion 170 corresponding to the proximal region 160 and a distal portion 172 extending from the proximal portion 170 that corresponds to the distal region 162. The proximal portion 170 may exhibit a substantially constant first width and the distal portion 172 may exhibit a second width that is less than the first width. The second width may be constant or vary (e.g., vary at a constant or variable rate). The porous material 122 may exhibit a shape other than the generally bullet shape, such as a generally rectangular shape, generally semi-oval shape, or any other suitable shape.

Generally, the sheath 102 is substantially flat when the penis is not in the penis receiving area 131 and the sheath 102 is resting on a flat surface. The sheath 102 is substantially flat because the fluid impermeable barrier 106 is formed from the first panel 108 and the second panel 110 instead of a generally tubular fluid impermeable barrier. Further, as previously discussed, the porous material 122 may be a sheet, which also causes the sheath 102 to be substantially flat. It is noted that the sheath 102 is described as being substantially flat because at least one of the porous material 122 may cause a slight bulge to form in the sheath 102 depending on the thickness of the porous material 122, the port 130 may cause a bulge thereabout, or the base 104 may pull on portions of the sheath 102 thereabout. It is also noted that the sheath 102 may also be compliant and, as such, the sheath 102 may not be substantially flat during use since, during use, the sheath 102 may rest on a non-flat surface (e.g., may rest on the testicles, the perineum, and/or between the thighs) and the sheath 102 may conform to the surface of these shapes.

The ability of the sheath 102 to be substantially flat when the penis is not in the penis receiving area 131 and the sheath 102 is resting on a flat surface allows the fluid collection assembly 100 to be used with a buried and a non-buried penis. For example, when the fluid collection assembly 100 is being used with a buried penis, the penis does not extend into the penis receiving area 131 which causes the sheath 102 to lie relatively flat across the aperature 124. When the sheath 102 lies relatively flat across the aperture 124, the porous material 122 extends across the aperature and is in close proximity to the buried penis. As such, the porous material 122 prevents or inhibits pooling of bodily fluids discharged from the buried penis against the skin of the individual since the porous material 122 will receive and remove at least a significant portion of the bodily fluids that would otherwise pool against the skin of the individual. Thus, the skin of the individual remains dry thereby improving comfort of using the fluid collection assembly 100 and preventing skin degradation. However, unlike other conventional fluid collection assemblies that are configured to be used with buried penises, the fluid collection assembly 100 may still be used with a non-buried penis since the non-buried penis can still be received into the penis receiving area 131, even when the penis is fully erect. Additionally, the ability of the sheath 102 to be substantially flat allows the fluid collection assembly 100 to be used more discretely than if the sheath 102 was not substantially flat thereby avoiding possibly embarrassing scenarios.

When the sheath 102 is substantially flat, the porous material 122 may occupy substantially all of the chamber 112 and the penis receiving area 131 is collapsed (shown as being non-collapsed in FIGS. 1C and 1D for illustrative purposes). In other words, the sheath 102 may not define a region that is constantly unoccupied by the porous material 122. When the porous material 122 occupies substantially all of the chamber 112, the bodily fluids discharged into the chamber 112 are unlikely to pool for significant periods of time since pooling of the bodily fluids may cause sanitation issues, cause an odor, and/or may cause the skin of the individual to remain in contact with the bodily fluids which may cause discomfort and skin degradation.

As previously discussed, the first panel 108, the second panel 110, and the porous material 122 may be selected to be relatively flexible. The first panel 108, the second panel 110, and the porous material 122 are relatively flexible when the first panel 108, the second panel 110, and the porous material 122, respectively, are unable to maintain their shape when unsupported. The flexibility of the first panel 108, the second panel 110, and the porous material 122 may allow the sheath 102 to be substantially flat, as discussed above. The flexibility of the first panel 108, the second panel 110, and the porous material 122 may also allow the sheath 102 to conform to the shape of the penis even when the size and shape of the penis changes (e.g., becomes erect) and to minimize any unoccupied spaces in the chamber 112 in which bodily fluids may pool.

As previously discussed, the fluid collection assembly 100 includes a base 104 that is configured to be coupled to the skin that surrounds the penis (e.g., mons pubis, thighs, testicles, and/or perineum) and have the penis disposed therethrough. For example, the base 104 may define an aperture 124 configured to have the penis positioned therethrough. The base 104 may be flexible, thereby allowing the base 104 to conform to any shape of the skin surface and mitigate the base 104 pulling the on skin surface.

Figure 1H:
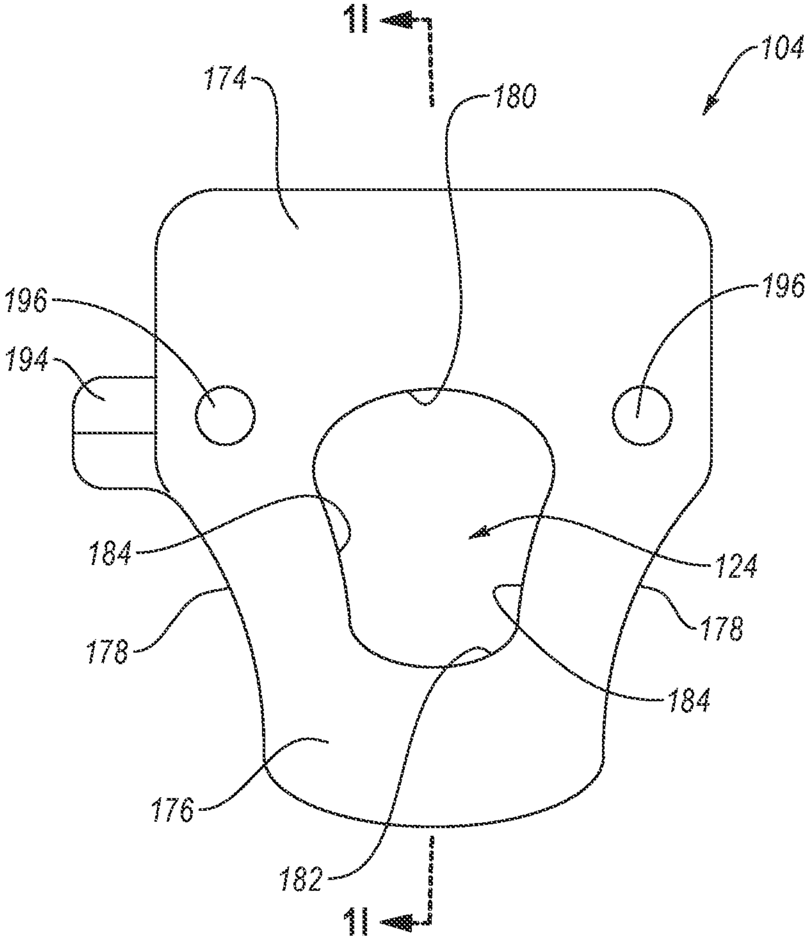
FIG. 1H is a top plan view of the base, according to an embodiment.

FIG. 1H is a top plan view of the base 104, according to an embodiment. The base 104 is configured to be attached to the region about the penis (e.g., mons pubis) while not being attached to the thighs since attaching the base 104 to the thighs may cause the base 104 to uncomfortably pull when the individual moves. In an example, the base 104 may include a primary attachment portion 174 and a secondary attachment portion 176. The primary attachment portion 174 is configured to be attached to the mons pubis and the secondary attachment portion 176 is configured to be attached to the region about the penis except for the mons pubis(e.g., an upper portion of the testicles). The primary attachment portion 174 may exhibit a generally rectangular or trapezoidal shape. The primary attachment portion 174 may extend further from the aperture 124 than the secondary attachment portion 176 since the mons pubis is less sensitive and larger than the other regions about the penis. The secondary attachment portion 176 may include one or more concave lateral edges 178. The concave lateral edges 178 may help prevent the secondary attachment portion 176 from being attached to the thighs of the individual. It is noted that any corners of the base 104 may be rounded to prevent or at least inhibit the base 104 uncomfortably pressing into the individual.

The base 104 may exhibit shapes other than the shape illustrated in FIG. 1H. For example, the base 104 may exhibit a generally partially triangular shape having three apexes and edges extending between each of the apexes. The apexes may be rounded to prevent the base 104 from digging into and hurting the individual. The aperture 124 may be located off-center and closer to one of the apexes than the other apexes. Other examples of shapes that the base 104 may form are disclosed in PCT Application No. PCT/US2021/015787 filed on Jan. 29, 2021, the disclosure of which is incorporated herein, in its entirety, by this reference.

In an embodiment, not shown, the aperture 124 may exhibit a generally circular shape. In an embodiment, as illustrated, the aperture 124 may exhibit a non-circular shape. The non-circular shape of the aperture 124 may be selected to at least one of correspond to the cross-sectional shape of a base of a penis and/or better conform to the region about the penis, either of which may limit leakage and pooling of the bodily fluids. For example, as illustrated, the aperture 124 may exhibit a generally bell-like shape. The generally bell-like shape includes a concave (relative to an interior of the aperture 124) top edge 180 and a concave bottom edge 182 opposite the concave top edge 180. The generally bell-like shape also includes two convex lateral edges 184 extending between the top and bottom edges 180, 182. Any corners between the top, bottom, and lateral edges 180, 182, 184 may be rounded. The two convex lateral edges 184 cause the width of the aperture 124 to vary. For example, the two convex lateral edges 184 cause a width of the aperture 124 near the top edge 180 to be smaller than a width of the aperture 124 near the bottom edge 182. The generally bell-like shape of the aperture 124 may allow the aperture 124 to correspond to the shape of the base of the penis which prevents bodily fluids leaking from the chamber 112 and inhibits pooling of the bodily fluids. The aperture 124 may exhibit other non-circular shapes, such as generally triangular shape, a generally trapezoidal shape, a generally hippopede shape, or any other suitable non-circular shape.

Figure 1I:
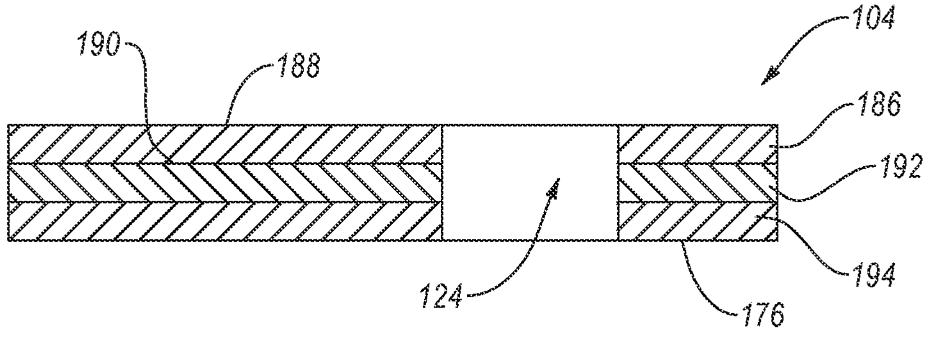
FIG. 1I is a cross-sectional schematic of the base, according to an embodiment.

FIG. 1I is a cross-sectional schematic of the base 104, according to an embodiment. The base 104 includes a substrate 186 having a top surface 188 and a bottom surface 190. The top surface 188 is closer to the sheath 102 than the bottom surface 190 while the bottom surface 190 is closer to the skin of the individual than the top surface 188. The base 104 may also include an adhesive layer 192 disposed on at least a portion of the bottom surface 190. The adhesive layer 192 is configured to attach the base 104 to the skin around the penis. The base 104 may also include a release liner 194 is configured to be easily removed from the adhesive layer 192 and is configured to prevent the adhesive layer 192 inadvertently becoming attached to an object.

The substrate 186 may be formed from a fluid impermeable material to prevent bodily fluids from leaking from the chamber 112 through the base 104. For example, the substrate 186 may be formed from any of the fluid impermeable materials disclosed herein. In a particular example, the substrate 186 may be formed from a hydrophobic porous material, such as a hydrophobic woven or nonwoven material. The hydrophobicity of the hydrophobic porous material, in conjunction with the small pores thereof, may prevent bodily fluids from flowing therethrough. It is noted that the hydrophobic porous material may allow air to flow therethrough which may make wearing the fluid collection assembly 100 more comfortable.

In an embodiment, the substrate 186 exhibits a thickness that is about 2 mm or less, about 1.5 mm or less, about 1 mm or less, about 0.75 mm or less, about 0.5 mm or less, about 0.3 mm or less, about 0.2 mm or less, about 0.1 mm or less, about 0.05 mm or less, or in ranges of about 0.05 mm to about 0.2 mm, about 0.1 mm to about 0.3 mm, about 0.2 mm to about 0.5 mm, about 0.3 mm to about 0.75 mm, about 0.5 mm to about 1 mm, about 0.75 mm to about 1.5 mm, or about 1 to about 2 mm. Forming the substrate 186 to exhibit any of the above thicknesses may cause the substrate 186 to be sufficiently flexible to conform to the shape and contours of the skin surrounding the penis. For instance, the shape and contours of the skin surrounding the penis may vary from individual to individual and configuring the substrate 186 to be a thin film may allow the base 104 to conform to the shape and contour of the skin surrounding the penis while preventing the formation of any gaps between the base 104 and the skin through which bodily fluids may leak. Further, the thin film substrate 186 is able to be attached to the skin of the individual without or substantially without pulling the skin of the individual which makes the fluid collection assembly 100 more comfortable to use for prolonged periods of time. It is noted that the amount of the fluid collection assembly 100 pulls on the skin decreases with decreasing thickness of the substrate such that, for example, a substrate exhibiting a thickness of about 2 mm pulls more on the skin than a substantially similar substrate exhibiting a thickness of about 0.5 mm.

The adhesive layer 192 may be formed from any adhesive that may safely attach the substrate 186 to the skin surrounding the penis. In an example, the adhesive layer 192 may be formed from a silicone-based adhesive, such as a silicone-gel adhesive. Silicone-based adhesives, such as Medical Silicone Tape 2475P available from 3M, has been found to secure the fluid collection assembly 100 to the skin surrounding the penis for at least 24 hours, even immediately after cleaning the skin surface with a wipe. In an example, the adhesive layer 192 may be formed from an acrylic gel adhesive or a hydrogel.

In an embodiment, the base 104 is at least partially transparent (e.g., the substrate 186 and the adhesive layer 192 are formed from at least partially transparent materials). In such an embodiment, a person (e.g., medical practitioner) may be able to examiner the skin surrounding the penis, such as to determine the health of the skin. Further, the person may be able to detect any gaps between the base 104 and the skin of the individual through which bodily fluids may leak. A person may be able to eliminate the gaps or replace the fluid collection assembly 100 after detecting the gaps to prevent leaks and prevent degradation of the skin caused by the skin being in contact with the bodily fluids.

As previously discussed, the base 104 is configured to be attached (e.g., permanently attached) to the sheath 102. The base 104 is configured to be attached to the sheath 102 when, for example, the fluid collection assembly 100 is provided with the base 104 attached to the sheath 102 or the base 104 is provided without being attached to the sheath 102 but is configured to be attached to the sheath 102 at some point in the future. The base 104 may be attached to the sheath 102 using any suitable technique. For example, the base 104 may be attached to the sheath 102 using an adhesive, sewing, heat sealing, impulse heating, RF welding, or US welding.

In an embodiment, the base 104 is permanently attached to the sheath 102. The base 104 is permanently attached to the sheath 102 when the base 104 cannot be detached from the sheath 102 without damaging at least one of the sheath 102 or the base 104, using a blade to separate the sheath 102 from the base 104, using chemicals to dissolve the adhesive that attaches the sheath 102 to the base 104, and/or using heat to melt or soften the adhesive or attachment (e.g., ultrasonic weld) that attached the sheath 102 to the base 104. In an embodiment, the base 104 is attached to the sheath 102 using an non-permanent attachment.

In an embodiment, all of the base 104 is attached to the sheath 102 which may strengthen the attachment between the sheath 102 and the base 104. In an embodiment, as illustrated, only the inner portions of the base 104 defining or adjacent to the aperture 124 are attached to the sheath 102. Attaching only the inner portions of the base 104 to the sheath 102 may be sufficient to maintain the base 104 attached to the sheath 102 during use. Only attaching the inner portions of the base 104 to the sheath 102 may allow the outer portions of the base 104 (e.g., portions of the base 104 other than the inner portions) to be easily handled by a user of the fluid collection assembly 100 which, in turn, makes it easier to attach the base 104 to the individual.

In an embodiment, the base 104 may be attached to the second panel 110 before the second panel 110 is attached to the first panel 108 which facilitates attaching the base 104 to sheath 102, for example, using US welding, RF welding, and impulse heating. Attaching the base 104 to the second panel 110 before securing the porous material 122 in the chamber 112 may cause difficulties securing the porous material 122 in the chamber 112 since the base 104 may be in the way. In an example, as illustrated, the base 104 and the porous material 122 may define one or more base gaps 196 and one or more porous material gaps 198, respectively. The base gaps 196 and the porous material gaps 198 may be generally aligned with each other such that the base gaps 196 and the porous material gaps 198 are adjacent to each other. The base gaps 196 and the porous material gaps 198 allows opposing portions of the fluid impermeable barrier 106 that are generally aligned with the base gaps 196 and the porous material gaps 198 to be attached together (e.g., using US welding, RF welding, impulse heating, direct heating, heat staking, etc.). Attaching the opposing portions of the fluid impermeable barrier 106 together may secure the porous material 122 in the chamber 112. In a particular example, as illustrated, the base gaps 196 and the porous material gaps 198 may be formed in portions of the base 104 and the porous material 122 that are adjacent to or above (e.g., further spaced from the fluid outlet 118) portions of the aperture 124 that are furthest spaced from the fluid outlet 118. Such positioning of the base gaps 196 and the porous material gaps 198 may keep the porous material 122 extending across the aperture 124.

Referring back to FIGS. 1A-1D, as previously discussed, the fluid collection assembly 100 includes a conduit 142. The conduit 142 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some examples, the conduit 142 may include silicon or latex. In some examples, the conduit 142 may include one or more portions that are resilient, such as to by having one or more of a diameter or wall thickness that allows the conduit to be flexible.

As described in more detail below, the conduit 142 is configured to be coupled to, and at least partially extend between, one or more of the fluid storage container (not shown) and the vacuum source (not shown). In an example, the conduit 142 is configured to be directly connected to the vacuum source (not shown). In such an example, the conduit 142 may extend from the fluid impermeable barrier 106 by at least one foot, at least two feet, at least three feet, or at least six feet. In another example, the conduit 142 is configured to be indirectly connected to at least one of the fluid storage container (not shown) and the vacuum source (not shown). In some examples, the conduit is secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet and an outlet of the conduit 142 are configured to fluidly couple (e.g., directly or indirectly) the vacuum source (not shown) to the chamber 112. As the vacuum source (FIG. 4) applies a vacuum/vacuum in the conduit 142, the bodily fluids in the chamber 112 may be drawn into the inlet 148 and out of the fluid collection assembly 100 via the conduit 142. In some examples, the conduit 142 may be frosted or opaque (e.g., black) to obscure visibility of the bodily fluids therein.

In some examples, the vacuum source may be remotely located from the fluid collection device. In such examples, the conduit 142 may be fluidly connected to the fluid storage container, which may be disposed between the vacuum source and the fluid collection assembly 100.

During operation, a male using the fluid collection assembly 100 may discharge bodily fluids (e.g., urine) into the chamber 112. The bodily fluids may pool or otherwise be collected in the chamber 112 (e.g., received into the porous material 122). At least some of the bodily fluids may be pulled through the interior of the conduit 142 via the inlet. The bodily fluids may be drawn out of the fluid collection assembly 100 via the vacuum/vacuum provided by the vacuum source. During operation, the vents 134 may substantially maintain the pressure in the chamber 112 at atmospheric pressure even though bodily fluids are introduced into and subsequently removed from the chamber 112.

Figure 2:
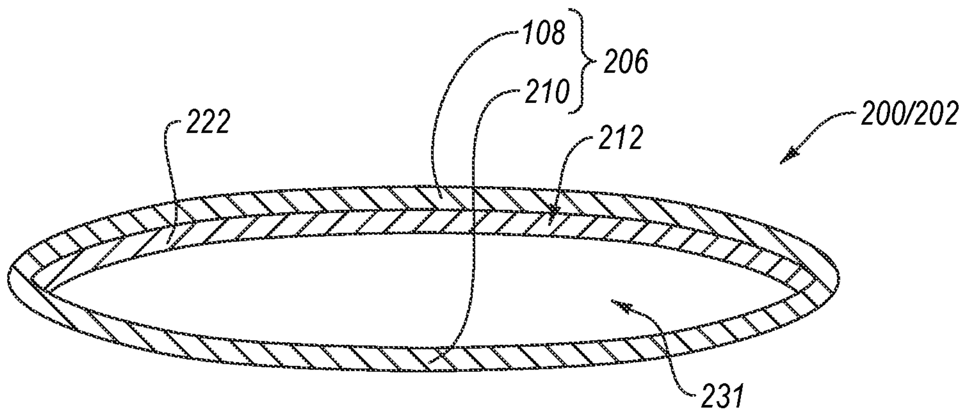
FIG. 2 is a cross-sectional schematic view of a fluid collection assembly that includes a first panel and a second panel integrally formed together, according to an embodiment.

As previously discussed, the fluid collection assembly 100 is formed from the first panel 108 and the second panel 110 that are distinct sheets which may allow the first panel to be at least partially opaque while the second panel is at least partially transparent. However, forming the first and second panels 108, 110 from distinct sheets may form edges that may cause patient discomfort and requires a significant amount of manufacturing (e.g., welding or other attachment technique) to attach the first panel 108 to the second panel 110. As such, in some embodiments, the fluid collection assemblies disclosed herein may be formed from first and second panels that are integrally formed together (e.g., exhibit single piece construction) which may eliminate at least some of the edges and simplify manufacturing of such fluid collection assemblies. For example, FIG. 2 is a cross-sectional schematic view of a fluid collection assembly 200 that includes a first panel 208 and a second panel 210 integrally formed together, according to an embodiment. Except as otherwise disclosed herein, the fluid collection assembly 200 may be the same or substantially similar to any of the fluid collection assemblies disclosed herein. For example, the fluid collection assembly 200 includes a sheath 202 and a base (not shown). The sheath 202 at least defines a chamber 212, an opening (not shown), and a fluid outlet (not shown). The fluid collection assembly 200 also includes at least one porous material 222 disposed in the chamber 212.

As previously discussed, the first panel 208 and the second panel 210 are integrally formed together. As such, the first panel 208 and the second panel 210 are different regions of fluid impermeable barrier 206 instead of different sheets that are attached together. The first panel 208 is the region of the fluid impermeable barrier 206 adjacent to the porous material 222 while the second panel 210 is the region of the fluid impermeable barrier 206 adjacent to the penis receiving area 231 (shown in a non-collapsed state for illustrative purposes).

In an embodiment, as illustrated, the first and second panels 208, 210 are formed from a thin walled tube, such as thin walled tube formed using a blown film extrusion process. Forming the first and second panels 208, 210 from the thin walled tube precludes the need to attach the longitudinal edges of the first and second panels 208, 210 together. However, the portions of the first and second panels 208, 210 that form the proximal end region and the distal end region thereof may need to be attached together using any of the techniques disclosed herein. As such, forming the first and second panels 208, 210 from a thin walled tube makes manufacturing of the fluid collection assembly 200 more efficient since fewer portions of the first and second panels 208, 210 need to be attached together. Further, forming the first and second panels 208, 210 from the thin walled tube decreases the number of edges that may press into the individual compared to forming the first and second panels 208, 210 from two distinct sheets.

In an embodiment, the first and second panels 208, 210 are formed from a single sheet that is folded. Forming the first and second panels 208, 210 from the single folded sheet precludes the need to attach one of the longitudinal edges of the first and second panels 208, 210 together. However, the portions of the first and second panels 208, 210 that form the proximal end region, the distal end region, and the portion opposite the fold may need to be attached together using any of the attachment techniques disclosed herein. Thus, forming the first and second panels 208, 210 from a single folded sheet makes manufacturing of the fluid collection assembly 200 more efficient and decreases the number of edges that are formed compared to forming the first and second panels 208, 210 from two distinct sheets. It is noted that, in either embodiment, the first panel 208 and the second panel 210 may still lie substantially flat when the penis is not in the chamber 212.

In an embodiment, the second panel 210 may have an opening formed therein. For example, the second panel 210 may have a cutout formed therein that is spaced from or extends inwardly from an outer edge of the second panel 210 (e.g., an outer edge of the thin walled tube or the single folded sheet).

Figure 3A:
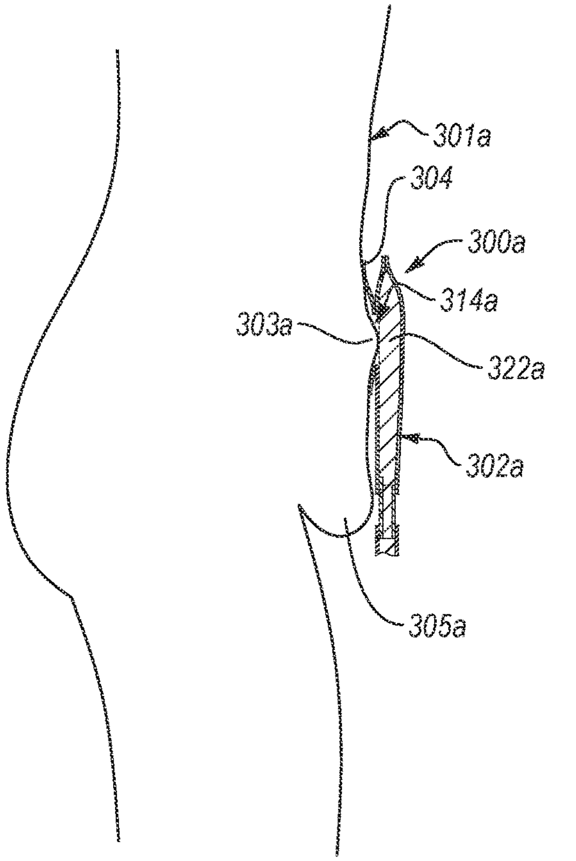
FIGS. 3A and 3B are cross-sectional schematics illustrating how substantially similar fluid collection assemblies may be used with a buried and non-buried penis, according to an embodiment.
Figure 3B:
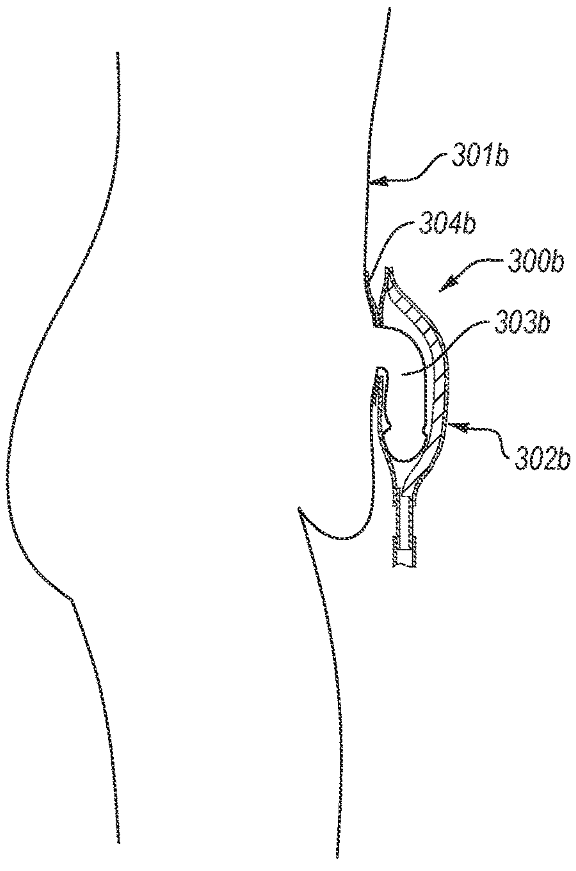

As previously discussed, the fluid collection assemblies disclosed herein may be used with a buried penis and a non-buried penis. FIGS. 3A and 3B are cross-sectional schematics illustrating how substantially similar fluid collection assemblies may be used with a buried and non-buried penis, according to an embodiment. Referring to FIG. 3A, a first individual **301*a* has a buried penis 303*a* (shown schematically as a slight bump). The fluid collection assembly 300*a* is attached to the first individual 301*a*. The fluid collection assembly 300*a* is illustrated as being substantially the same as fluid collection assembly 100 shown in FIGS. 1A-1I. However, it is noted that the fluid collection assembly 300*a* may include any of the fluid collection assemblies disclosed herein. The fluid collection assembly 300*a* is attached to the first individual 301*a* such that the aperture of the base 304*a* and the opening of the sheath 302*a* is adjacent to the buried penis 303*a*. Since the fluid collection assembly 300*a* lies substantially flat, the porous material 322*a* is generally adjacent to the opening and may only be spaced from the buried penis 303*a* by the thickness of the base 304*a* which prevents almost no space for the bodily fluids to pool before being received by the porous material 322*a*. Is noted that the porous material 322*a* may be spaced from the buried penis 303*a* by a distance that is less than the thickness of the base 304*a* (e.g., the porous material 322*a* bulges into the aperture) or slightly greater than the thickness of the base 304*a* (e.g., the testicles 305*a* cause a bulge that pushes the porous material 322*a* away from the opening 314*a* or the porous material 322*a*** exhibits a non-sheet like shape).

Referring to FIG. 3B, a second individual 301*b* has a non-buried penis 303*b*. A fluid collection assembly 300*b* that is the same or substantially the same as the fluid collection assembly 300*a* is attached to the second individual 301*b*. The fluid collection assembly 300*b* is attached to the second individual 301*b* such that the penis 303*b* extends through the aperture of the base 304*b* and through the opening of the sheath 302*b*. Due to the flexibility of the fluid collection assembly 300*b*, the sheath 302*b* can receive the penis 303*b* therein.

Figure 4:
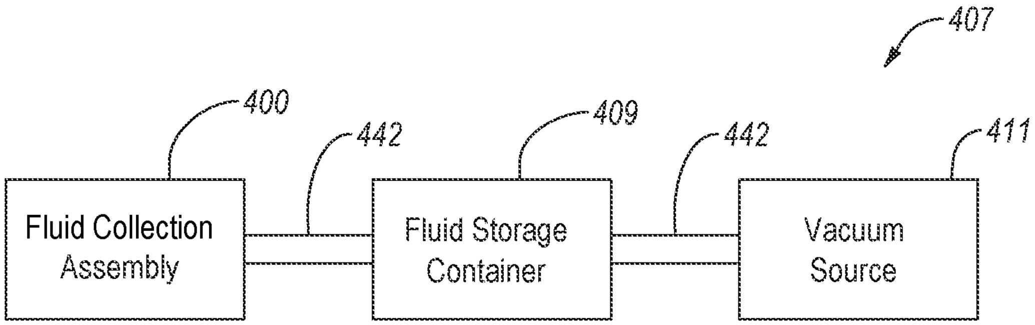
FIG. 4 is a block diagram of a system for fluid collection, according to an embodiment.

FIG. 4 is a block diagram of a system 407 for fluid collection, according to an embodiment. The system 407 includes a fluid collection assembly 400, a fluid storage container 409, and a vacuum source 411. The fluid collection assembly 400 may include any of the fluid collection assemblies disclosed herein. The fluid collection assembly 400, the fluid storage container 409, and the vacuum source 411 may be fluidly coupled to each other via one or more conduits 442. For example, fluid collection assembly 400 may be operably coupled to one or more of the fluid storage container 409 or the vacuum source 411 via the conduit 442. Bodily fluids (e.g., urine or other bodily fluids) collected in the fluid collection assembly 400 may be removed from the fluid collection assembly 400 via the conduit 442 which protrudes into the fluid collection assembly 400. Vacuum force may be introduced into the chamber of the fluid collection assembly 400 via the inlet of the conduit 442 responsive to vacuum (e.g., vacuum) force applied at the outlet of the conduit 442.

The vacuum force may be applied to the outlet of the conduit 442 by the vacuum source 411 either directly or indirectly. The vacuum force may be applied indirectly via the fluid storage container 409. For example, the outlet of the conduit 442 may be disposed within the fluid storage container 409 and an additional conduit 442 may extend from the fluid storage container 409 to the vacuum source 411. Accordingly, the vacuum source 411 may apply vacuum to the fluid collection assembly 400 via the fluid storage container 409. The vacuum force may be applied directly via the vacuum source 411. For example, the outlet of the conduit 442 may be disposed within the vacuum source 411. An additional conduit 442 may extend from the vacuum source 411 to a point outside of the fluid collection assembly 400, such as to the fluid storage container 409. In such examples, the vacuum source 411 may be disposed between the fluid collection assembly 400 and the fluid storage container 409.

The fluid storage container 409 is sized and shaped to retain a fluid therein. The fluid storage container 409 may include a bag (e.g., drainage bag), a bottle or cup (e.g., collection jar), or any other enclosed container for storing the bodily fluids. In some examples, the conduit 442 may 442 extend from the fluid collection assembly 400 and attach to the fluid storage container 409 at a first point therein. An additional conduit 442 may attach to the fluid storage container 409 at a second point thereon and may extend and attach to the vacuum source 411. Accordingly, a vacuum (e.g., vacuum) may be drawn through fluid collection assembly 400 via the fluid storage container 409. Fluid, such as urine, may be drained from the fluid collection assembly 400 using the vacuum source 411.

The vacuum source 411 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 411 may provide a vacuum or vacuum to remove fluid from the fluid collection assembly 400. In some examples, the vacuum source 411 may be powered by one or more of a power cord (e.g., connected to a power socket), one or more batteries, or even manual power (e.g., a hand operated vacuum pump). In some examples, the vacuum source 411 may be sized and shaped to fit outside of, on, or within the fluid collection assembly 400. For example, the vacuum source 411 may include one or more miniaturized pumps or one or more micro pumps. The vacuum sources 411 disclosed herein may include one or more of a switch, a button, a plug, a remote, or any other device suitable to activate the vacuum source 411.

Figure 5:
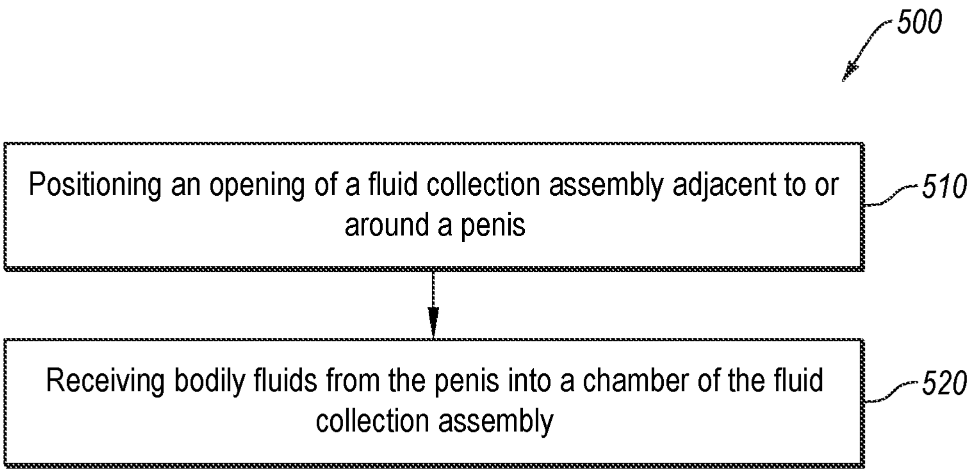
FIG. 5 is a flow diagram of a method to collect fluid, according to an embodiment.

FIG. 5 is a flow diagram of a method 500 to collect fluid, according to an embodiment. The method 500 of collecting fluid may utilize use any of the fluid collection assemblies and/or fluid collection systems disclosed herein. The method 500 may include act 510, which recites "positioning an opening of a fluid collection assembly adjacent to or around a penis." Act 510 may be followed by act 520, which recites "receiving bodily fluids from the penis into a chamber of the fluid collection assembly."

Acts 510 and 520 of the method 500 are for illustrative purposes. For example, the acts 510 and 520 of the method 500 may be performed in different orders, split into multiple acts, modified, supplemented, or combined. In an example, one or more of the acts 510 or 520 of the method 500 may be omitted from the method 500.

Act 510 recites "positioning an opening of a fluid collection assembly adjacent to or around a penis." The act 510 of positioning an opening of a fluid collection assembly may include utilizing any of the fluid collection assemblies or systems disclosed herein. In some examples, act 510 may include positioning the opening such that the porous material of the fluid collection assembly extends across the opening which allows the porous material to abut or be positioned proximate to a buried penis. In some examples, act 510 may include positioned a base of a fluid collection assembly over a buried penis such that the male urethra is positioned adjacent to an aperture of the base and an opening of the sheath. In such an example, act 510 may include positioning a sheath of the male fluid collection assembly around a non-buried penis, such that at least a portion of the penis is positioned through an opening of the sheath and in the chamber of the fluid collection assembly.

Act 520 recites, "receiving bodily fluids from the penis into a chamber of the fluid collection assembly." In some examples, receiving bodily fluids from the penis into a chamber of the fluid collection assembly includes receiving the bodily fluids through the opening of the fluid collection assembly. Receiving bodily fluids from the penis into a chamber of the fluid collection assembly may include at least one of wicking, absorbing, or adsorbing the bodily fluids away from the opening using the porous material. In some examples, receiving bodily fluids from the penis into a chamber of the fluid collection assembly may include receiving the bodily fluids into the chamber of the sheath of the fluid collection assembly. Receiving bodily fluids from the penis into a chamber of the fluid collection assembly may include flowing the bodily fluids towards a portion of the chamber that is fluidly coupled to an inlet of a conduit in fluid communication a vacuum source. For instance, receiving bodily fluids from the penis into a chamber of the fluid collection assembly may include flowing the bodily fluids to a gravimetrically low point of the chamber, etc., such as via gravity, wicking, or vacuum force.

The method 500 may include applying vacuum with a vacuum source effective to vacuum the bodily fluids from the chamber via a conduit disposed or otherwise in fluid communication with the chamber. The conduit may also be fluidly coupled to the vacuum source may include using any of the vacuum sources disclosed herein. Applying vacuum with a vacuum source may include activating the vacuum source (e.g., vacuum device) in fluid communication with the inlet of the conduit in the fluid collection assembly. In some examples, activating the vacuum source in fluid communication with the inlet of the conduit in the fluid collection assembly may include supplying power to the vacuum source by one or more of flipping an on/off switch, pressing a button, plugging the vacuum source into a power outlet, putting batteries into the vacuum source, etc. In some examples, the vacuum source may include a hand operated vacuum pump and applying vacuum with a vacuum source may include manually operating the hand operated vacuum pump effective to vacuum the bodily fluids from the chamber via the conduit disposed therein that is fluidly coupled to the vacuum source.

In some examples, applying vacuum with a vacuum source effective to vacuum the bodily fluids from the chamber via a conduit disposed therein and fluidly coupled to the vacuum source may be effective to remove at least some bodily fluids from the chamber of the fluid collection assembly. In some examples, applying vacuum with a vacuum source effective to vacuum the bodily fluids from the chamber via a conduit disposed therein and fluidly coupled to the vacuum source may be effective to transfer at least some of the bodily fluids from the chamber to a fluid storage container (e.g., a bottle or bag).

In some examples, the vacuum source (e.g., vacuum device) may be disposed on or within the fluid collection assembly and applying vacuum with the vacuum source may include activating the vacuum source. In some examples, the vacuum source may be spaced from the fluid collection assembly and applying vacuum with the vacuum source may include activating the vacuum source.

In some examples, applying vacuum with a vacuum source effective to vacuum the bodily fluids from the chamber via a conduit disposed therein and fluidly coupled to the vacuum source may include detecting moisture in the chamber (e.g., via one or more moisture sensors) and responsive thereto, activating the vacuum source to provide vacuum in the chamber. The control of the vacuum source responsive to the signals indicating that moisture or a level thereof is present in the chamber may be automatic, such as via a controller (e.g., computer programmed to perform the operation), or may merely provide an indication that a level of moisture is present that may necessitate removal of bodily fluids from the chamber of the fluid collection assembly. In the latter case, a user may receive the indication (e.g., from the controller) and activate the vacuum pump manually.

In an example, the method 500 may include collecting the bodily fluids that are removed from the fluid collection assembly, such as into a fluid storage container that is spaced from the fluid collection assembly and fluidly coupled to the conduit. The fluid storage container may include any of the fluid storage containers disclosed herein.

Figure 6:
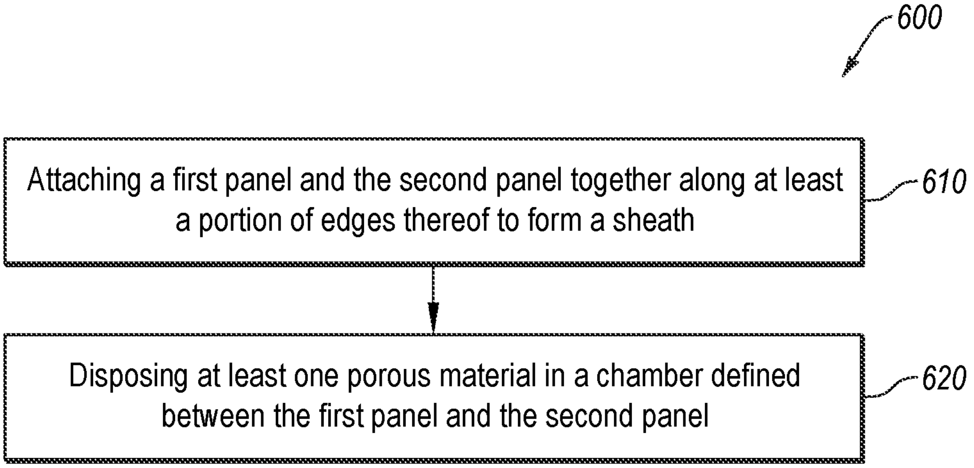
FIG. 6 is a flow diagram of a method to manufacture a fluid collection assembly, according to an embodiment.

FIG. 6 is a flow diagram of a method 600 to manufacture a fluid collection assembly, according to an embodiment. The method 600 may be used to manufacture at least some of the fluid collection assemblies and/or fluid collection systems disclosed herein. The method 600 may include act 610, which recites "attaching a first panel and the second panel together along at least a portion of edges thereof to form a sheath." Act 610 may be followed by act 620, which recites "disposing at least one porous material in a chamber defined between the first panel and the second panel."

Acts 610, 620 of the method 600 are for illustrative purposes. For example, the acts 610, 620 of the method 600 may be performed in different orders, split into multiple acts, modified, supplemented, or combined. In an example, one or more of the acts 610, 620 of the method 600 may be omitted from the method 600. Any of the acts 610 or 620 may include using any of the fluid collection devices or systems disclosed herein.

Act 610 recites "attaching at least a portion of a first panel and at least a portion of the second panel together along at least a portion of edges thereof to form a sheath." In an example, when the first and second panels are distinct sheets, act 610 may include positioning the first panel and the second panel adjacent to each other (e.g., on top of each other). Positioning the first panel and the second panel adjacent to each other forms a chamber between the first panel and the second panel. After positioning the first and second panels, the first and second panels may be attached to each other, such as attached to each other along at least a portion of the outer edges thereof. For instance, all of the outer edges of the first and second panels may be attached together except for portions of the outer edges thereof that define an opening configured to receive a penis (if the opening is not completely defined by one of the first or second panels) and a fluid outlet. In an example, the first and second panels are integrally formed together. In such an example, act 610 may include attaching edges of the first and second panels that are not already attached. When the first and second panels are formed by a thin walled tube, act 610 may include attaching the portions of the first and second panels that form the proximal and distal end regions thereof together. When the first and second panels are formed by a single folded sheet, act 610 may include attaching the portions of the first and second panels that form the proximal and distal end regions thereof together and attaching the portions of the first and second panels that are opposite the fold.

The first and second panels may be attached together using any suitable technique. In an embodiment, the first and second panels are attached together by sewing the first and second panels together. In an embodiment, the first and second panels are attached together using a non-sewing technique, such as via heat sealing, RF welding, or US welding. Using a non-sewing technique to attach the first and second panels together may increase the rate of manufacture of the fluid collection assembly formed during the method 600. For example, heat sealing, RF welding, or US welding may be performed significantly faster than sewing the first and second panels together. Further, heat sealing, RF welding, or US welding may form better water proof seals compared to sewing.

Act 620 recites "disposing at least one porous material in a chamber defined between the first panel and the second panel." In an embodiment, the porous material may be attached to one of the first or second panels (e.g., with an adhesive, heat sealing, RF welding, US welding, or any other suitable technique) before act 610. In such an embodiment, positioning the first and second panels adjacent to each other also disposes the porous material in the chamber. In an embodiment, the porous material may be positioned between the first and second panels when the first and second panels are positioned adjacent to each other. In other words, the first panel, the porous material, and the second panel may form a stack with the porous material positioned between the first and second panels. Act 620 may also attach the porous materials to the first and second panels as the first and second panels are attached together. As such, the method 600 does not require a separate act of attaching the porous material to the first and second panels thus making the method 600 more efficient and quicker.

In an embodiment, the porous material is disposed in the chamber after attaching the first and second panels together. In an example, as previously discussed, the porous material is attached to the first and second panel by attaching portions of the fluid impermeable barrier that are adjacent to one or more base gaps and one or more porous material gaps. In an example, the porous material may be attached to one or more of the first or second panels with an adhesive, tape, or the like or the porous material may not be attached to the first and second panels. While not attaching the porous material to the first and second panels may make the method 600 more efficient and quicker, the porous material may move in the chamber, such as by bunching up near the fluid outlet.

In an embodiment, the method 600 may include forming one or more of the first panel, the second panel, and the porous material. In an example, the method 600 may form the first and second panel, for example, by stamping the first and second panels (including any openings, cutouts, or perforation defined thereby). Stamping the first and second panels and attaching the first and second panels together, as discussed above, may be quicker and easier than forming a single sheet into a cylinder. In an example, the porous material may also be stamped from a sheet of the porous material when the porous material exhibits a sheet-like shape. In an example, the first and second panel may be formed using a blown film extrusion technique to form a thin walled tube. In an example, at least one of the first panel, the second panel, or the porous material may be formed by non-stamping techniques or non-blown film extrusion technique even though such techniques may be more complicated or time consuming. Examples of non-stamping and non-blown film extrusion techniques include cutting with a blade, other extrusion techniques, molding (e.g., cast molding), or any other suitable technique.

In an embodiment, the method 600 may include forming the base. In an example, the base may be formed by stamping the base from a sheet (e.g., a sheet that includes a substrate, at least one adhesive layer, and at least one release liner). The base may be formed by stamping since, for instance, the base is formed from a thin film and the base may not include any protrusions, such as a ring-like protrusion defining the aperture. Alternatively, the base may be formed by injection molding, or any other suitable technique even though non-stamping techniques may be more time consuming.

In an embodiment, the method 600 may include attaching (e.g., permanently attaching) the base to the sheath formed at least partially by acts 610 and 620. In an example, the method 600 includes attaching the base to the sheath before providing the fluid collection assembly to an end user. In such an example, the method 600 may include permanently attaching the base to the sheath and, after attaching the base to the sheath, disposing the fluid collection assembly in a package. In an example, the method 600 does not include permanently attaching the base to the sheath before providing the fluid collection assembly to an end user. In such an example, the method 600 may include disposing the fluid collection assembly, with the sheath and the base not attached together, in a package. The end user may remove the fluid collection assembly from the package and may permanently attaching the base to the sheath after removing the fluid collection assembly from the package. For instance, the end user may permanently attach the sheath to the base before, during, or after attaching the base to the skin surround the penis.

It is noted that the embodiments disclosed above relate to fluid collection assemblies configured to collection bodily fluids from a male. However, it is noted that such fluid collection assemblies may also be used to collection bodily fluids from a female since the urethral opening of the female is, functionally, similar to a buried penis.

While various aspects and embodiments have been disclosed herein, other aspects and embodiments are contemplated. The various aspects and embodiments disclosed herein are for purposes of illustration and are not intended to be limiting.

Terms of degree (e.g., "about," "substantially," "generally," etc.) indicate structurally or functionally insignificant variations. In an example, when the term of degree is included with a term indicating quantity, the term of degree is interpreted to mean±10%, ±5%, or ±2% of the term indicating quantity. In an example, when the term of degree is used to modify a shape, the term of degree indicates that the shape being modified by the term of degree has the appearance of the disclosed shape. For instance, the term of degree may be used to indicate that the shape may have rounded corners instead of sharp corners, curved edges instead of straight edges, one or more protrusions extending therefrom, is oblong, is the same as the disclosed shape, etc.

We claim:

1. A fluid collection assembly, comprising:

a sheath including:

a fluid impermeable barrier including a proximal region and a distal region extending from the proximal region, the proximal region including proximal edges opposite the distal region that are attached together, the proximal region exhibiting a first width and the distal region exhibiting a second width that is less than the first width, the proximal region defining an opening, the fluid impermeable barrier at least defining a chamber and a fluid outlet;

at least one porous material disposed in the chamber, the at least one porous material being a sheet; and a port attached to the fluid outlet, the port including a first part defining an inlet and a second part defining an outlet, the first part attached to the fluid impermeable barrier and the second part extending from the first part, the second part configured to be attached to a conduit, the second part configured to be more rigid than the conduit;

a base secured to or configured to be secured to the proximal region of the sheath, the base configured to be attached to skin surrounding a penis, the base defining an aperture that corresponds to the opening of the sheath, the base including a first portion permanently secured to or configured to be permanently secured to the proximal region of the sheath and a second portion that is not permanently secured to or configured to be permanently secured to the proximal region of the sheath, wherein all of the first portion and all of the second portion are immediately adjacent to and abut the sheath.

2. The fluid collection assembly of claim 1, wherein the fluid impermeable barrier includes a first panel and a second panel attached to the first panel.

3. The fluid collection assembly of claim 1, wherein the fluid impermeable barrier includes a first panel and a second panel integrally formed together.

4. The fluid collection assembly of claim 1, wherein the fluid impermeable barrier includes polyurethane.

5. The fluid collection assembly of claim 1, wherein the first width is substantially constant and the second width decreases from the proximal region towards the fluid outlet.

6. The fluid collection assembly of claim 5, wherein the second width decreases at a constant rate.

7. The fluid collection assembly of claim 1, wherein:

the fluid impermeable barrier defines one or more orifices extending therethrough; and the sheath further includes one or more vents attached to the fluid impermeable barrier and covering the one or more orifices, the one or more vents configured to allow air to flow therethrough and prevent water flowing therethrough.

8. The fluid collection assembly of claim 7, wherein the one or more vents includes a porous polytetrafluoroethylene layer attached to a substrate, the substrate attached to the fluid impermeable barrier.

9. The fluid collection assembly of claim 7, wherein the one or more orifices and the one or more vents exhibits an elongated shape.

10. The fluid collection assembly of claim 1, wherein the at least one porous material exhibits a shape that generally corresponds to a shape of the first portion and the second portion of the fluid impermeable barrier.

11. The fluid collection assembly of claim 1, wherein the first part exhibits a first width and the second part exhibits a second width, the first width at least two times greater than the second width.

12. The fluid collection assembly of claim 1, wherein the first part defines sink upstream from the inlet, the sink exhibiting at least one of a width or thickness that is greater than a corresponding width or thickness of the inlet.

13. The fluid collection assembly of claim 1, wherein the port includes at least one tab extending from the first part, the at least one tab extending further into the chamber than a remainder of the port.

14. The fluid collection assembly of claim 1, wherein the base includes a nonwoven substrate.

15. The fluid collection assembly of claim 1, wherein the base defines one or more base gaps therein, the one or more base gaps spaced from the aperture.

16. The fluid collection assembly of claim 15, wherein the at least one porous material defines one or more porous material gaps extending therethrough, wherein the one or more porous material gaps are generally aligned with the one or more base gaps.

17. The fluid collection assembly of claim 16, wherein opposing portions of the fluid impermeable barrier that are generally aligned with the one or more base gaps and the one or more porous material gaps are attached together.

18. The fluid collection assembly of claim 1, wherein that base include an inner region adjacent to the aperture and an outer region spaced from the aperture by the inner region, and wherein the inner region is attached to the fluid impermeable barrier and the outer region is not attached to the fluid impermeable barrier.

19. The fluid collection assembly of claim 1, wherein the base includes one or more concave edges.

20. A system, comprising:

the fluid collection assembly of claim 1:

a vacuum source configured to apply a vacuum force;

a fluid storage container; and at least one conduit connected to the outlet and in fluid communication with the vacuum source and the fluid storage container.

21. A method of manufacturing a fluid collection assembly, the method comprising:

attaching together proximal edges of a fluid impermeable barrier of a sheath, the sheath including a fluid impermeable barrier including a proximal region and a distal region extending from the proximal region, the proximal edges opposite the distal region, the proximal region exhibiting a first width and the distal region exhibiting a second width that is less than the first width, the proximal region defining an opening, the fluid impermeable barrier at least defining a chamber and a fluid outlet, the base configured to be attached to skin surrounding a penis, the base defining an aperture that corresponds to the opening of the sheath after attaching the base to the fluid impermeable barrier;

attaching a portion to the fluid outlet, the port including a first part defining an inlet and a second part defining an outlet, the first pat attached to the fluid impermeable barrier and the second part extending from the first part, the second part configured to be attached to a conduit, the second part configured to be more rigid than the conduit, the first part exhibiting an elongated shape that extends in a direction that is generally perpendicular to a longitudinal axis of the fluid collection assembly, the first part exhibiting a first maximum thickness and the second part exhibiting a second maximum thickness, wherein the first maximum thickness is substantially equal to or less than the second maximum thickness;

permanently attaching a first portion a base to the fluid impermeable barrier of the sheath and not permanently attaching a second portion of the base to the sheath, wherein all of the first portion and all of the second portion are immediately adjacent to and abut the sheath; and disposing at least one porous material in the chamber, the at least one porous material being a sheet.

22. The method of claim 21, further comprising:

providing the fluid impermeable barrier, the fluid impermeable barrier including a first panel and a second panel that is distinct from the first panel; and attaching at least a portion of an outer periphery of the first panel to an outer periphery of the second panel; and wherein attaching the base to the fluid impermeable barrier includes attaching the base to the second panel.

23. The method of claim 22, wherein attaching the base to the first panel is performed before attaching at least a portion of the outer periphery of the first panel to the outer periphery of the second panel.

24. The method of claim 21, further comprising:

providing the base and the at least one porous material, wherein the base includes defines one or more base gaps and the at least one porous material includes one or more porous material gaps, wherein the one or more base gaps and the one or more porous material gaps are generally aligned after disposing the at least one porous material in the chamber; and attaching opposing portions of the fluid impermeable barrier together that are adjacent to the one or more porous material gaps.

25. A method of using a system to collect bodily fluids from an individual, the method comprising:

attaching a base to skin surrounding a penis, the base secured to or configured to be secured to a sheath, the sheath including:

a fluid impermeable barrier including a proximal region and a distal region extending from the proximal region, the proximal region including proximal edges opposite the distal region that are attached together, the proximal region exhibiting a first width and the distal region exhibiting a second width that is less than the first width, the proximal region defining an opening, the fluid impermeable barrier at least defining a chamber and a fluid outlet;

at least one porous material disposed in the chamber, the at least one porous material being a sheet; and a port attached to the fluid outlet, the port including a first part defining an inlet and a second part defining an outlet, the first part attached to the fluid impermeable barrier and the second part extending from the first part, the second part configured to be attached to a conduit, the second part configured to be more rigid than the conduit;

wherein the base includes a proximal portion positioned on a proximal side of the opening and a distal portion positioned on the distal side of the opening, all of the proximal portion exhibits a width that is greater than a width of the distal portion, wherein the proximal portion and the distal portion do not extend past the fluid impermeable barrier.

26. The fluid collection assembly of claim 12, wherein the sink includes at least one tapered surface extending from a maximum width of the sink to the inlet.

27. The fluid collection assembly of claim 1, wherein the fluid impermeable barrier defines a single chamber.

28. The fluid collection assembly of claim 1, wherein the at least one porous material occupies substantially all of the chamber when the fluid collection assembly lies on the flat surface.

29. The fluid collection assembly of claim 1, wherein the at least one porous material exhibits substantially no absorption.

30. The fluid collection assembly of claim 1, wherein the sheet of the at least one porous material extends across the opening when the fluid collection assembly lies on a flat surface.

31. The fluid collection assembly of claim 1, wherein the first part of the port exhibits an elongated shape that extends in a direction that is generally perpendicular to a longitudinal axis of the fluid collection assembly, the first part exhibiting a first maximum thickness and the second part exhibiting a second maximum thickness, wherein the first maximum thickness is substantially equal to or less than the second maximum thickness.

32. The fluid collection assembly of claim 1, wherein the fluid impermeable barrier defines an interior region extending between the proximal region to the distal region, the interior region consisting of a single chamber.

33. The fluid collection assembly of claim 1, wherein the at least one porous material includes a single sheet extending an entire length of the sheath.

* * * * *